(12) United States Patent
Nagaraj et al.

(10) Patent No.: US 8,247,410 B2
(45) Date of Patent: Aug. 21, 2012

(54) PYRIMIDINE SUBSTITUTED PURINE DERIVATIVES

(75) Inventors: Harish K. Nagaraj, Singapore (SG); Meredith Williams, Singapore (SG)

(73) Assignee: Verastem, Cambridge, MA (US)

( * ) Notice: Subject to any disclaimer, the term of this patent is extended or adjusted under 35 U.S.C. 154(b) by 188 days.

(21) Appl. No.: 12/681,584

(22) PCT Filed: Oct. 3, 2008

(86) PCT No.: PCT/SG2008/000379
§ 371 (c)(1),
(2), (4) Date: Jun. 11, 2010

(87) PCT Pub. No.: WO2009/045175
PCT Pub. Date: Apr. 9, 2009

(65) Prior Publication Data
US 2010/0298319 A1    Nov. 25, 2010

Related U.S. Application Data

(60) Provisional application No. 60/977,720, filed on Oct. 5, 2007, provisional application No. 61/075,532, filed on Jun. 25, 2008.

(51) Int. Cl.
*A61K 31/535* (2006.01)
*C07D 413/14* (2006.01)
(52) U.S. Cl. .................................. 514/234.2; 544/117
(58) Field of Classification Search .................. 544/117; 514/234.2
See application file for complete search history.

(56) References Cited

U.S. PATENT DOCUMENTS

| | | | |
|---|---|---|---|
| 4,617,304 | A | 10/1986 | Ashton et al. |
| 4,772,606 | A | 9/1988 | Sircar et al. |
| 2009/0318411 | A1 | 12/2009 | Castanedo et al. |
| 2010/0298319 | A1 | 11/2010 | Nagaraj et al. |
| 2011/0009403 | A1 | 1/2011 | Nagaraj et al. |
| 2011/0105500 | A1 | 5/2011 | Nagaraj et al. |

FOREIGN PATENT DOCUMENTS

| | | |
|---|---|---|
| EP | 1277738 A1 | 1/2003 |
| WO | WO-9901454 A1 | 1/1999 |
| WO | WO-02055521 A1 | 7/2002 |
| WO | WO-03031406 A2 | 4/2003 |
| WO | WO-2004016612 A2 | 2/2004 |
| WO | WO-2004021979 A2 | 3/2004 |
| WO | WO-2004035740 A2 | 4/2004 |
| WO | WO-2004037823 A1 | 5/2004 |
| WO | WO-2004048365 A1 | 6/2004 |
| WO | WO-2007021937 A2 | 2/2007 |
| WO | WO-2007031726 A1 | 3/2007 |
| WO | WO-2007034185 A1 | 3/2007 |
| WO | WO-2008043031 A1 | 4/2008 |
| WO | WO-2008116129 A2 | 9/2008 |
| WO | WO-2009099163 A1 | 8/2009 |
| WO | WO-2010005558 A2 | 1/2010 |
| WO | WO-2010114484 A1 | 10/2010 |
| WO | WO-2010114494 A1 | 10/2010 |

*Primary Examiner* — Rebecca Anderson
(74) *Attorney, Agent, or Firm* — Connolly Bove Lodge & Hutz LLP

(57) ABSTRACT

The present invention relates to purine compounds that are useful as kinase inhibitors. More particularly, the present invention relates to purine compounds, methods for their preparation, pharmaceutical compositions containing these compounds and uses of these compounds in the treatment of proliferative conditions or disorders. These compounds may be useful as medicaments for the treatment of a number of proliferative conditions or disorders including tumors and cancers as well as other disorders or conditions related to or associated with PI3 and/or mTOR kinases.

18 Claims, No Drawings

PYRIMIDINE SUBSTITUTED PURINE DERIVATIVES

CROSS REFERENCE TO RELATED APPLICATIONS

This application is a National Phase filing under 35 U.S.C. §371 of PCT/SG2008/000379 filed Oct. 3, 2008, which claims priority to Provisional Patent Application No. 60/977,720, filed in the United States on Oct. 5, 2007, and Provisional Patent Application No. 61/075,532, filed in the United States on Jun. 25, 2008. The entire contents of each of the above-applications is incorporated herein by reference.

FIELD

The present invention relates to purine compounds that may be useful as kinase inhibitors. More particularly, the present invention relates to 2-(morpholin-4-yl), 6-(pyrimidin-5-yl) substituted purine derivatives, methods for their preparation, pharmaceutical compositions containing these compounds and uses of these compounds in the treatment of certain kinase related disorders/conditions.

BACKGROUND

The search for kinase inhibitors has proven to be a fruitful area for the development of useful pharmaceutically active substances. Kinases, which are alternatively known as phosphotransferases, are enzymes that transfer phosphate groups from high energy donor molecules (for example ATP) to specific target molecules (typically called substrates) in a process termed phosphorylation. One of the largest groups of kinases are the protein kinases which act on and modify the activity of specific proteins.

As a result of this activity these kinases are involved in a number of cellular processes such as in signalling and to prime the cell for biochemical reactions in metabolism. Certain cellular signalling processes have been implicated as important in a number of medical conditions and the effective inhibition of certain cell signalling processes therefore provides the potential to stop these conditions developing. Accordingly, kinases represent an attractive target for medicinal chemists as the provision of kinase inhibitors potentially allows for certain signalling processes to be controlled leading to the control of certain medical conditions.

One family of kinases associated with undesirable medical conditions in the body are the phosphoinositide 3-kinase (PI3) family of kinases which are involved in a wide range of cellular events such as cell migration, cell proliferation, oncogenic transformation, cell survival, signal transduction and intracellular trafficking of proteins. This family of kinases has recently been the focus of much research aimed at developing therapies for a range of indications such as proliferative diseases, for example cancer, immune and inflammatory diseases, diseases supported by excessive neovascularization and transplant rejection.

The phosphoinositide 3-kinase (PI3K) family is a group of enzymes that generate phosphatidylinositol 'second messengers'. These lipids are subsequently involved in a wide range of physiological processes. In mammalian cells, the large PI3K family has been categorized into three classes, referred to as I, II, and III, each of which has its own characteristics in terms of molecular structure and substrate specificity. Class I PI3K preferred in vivo substrate is phosphatidylinositol-4,5 bisphosphate, which is phosphorylated to yield phosphatidylinositol-3,4,5 trisphosphate. These are further subdivided into Class IA and IB PI3Ks. Class IA enzymes consist of any one of the 'catalytic' subunits (p110α, p110β, or p110δ) complexed with any one of the 'regulatory' subunits (p85α, p85β or p55γ). Only one Class IB PI3K enzyme exists, and is made up of the p110γ catalytic and the p101 regulatory subunit. There are also three Class II PI3Ks (CIIα, CIIβ, and CIIδ) and one Class III PI3K (Vps34).

The class I PI3Ks are the best understood members of this family and are key players of multiple intracellular signalling networks that integrate a variety of signals initiated by many growth factors. The Class IA enzymes are activated by tyrosine kinases (e.g. growth factor receptors), antigen receptors, and cytokine receptors, whilst the Class IB enzyme is activated by 'G Protein Coupled Receptors' (GPCRs). In response to activation, the PI3Ks generate lipid second messengers, which bind to, and activate, specific proteins in distinct signal transduction pathways. The signal transduction pathways remain active until phosphatase enzymes, in particular the oncogene PTEN, dephosphorylate the PI3K lipid second messengers.

The PI3K signalling pathway is crucial to many aspects of cell growth and survival via its regulation of widely divergent physiological processes that include cell cycle progression, differentiation, transcription, translation and apoptosis. Constitutive activation of the PI3K pathway has been implicated in both the pathogenesis and progression of a large variety of cancers and there is now a rapidly accumulating body of evidence that demonstrates conclusively that PI3K signalling is frequently deregulated in cancer. The deregulation of PI3K signalling is thought to occur in two different ways. The first is an increase in PI3K signalling resulting from activating gene mutations, amplification and over expression of PI3Ks or upstream receptors that activate PI3Ks. For example, the PI3Kα catalytic subunit is amplified and over expressed in ovarian and cervical cancers. Similarly, upstream receptor tyrosine kinases that activate PI3K are commonly mutated, amplified and over expressed, e.g., EGFR in breast, ovarian and lung cancer.

In addition, activation of the effectors downstream of PI3K can also contribute to deregulation of the PI3K pathway, e.g., Akt/PKB (Protein Kinase B) is over expressed and activated in breast, pancreatic and ovarian cancers among others. Also, the Ras family members, which are involved in PI3K activation, are frequently mutated, e.g. in colorectal and pancreatic cancer. The second mechanism of PI3K deregulation involves loss of the tumor suppressor phosphatase PTEN, which occurs in many aggressive brain tumors, endometrial and breast cancers, and melanomas.

One specific cell signalling pathway mediated by the PI3 family of kinases is the phosphatidylinositol 3-kinase (PI3K)/Akt pathway. This pathway is critically involved in the mediation of cell survival and is a major signalling component downstream of growth factor receptor tyrosine kinases (RTKs). Growth factor RTKs engage the class-IA PI3K, which is a heterodimer comprised of the p85 regulatory and p110 catalytic subunits. The small GTPase Ras can also recruit and activate PI3K through direct binding to p110. At the cell membrane, PI3K catalyzes the production of the lipid second messenger phosphatidylinositol-3,4,5-triphosphate (PIP3). Subsequently, PIP3 recruits other downstream molecules—particularly the serine-threonine kinases Akt and PDK1—via binding to their pleckstrin-homology (PH) domains. At the membrane, Akt is partially activated through phosphorylation at threonine 308 in its activation loop by PDK1. Additional phosphorylation at serine 473 in the C terminus of Akt results in its full activation. Akt in turn regulates a wide range of target proteins, one of which is the mammalian target of Rapamycin (commonly known as mTOR). The levels of PIP3 in the cell are strictly regulated and several lipid phosphatases act to rapidly remove it. Of particular interest is the phosphatase PTEN, which converts PIP3 back to PIP2 and thus shuts off PI3K signalling. The PI3K-Akt signalling pathway regulates many normal cellular processes including cell proliferation, survival, growth, and motility—processes that are critical for tumorigenesis.

The role of the PI3K/Akt pathway in oncogenesis has also been extensively investigated and mutations or altered expression of most of the pathway's components have been widely implicated in many cancers. Gene amplification of p110 occurs in some cases of human ovarian cancer, and amplification of Akt is found in ovarian, breast, and colon cancer. In addition, activating mutations in p85 have been identified in ovarian and colon cancer. Most importantly PTEN has been identified as a major tumor suppressor in humans and loss-of-function mutations in the PTEN gene are extremely common among sporadic glioblastomas, melanomas, prostate cancers, and endometrial carcinomas, and a significant percentage of breast tumors, lung cancers, and lymphomas also bear PTEN mutations. Thus, through a variety of mechanisms, a high percentage of human cancers possess activated PI3K signalling. Significantly, it has been shown that mTOR is important for the oncogenic transformation induced by PI3K and Akt.

In addition to the compelling correlative data presented above, direct proof of the involvement of deregulated PI3K signalling in cancer comes from mouse genetic models. For example, mice with a constitutively activated p85 regulatory subunit of PI3K progress to malignant lymphoma when crossed with p53-knockout mice. Further, retroviral introduction of Akt and Ras caused glioblastomas in mice. Taken together, all these data provide strong validation for the development of novel anticancer strategies targeted at PI3Ks. Indeed recent interest in PI3K inhibitors has been intense with a number of compounds now in development having demonstrated anti-tumor activity in animal models. The most advanced compounds are now undergoing evaluation in phase I clinical trials. Accordingly compounds that are PI3K inhibitors would be expected to show interesting biological activity as PI3K inhibitors have the potential to block the PI3K/Akt signalling pathway and thereby form the basis of therapy in disease involving deregulation of this pathway.

In addition, PI 3-kinase isoforms p110δ and p110γ regulate different aspects of immune and inflammatory responses. Hence there is great interest in the role of PI3-kinase signaling in a range of immune and inflammatory diseases as well as in transplant rejection.

Another area that has received attention has been the serine/threonine kinases. One serine/threonine kinase that has attracted significant interest is mTOR.

mTOR is a serine/threonine kinase of 289 kDa and is a PI3K-like kinase that links mitogenic stimuli and nutrient status to cell growth and division. mTOR was discovered during studies conducted to understand the mechanism of action of rapamycin. Upon entering cells, rapamycin binds to its intracellular target FKBP12 and the complex then binds to and specifically inhibits mTOR. mTOR was, therefore, also named FKBP-RAP associated protein (FRAP), RAP FKBP12 target (RAFT1) and RAP target (RAPT1). Cells responsible for organ rejection stop growing due to rapamycin's ability to inhibit the anabolic signals coordinated by mTOR. Since inhibition of cell growth represents a valid target for treating cancer, designing new drugs that inhibit mTOR will potentially have therapeutic value.

In humans, mTOR mediates anabolic signals from 2 sources namely nutrients that pass into the cell and activated growth factor receptors. It exists in at least two distinct complexes: a rapamycin-sensitive complex, referred to as mTOR complex 1 (mTORC1), defined by its interaction with the accessory protein raptor (regulatory-associated protein of mTOR). The normal activation of mTOR results in an increase in protein translation because mTORC1 phosphorylates and activates the translation regulators eukaryotic initiation factor 4E-binding protein 1 and ribosomal p70 S6 kinase. Therefore, by inhibiting mTOR, rapamycin causes a decrease in phosphorylation of these effectors, and a decrease in protein synthesis, effectively blocking the pro-growth actions of mTOR.

The second complex, mTOR complex 2 (mTORC2), is rapamycin-insensitive and is defined by its interaction with rictor (rapamycin-insensitive companion of mTOR). mTORC2 is involved in the regulation of the pro-survival kinase Akt/PKB by phosphorylating it on S473. Together with the phosphorylation of T308 by PDK1, S473 phosphorylation is necessary for full Akt activation. Recent reports indicate that prolonged treatment with rapamycin in some cells also suppresses the assembly and function of TORC2 to inhibit Akt and that this property of rapamycin contributes to the anti-apoptotic effects of the drug. mTOR is also one of the main downstream effectors in the phosphatidylinositol 3-kinase (PI3K)/Akt pathway and therefore inhibition of mTOR provides a further opportunity to inhibit, at least in part, the PI3K/Akt pathway.

An additional pathway influenced by mTOR that appears to be particularly important in renal cell carcinoma involves the hypoxia-inducible factor (HIF). With loss of Von Hippel-Lindau (VHL) gene function commonly seen in clear cell renal cell cancer, there is accumulation of the oxygen-sensitive transcription factors HIF-1 and HIF-2. An accumulation of these factors yields increased stimulation of vascular endothelial growth factor (VEGF), platelet-derived growth factor, and transforming growth factor. This effect is augmented by the activation of mTOR, which stimulates both a protein stabilization function and a protein translational function and, thus, increases HIF-1 activity.

It has also been determined that tuberous sclerosis complex gene products, TSC1 and TSC2, function together to inhibit mTOR-mediated downstream signalling. Mutations of these genes occur in tuberous sclerosis and their loss of function yields yet another pathway, which leads to increased activity of mTOR and induces VEGF production. TSC2 also regulates HIF. Thus, studies evaluating the impact of TSC1 and TSC2 mutations demonstrate the connection of increased VEGF and activated mTOR pathways to angiogenesis.

So far, four mTOR inhibitors have been tested in clinical trials: the prototype rapamycin and three rapamycin derivatives, CCI-779 (temsirolimus), RAD001 (everolimus) and AP23573. Rapamycin, also named sirolimus, is a natural antibiotic produced by *Streptomyces hygroscopicus*. It was developed initially as an anti-fungal drug directed against *Candida albicans, Cryptococcus neoformans*, and *Aspergillus fumigatus*. Later, rapamycin was developed as an immunosuppressive agent and those studies helped in understanding the mechanism of action of this agent. As an anti-cancer agent, rapamycin was shown to inhibit the growth of several murine and human cancer cell lines in a concentration-dependent manner, both in tissue culture and xenograft models. In the sixty tumor cell lines screened at the National Cancer Institute in the USA, general sensitivity to the drug was seen at doses under 2000 ng/ml, more evident in leukemia, ovarian, breast, central nervous system and small cell lung cancer cell lines. In addition, rapamycin inhibits the oncogenic transformation of human cells induced by either PI3K or Akt and has shown metastatic tumor growth inhibition and anti-angiogenic effects in in vivo mouse models.

Based on these pre-clinical results, clinical trials with rapamycin as an anticancer drug were carried out and rapamycin analogues with more favourable pharmaceutical properties were developed. CCI-779, a more water-soluble ester derivative of rapamycin was identified by investigators at Wyeth Ayerst as a non-cytotoxic agent that delayed tumor cell proliferation. At several non-toxic doses, CCI-779 demonstrated anti-tumor activity alone or in combination with cytotoxic agents in a variety of human cancer models such as gliomas, rhabdomyosarcoma, primitive neuroectodermal tumor such as medulloblastoma, head and neck, prostate, pancreatic and breast cancer cells. Treatment of mice with CCI-779 inhibits p70S6K activity and reduces neoplastic proliferation. As with rapamycin, PTEN-deficient human tumors are more sensitive to CCI-779-mediated growth inhibition than PTEN expressing cells. Specifically, studies in vitro in a panel of eight human breast cancer cell lines showed that six of eight cancer lines studied were inhibited by CCI-779 with $IC_{50}$ in the low nanomolar range. Two lines, however, were found to be resistant with $IC_{50} > 1$ μM. The sensitive cell lines were estrogen receptor positive or over-expressed HER-2/Neu, or had lost the tumor suppressor gene product PTEN. The main toxicities of CCI-779 included dermatological toxicities and mild myelosuppression (mainly thrombocytemia).

RAD001, 40-O-(2-hydroxyethyl)-rapamycin, is another analogue of rapamycin that can be administrated orally. Its anti-neoplastic activity has been evaluated in different human cancer cell lines in vitro and in xenograft models in vivo with $IC_{50}$ ranging from 5 to 1800 nM. p70S6K inhibition and anti-neoplastic effects have been shown in these models, with an optimal effect being achieved with 2.5 mg/kg/day in melanoma, lung, pancreas and colon carcinoma. Similarly, RAD001 demonstrated a concentration-dependent anti-tumor activity in a syngenic rat pancreas carcinoma model with an intermittent dosing schedule. RAD001 has also shown anti-angiogenic activity and inhibits human vascular endothelial cell (HUVEC) proliferation. The toxicity reported for RAD001 includes hypercholesterolemia, hypertriglyceridemia, mild leukocytopenia and thrombocytopenia. In a phase I trial performed in patients with advanced cancer, RAD001 displayed a good safety profile with mild to moderate skin and mucous toxicity up to 30 mg weekly. Preliminary efficacy results showed an objective response in a patient with non-small cell lung carcinoma.

AP23573 is the latest rapamycin analog to be reported in clinical development. It is a phosphorus-containing compound synthesized with the aid of computational modelling studies. AP23573 was found to be stable in organic solvents, aqueous solutions at a variety of pHs and in plasma and whole blood, both in vitro and in vivo and has shown potent inhibition of diverse human tumor cell lines in vitro and as xenografts implanted into nude mice, alone or in combination with cytotoxic or targeted agents. In phase I trials, AP23573 was administered intravenously daily for 5 days every 2 weeks. Dose-limiting toxicity is severe grade 3 oral mucositis occurring during the first cycle. Other side effects seem to be moderate, including minor to moderate episodes of mucositis, fatigue, nausea, rash, anaemia, neutropenia, diarrhoea, hyperlipidemias and thrombocytopenia. Preliminary anti-tumor activity is observed at all dose levels.

There is thus a plethora of studies that demonstrate that mTOR inhibitors can improve cancer patient survival. However, rapamycin and its analogues have not shown universal anti-tumor activity in early clinical trials. Response rates vary among cancer types from a low of less than 10% in patients with glioblastomas and advanced renal-cell cancer to a high of around 40% in patients with mantle-cell lymphoma. Knowledge of the status of PTEN and PI3K/Akt/mTOR-linked pathways might help in the selection of tumor types that will respond to mTOR inhibitors. Furthermore, because many tumor types still do not respond to single agent therapy with rapamycin derivatives, it is important to continue the search for factors predictive of resistance or sensitivity to mTOR inhibitors. Of particular interest will be molecules that directly inhibit mTOR kinase activity, the assumption being that such molecules will inhibit both mTORC1 and mTORC2. Such an inhibitor might be beneficial for treating tumors with elevated Akt phosphorylation and might down-regulate the growth, proliferation and survival effects that are associated with Akt activation. If mTOR-rictor is a crucial activator of Akt-dependent survival processes, such a drug might promote apoptosis in tumor cells that have adapted to Akt-dependent regulatory mechanisms.

In addition mTOR inhibitors have been shown to be very effective in preventing organ rejection after transplantation through an effect on immune responses, demonstrating a potential for treatment of autoimmune and inflammatory diseases as well as cancer.

Through the role of PI3 K isoforms as key components of the down stream signalling pathways of angiogenic growth factors such as VEGF, FGF and PDGF as well angiogenic cytokines and because of the role of mTOR in the regulation of vascular endothelial growth factor (VEGF), PI3 K and mTOR inhibitors also have potential to treat diseases supported by pathological neovascularization. This occurs during tumorigenesis, inflammatory conditions such as rheumatoid arthritis and ocular neovascular diseases e.g., age-related macular degeneration (AMD), retinal vascular diseases (vein occlusion and diabetic retinopathy) and other possible proliferative vascular disorders.

mTOR and PI3 have been identified as protein kinases that are involved in a number of disorders, and compounds that target one or more of these kinases should display useful biological activity. Accordingly, compounds that are mTOR and/or PI3K inhibitors have the potential to provide further biologically active compounds that would be expected to have useful, improved pharmaceutical properties in the treatment of proliferative disorders such as cancer, immune and inflammatory diseases, diseases supported by excessive neovascularisation and organ transplant rejection.

Compounds that inhibit both mTOR and PI3K simultaneously may be expected to provide powerful anti-proliferative, anti-angiogenic and antitumor activity since these compounds act at multiple points in the PI3K/Akt/mTOR pathway. A number of inhibitors of this type are now being investigated in a clinical setting for the first time (e.g. BEZ235, XL765, GDC0941, PX866, SF1126).

SUMMARY

The present invention provides compounds of formula (I):

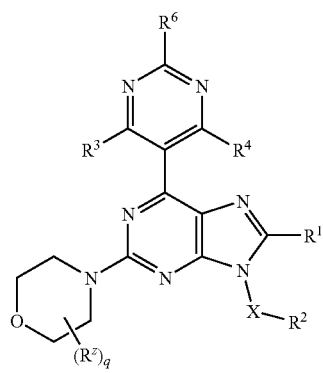

Formula (I)

wherein:

$R^1$ is selected from the group consisting of: H, halogen and optionally substituted $C_1$-$C_6$ alkyl;

$R^2$ is selected from the group consisting of H, halogen, OH, $NO_2$, CN, $NH_2$, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $SR^8$, $SO_3H$, $SO_2NR^8R^9$, $SO_2R^8$, $SONR^8R^9$, $SOR^8$, $COR^8$, COOH, $COOR^8$, $CONR^8R^9$, $NR^8COR^9$, $NR^8COOR^9$, $NR^8SO_2R^9$, $NR^8CONR^8R^9$, $NR^8R^9$, and acyl;

$R^3$, and $R^4$ are each independently selected from the group consisting of H, F, Cl, Br, OH, optionally substituted $C_1$-$C_6$alkyl, $OR^8$, $OCOR^8$, $CH_2OH$, $NH_2$, $NR^8R^9$, $NR^8COR^9$, and $NR^8SO_2R^9$;

$R^6$ is selected from the group consisting of H, OH, $OR^8$, $OP_9^O$, $OCOR^8$, $CH_2OH$, $NH_2$, $NR^8R^9$, $NR^8P_g^N$, $N(P_9^N)_2$, $NR^8COR^9$, and $NR^8SO_2R^9$;

each $R^8$ and $R^9$ is independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{10}$heteroalkyl, optionally substituted $C_3$-$C_{12}$cycloalkyl, optionally substituted $C_3$-$C_{12}$cycloalkenyl, optionally substituted $C_2$-$C_{12}$ heterocycloalkyl, optionally substituted $C_2$-$C_{12}$ heterocycloalkenyl, optionally substituted $C_6$-$C_{18}$aryl, and optionally substituted $C_1$-$C_{18}$heteroaryl; or $R^8$ and $R^9$ when taken together with the atoms to which they are attached form an optionally substituted cyclic moiety;

$P_g^O$ is a protecting group for oxygen;

each $P_g^N$ is independently a protecting group for nitrogen;

each $R^z$ is independently selected from the group consisting of $C_1$-$C_6$alkyl, halo-$C_1$-$C_6$alkyl, hydroxy$C_1$-$C_6$alkyl, $C_1$-$C_6$alkyloxy$C_1$-$C_6$alkyl, cyano$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl;

q is an integer selected from the group consisting of 0, 1, 2, 3, and 4;

X is a group of formula $(CR^{10}_2)_m$;

each $R^{10}$ is independently selected from the group consisting of: H and optionally substituted $C_1$-$C_6$ alkyl;

m is an integer selected from the group consisting of 0, 1, 2, 3 and 4;

or a pharmaceutically acceptable salt, N-oxide, or prodrug thereof.

As with any group of structurally related compounds which possess a particular utility, certain embodiments of variables of the compounds of the Formula (I), are particularly useful in their end use application.

In various embodiments q is an integer selected from the group consisting of 0, 1, 2, 3, and 4. In some embodiments q is 4. In some embodiments q is 3. In some embodiments q is 2. In some embodiments q is 1. In some embodiments q is 0.

In some embodiments wherein q is other than 0 each $R^z$ may be selected from the group consisting of F, Cl, Br, methyl, trifluoromethyl, and ethyl. The $R^z$ substituent may be attached at the 2, 3, 5 or 6 position of the morpholine ring and in circumstances where there are multiple $R^z$ substituents each $R^z$ substituent is located independently of the others such that where there are multiple $R^z$ substituents then two of the $R^z$ substituents may be located on the same carbon on the morpholine ring or each substituent may be located on a different carbon.

In some embodiments q is 1 and the $R^z$ substituent is located at the 3 position of the morpholine ring. This provides compounds of formula (Ia).

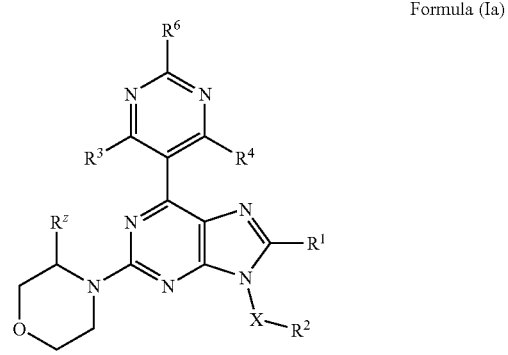

Formula (Ia)

or a pharmaceutically acceptable salt or prodrug thereof; wherein $R^1$, $R^2$, $R^3$, $R^4$, $R^6$, $R^z$ and X are as defined above.

In some embodiments of the compounds of the invention q is 0. This provides compounds of formula (Ib).

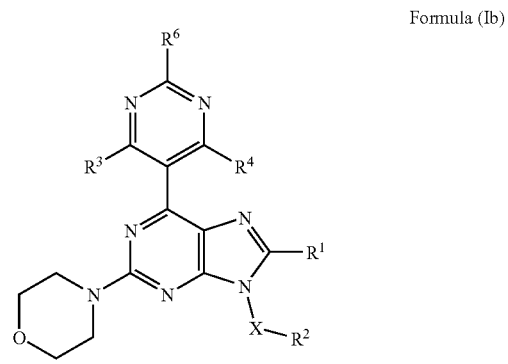

Formula (Ib)

or a pharmaceutically acceptable salt or prodrug thereof; wherein $R^1$, $R^2$, $R^3$, $R^4$, $R^6$ and X are as defined above.

In some embodiments $R^3$ is selected from the group consisting of H, $OR^8$, and optionally substituted $C_1$-$C_6$ alkyl.

In some embodiments $R^3$ is $OR^8$ where $R^8$ is optionally substituted $C_1$-$C_6$alkyl. Examples of $R^3$ groups of this type include methoxy, trifluoro-methoxy, ethoxy, isopropoxy, propoxy, and butoxy. In some embodiments $R^3$ is methoxy.

In some embodiments $R^3$ is optionally substituted $C_1$-$C_6$alkyl. Examples of $R^3$ groups of this type include methyl, trifluoro-methyl, ethyl, propyl, isopropyl, and butyl. In some embodiments $R^3$ is methyl.

In some embodiments $R^3$ is selected from the group consisting of H, methoxy and methyl. In some embodiments $R^3$ is H.

In some embodiments R⁴ is selected from the group consisting of H, F, Cl, Br, OH and NH₂. In some embodiments R⁴ is H.

In some embodiments of the compounds and specifically the compounds of formula (I), (Ia) and (Ib), R³ and R⁴ are both H.

In some embodiments of the invention q=0, R³ is H and R⁴ is H. This provides compounds of formula (Ic):

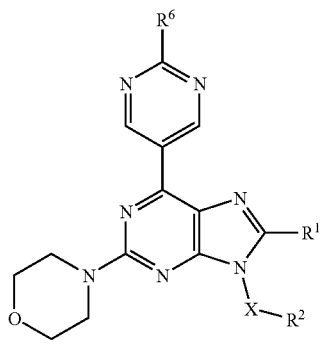

Formula (Ic)

or a pharmaceutically acceptable salt or prodrug thereof; wherein $R^1$, $R^2$, $R^6$, and X are as defined above.

In some embodiments of the compounds containing the group $R^8$, $R^8$ is selected from H and $C_1$-$C_6$alkyl. In some embodiments $R^8$ is methyl. In some embodiments $R^8$ is H.

In some embodiments of the compounds containing the group $R^9$, $R^9$ is selected from H and $C_1$-$C_6$alkyl. In some embodiments $R^9$ is methyl. In some embodiments $R^9$ is H.

As stated previously X is a group of formula $(CR^{10}_2)_m$. In some embodiments of the compounds of formula (I), (Ia), (Ib) and (Ic) m is selected from the group consisting of 0, 1, and 2. In some embodiments m is 0 or 1. In some embodiments m is 0. In some embodiments m is 1.

In some embodiments q=0, R³ is H, R⁴ is H and m is 0. This provides compounds of formula (II):

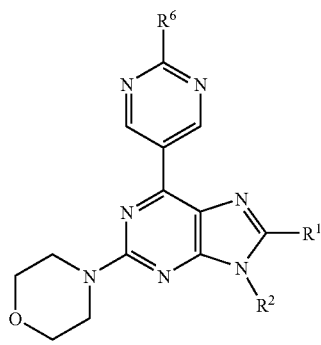

Formula (II)

or a pharmaceutically acceptable salt or prodrug thereof; wherein $R^1$, $R^2$, and $R^6$, are as defined above.

In some embodiments q=0, R³ is H, R⁴ is H and m is 1. This provides compounds of formula (III):

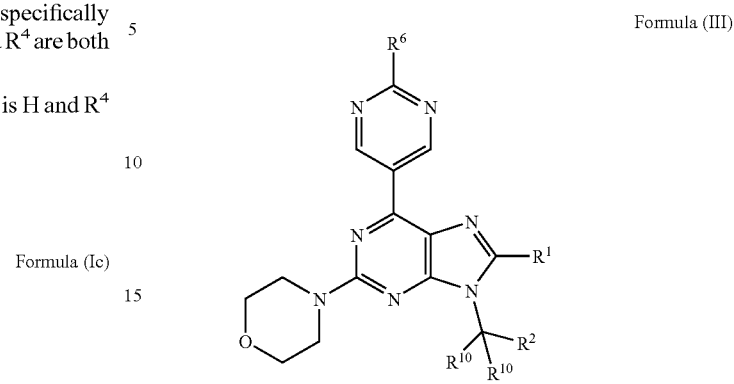

Formula (III)

or a pharmaceutically acceptable salt or prodrug thereof; wherein $R^1$, $R^2$, $R^6$ and $R^{10}$ are as defined above.

In some embodiments of the compounds of formula (I), (Ia), (Ib), (Ic) and (III) each $R^{10}$ is H. In some embodiments each $R^{10}$ is independently an optionally substituted $C_1$-$C_6$alkyl. In some embodiments one $R^{10}$ is H and the other is CH₃. In some embodiments one $R^{10}$ is H and the other $R^{10}$ is H or optionally substituted $C_1$-$C_6$alkyl.

In some embodiments of the compounds of formula (I), (Ia), (Ib), (Ic) and (III) m is 1, one $R^{10}$ is H and X is a group of the formula:

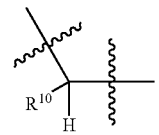

In some embodiments of the invention R³ and R⁴ are H, m is 1, q is 0 and one $R^{10}$ is H. This provides compounds of the formula (IV):

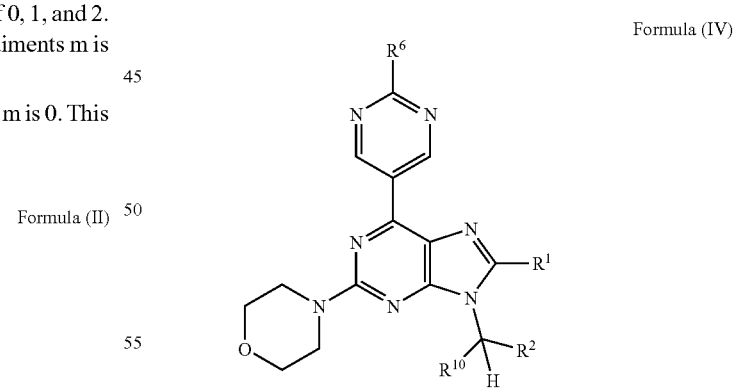

Formula (IV)

or a pharmaceutically acceptable salt or prodrug thereof, wherein $R^1$, $R^2$, $R^6$ and $R^{10}$ are as defined above.

In some embodiments of the compounds containing $R^{10}$ and specifically compounds of formula (I), (Ia), (Ib), (Ic), (III) and (IV) $R^{10}$ is selected from the group consisting of H, $C_1$-$C_6$haloalkyl, $C_1$-$C_6$hydroxyalkyl and $C_1$-$C_6$alkyl. In some embodiments $R^{10}$ is selected from the group consisting of methyl, ethyl, propyl, isopropyl, and butyl. In some embodiments $R^{10}$ is selected from the group consisting of H, methyl and ethyl.

In some embodiments of the compounds of the invention and specifically the compounds of formula (I), (Ia), (Ib), (Ic), (II), (III) and (IV) $R^1$ is selected from the group consisting of H, Br, methyl, ethyl, isopropyl, propyl, 3,3-dimethyl-propyl, butyl, isobutyl, 3,3-dimethyl-butyl, 2-ethyl-butyl, pentyl, and hexyl. In some embodiments $R^1$ is selected from the group consisting of H, methyl and ethyl. In some embodiments $R^1$ is H. In some embodiments $R^1$ is methyl. In some embodiments $R^1$ is ethyl. In some embodiments $R^1$ is Br.

In some embodiments of the compounds of the invention and specifically the compounds of formula (I), (Ia), (Ib), (Ic), (II), (III) and (IV) $R^6$ is selected from the group consisting of H, $NH_2$ and $NR^8R^9$ wherein $R^8$ and $R^9$ are as defined above. In some embodiments $R^6$ is $NH_2$.

In some embodiments of the compounds of the invention and specifically the compounds of (I), (Ia), (Ib), (Ic), (II), (III) and (IV) $R^2$ is selected from the group consisting of H, cyano, optionally substituted $C_1$-$C_{12}$alkyl, optionally substituted $C_2$-$C_{12}$ alkenyl, optionally substituted $C_2$-$C_{12}$heteroalkyl, optionally substituted $C_3$-$C_{12}$ cycloalkyl, optionally substituted $C_2$-$C_{12}$heterocycloalkyl, optionally substituted $C_6$-$C_{18}$ aryl, and optionally substituted $C_1$-$C_{18}$heteroaryl.

In some embodiments $R^2$ is an optionally substituted $C_6$-$C_{18}$ aryl. In some embodiments of $R^2$ the optionally substituted $C_6$-$C_{18}$ aryl is a group of the formula:

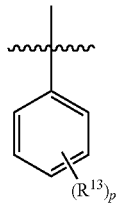

wherein p is an integer selected from the group consisting of 0, 1, 2, 3, 4, and 5;

each $R^{13}$ is independently selected from the group consisting of H, halogen, OH, $NO_2$, CN, $NH_2$, optionally substituted $C_1$-$C_{12}$alkyl, optionally substituted $C_2$-$C_{12}$ alkenyl, optionally substituted $C_2$-$C_{12}$alkynyl, optionally substituted $C_2$-$C_1$heteroalkyl, optionally substituted $C_3$-$C_{12}$cycloalkyl, optionally substituted $C_2$-$C_{12}$ heterocycloalkyl, optionally substituted $C_2$-$C_{12}$heterocycloalkenyl, optionally substituted $C_6$-$C_{18}$ aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$ aryloxy, optionally substituted $C_1$-$C_{18}$heteroaryloxy, optionally substituted $C_1$-$C_{12}$ alkylamino, $SR^8$, $SO_3H$, $SO_2NH_2$, $SO_2R^8$, $SONH_2$, $SOR^8$, $COR^8$, COOH, $COOR^8$, $CONR^8R^9$, $NR^8COR^9$, $NR^8COOR^9$, $NR^8SO_2R^9$, $NR^8CONR^8R^9$, $NR^8R^9$, and acyl;

where $R^8$ and $R^9$ are as defined above.

The phenyl group may be unsubstituted or may be optionally substituted with one or more suitable substituent groups. If the phenyl group is substituted then there may be 1, 2, 3, 4 or 5 substituent groups. In some embodiments p is 0, 1 or 2. In some embodiments p is 1. In some embodiments p is 2.

In some embodiments of $R^2$ the optionally substituted $C_6$-$C_{18}$ aryl is a group of the formula:

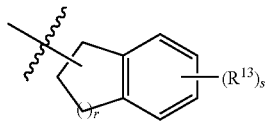

wherein $R^{13}$ is as defined above;

s is an integer selected from the group consisting of 0, 1, 2, 3 and 4;

r is an integer selected from the group consisting of 1, 2, and 3.

In some embodiments r is 1 and the optionally substituted $C_6$-$C_{18}$ aryl is a group of the formula:

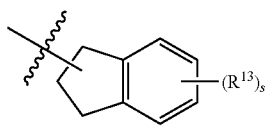

wherein $R^{13}$ and s are as defined above.

In some embodiments r is 2 and the optionally substituted $C_6$-$C_{18}$ aryl is a group of the formula:

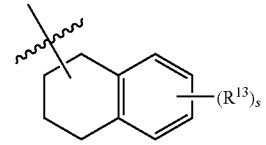

wherein $R^{13}$ and s are as defined above.

In some embodiments s is selected from the group consisting of 0, 1, and 2. In some embodiments s is 1. In some embodiments s is 1. In some embodiments s is 2.

Each $R^{13}$ substituent may be selected from any suitable substituent. In some embodiments each $R^{13}$ is independently selected from the group consisting of H, F, $CH_3$, $CH_2CH_3$, $OCH_3$, CN, $OCF_3$, $CO_2CH_3$, $NO_2$, $NH_2$, $NHCOCH_3$, $NHSO_2CH_3$, $NHCH_2CH_3$, and $CF_3$.

In some embodiments $R^1$ is H, $R^3$ is H, $R^4$ is H, $R^6$ is $NH_2$, X is $(CH_2)_m$ wherein m is 0, and $R^2$ is a group of the formula:

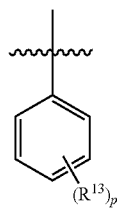

This provides compounds of formula (V):

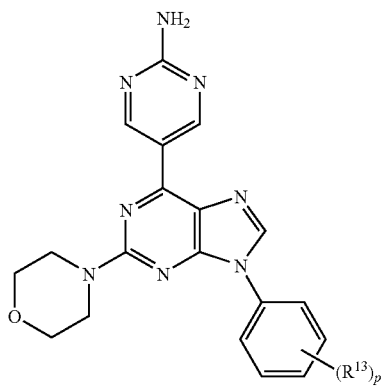

Formula (V)

or a pharmaceutically acceptable salt or prodrug thereof; wherein $R^{13}$ and p are as defined above.

In some embodiments $R^1$ is H, $R^3$ is H, $R^4$ is H, $R^6$ is $NH_2$, X is $(CH_2)_m$ wherein m is 1, and $R^2$ is a group of the formula:

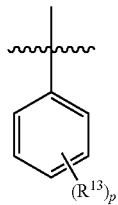

This provides compounds of formula (Va):

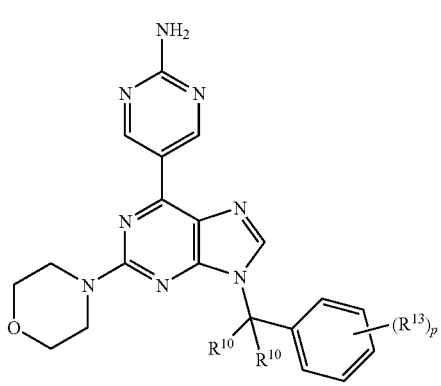

Formula (Va)

or a pharmaceutically acceptable salt or prodrug thereof; wherein $R^{13}$, $R^{10}$ and p are as defined above.

In some embodiments of the compounds of formula (I), (Ia), (Ib), (Ic), (II), (III) and (IV) $R^2$ is selected from the group consisting of cyano, optionally substituted $C_1$-$C_{12}$ alkyl, and optionally substituted $C_2$-$C_{12}$heteroalkyl.

In some embodiments of the compounds of formula (I), (Ia), (Ib), (Ic), (II), (III) and (IV) $R^2$ is selected from the group consisting of methyl, ethyl, isopropyl, propyl, butyl, sec-butyl, isobutyl, 3,3-dimethyl-butyl, 2-ethyl-butyl, pentyl, hexyl, heptyl, and octyl.

In some embodiments of the compounds of formula (I), (Ia), (Ib), (Ic), (II), (III) and (IV) $R^2$ is an optionally substituted methyl group of the formula:

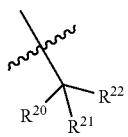

wherein $R^{20}$, $R^{21}$ and $R^{22}$ are each independently selected from the group consisting of H, Cl, Br, F, OH, $NO_2$, CN, $NH_2$, optionally substituted $C_1$-$C_{12}$alkyl, optionally substituted $C_2$-$C_{12}$heteroalkyl, optionally substituted $C_3$-$C_{12}$cycloalkyl, optionally substituted $C_2$-$C_{12}$heterocycloalkyl, optionally substituted $C_6$-$C_{18}$aryl, and optionally substituted $C_1$-$C_{18}$heteroaryl; or any two or more of $R^{20}$, $R^{21}$ and $R^{22}$ when taken together with the carbon atom to which they are attached form a cyclic moiety.

In some embodiments each $R^{20}$, $R^{21}$ and $R^{22}$ is independently selected from the group consisting of H, Cl, Br, F, OH, $NO_2$, CN, $NH_2$, methyl, ethyl, propyl, isopropyl, butyl, pentyl, methoxymethyl, 2-methoxyethyl, 3-methoxypropyl, 2-ethoxyethyl, 3-ethoxypropyl, aminomethyl, 2-aminoethyl, 3-aminopropyl, 4-aminobutyl, 5 aminopentyl, methylaminomethyl, 2-methylaminoethyl, 3-methylaminopropyl. 4-methylaminobutyl, 5-methylaminopentyl, ethylaminomethyl, 2-ethylaminoethyl, 3-ethylaminopropyl, 4-ethylaminobutyl, 5-ethylaminopentyl, dimethylaminomethyl, 2-dimethylaminoethyl, 3-dimethylaminopropyl, 4-dimethylaminobutyl, 5-dimethylaminopentyl, diethylaminomethyl, 2-diethylaminoethyl, 3-diethylaminopropyl, 4-diethylaminobutyl and 5-diethylaminopentyl.

In some embodiments $R^2$ is optionally substituted $C_3$-$C_{12}$cycloalkyl. In some embodiments $R^2$ is selected from the group consisting of cyclopropyl, cyclobutyl, cyclopentyl and cyclohexyl. In some embodiments $R^2$ is cyclopropyl.

In some embodiments $R^2$ is optionally substituted $C_2$-$C_{12}$heterocycloalkyl.

In some embodiments $R^2$ is selected from the group consisting of optionally substituted pyrrolidin-1-yl, optionally substituted pyrrolidin-2-yl, optionally substituted pyrrolidin-3-yl, optionally substituted dioxolane-2-yl, optionally substituted dioxolane-3-yl, optionally substituted tetrahydrofuran-2-yl, optionally substituted tetrahydrofuran-3-yl, optionally substituted piperidine-1-yl, optionally substituted piperidine-2-yl, optionally substituted piperidine-3-yl, optionally substituted piperidine-4-yl, optionally substituted morpholine-2-yl, optionally substituted morpholine-3-yl, optionally substituted 1,4,dioxolane-2-yl, optionally substituted thiomorpholine-2-yl, optionally substituted thiomorpholine-3-yl, optionally substituted thiomorpholine-4-yl, optionally substituted piperazine-1-yl and optionally substituted piperazine-2-yl.

In some embodiments the optionally substituted $C_2$-$C_{12}$heterocycloalkyl group is selected from the group consisting of:

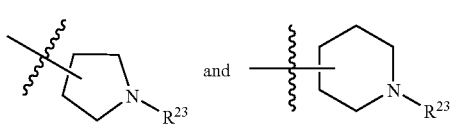

wherein $R^{23}$ is independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $SO_2NR^{24}R^{25}$, $SOR^{24}$, $SO_2R^{24}$, $SONR^{24}R^{25}$, $SOR^{24}$, $COR^{24}$, $COOH$, $COOR^{24}$, and $CONR^{24}R^{25}$;

each $R^{24}$ and $R^{25}$ is independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{10}$heteroalkyl, optionally substituted $C_3$-$C_{12}$cycloalkyl, optionally substituted $C_3$-$C_{12}$cycloalkenyl, optionally substituted $C_2$-$C_{12}$ heterocycloalkyl, optionally substituted $C_2$-$C_{12}$ heterocycloalkenyl, optionally substituted $C_6$-$C_{18}$aryl, and optionally substituted $C_1$-$C_{18}$heteroaryl.

In some embodiments the optionally substituted $C_2$-$C_{12}$heterocycloalkyl group is selected from the group consisting of:

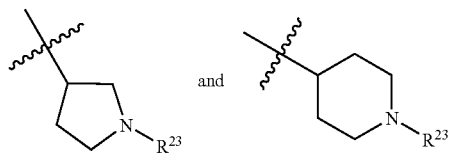

wherein $R^{23}$ is as defined above.

In some embodiments $R^{23}$ is selected from the group consisting of H, $COR^{24}$, and $COOR^{24}$.

In some embodiments $R^{24}$ is selected from the group consisting of H, optionally substituted $C_1$-$C_{12}$alkyl, optionally substituted $C_6$-$C_{18}$aryl, and optionally substituted $C_1$-$C_{18}$heteroaryl. In some embodiments $R^{24}$ is $C_1$-$C_6$ alkyl.

In some embodiments $R^2$ is an optionally substituted $C_2$-$C_1$ heteroalkyl group. In some embodiments the $C_2$-$C_{12}$ heteroalkyl group is selected from the group consisting of hydroxy$C_1$-$C_6$alkyl, $C_1$-$C_6$alkyloxy$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl. Examples of possible values of $R^2$ as $C_2$-$C_{12}$ heteroalkyl include hydroxymethyl, hydroxyethyl, hydroxypropyl, hydroxybutyl, hydroxypentyl, methoxymethyl, 2-methoxyethyl, 3-methoxypropyl, 2-ethoxyethyl, 3-ethoxypropyl, aminomethyl, 2-aminoethyl, 3-aminopropyl, 4-aminobutyl, 5 aminopentyl, methylaminomethyl, 2-methylaminoethyl, 3-methylaminopropyl, 4-methylaminobutyl, 5-methylaminopentyl, ethylaminomethyl, 2-ethylaminoethyl, 3-ethylaminopropyl, 4-ethylaminobutyl, 5-ethylaminopentyl, dimethylaminomethyl, 2-dimethylaminoethyl, 3-dimethylaminopropyl, 4-dimethylaminobutyl, 5-dimethylaminopentyl, diethylaminomethyl, 2-diethylaminoethyl, 3-diethylaminopropyl, 4-diethylaminobutyl and 5-diethylaminopentyl.

In some embodiments $R^2$ is $COOR^8$ wherein $R^8$ is as defined above. In some embodiments $R^2$ is $COOR^8$ and $R^8$ is $C_1$-$C_{12}$alkyl. Examples of groups of this type include $COOCH_3$, $COOCH_2CH_3$ and the like.

In some embodiments $R^2$ is $CONR^8R^9$ wherein each $R^8$ and $R^9$ is independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{10}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, and optionally substituted $C_1$-$C_{18}$heteroaryl, or $R^8$ and $R^9$ when taken together with the atoms to which they are attached form an optionally substituted cyclic moiety;

In some embodiments where $R^2$ is $CONR^8R^9$ then $R^8$ and $R^9$ are each independently selected from the group consisting of H, $C_1$-$C_{12}$alkyl, $C_3$-$C_{12}$ cycloalkyl and $C_1$-$C_{18}$aryl. Examples of $R^2$ groups of this type include $CONHCH(CH_3)_2$, CONHcyclopropyl, and CONHphenyl.

In some embodiments where $R^2$ is $CONR^8R^9$ then $R^8$ and $R^9$ when taken together with the atoms to which they are attached form a cyclic moiety. Examples of $R^2$ groups of this type include:

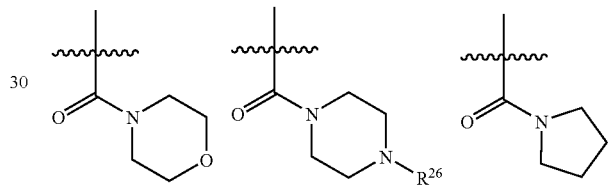

Wherein $R^{26}$ is independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$ heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$ alkylamino, H, $SO_2NR^{27}R^{28}$, $SO_2R^{27}$, $SONR^{27}R^{28}$, $SOR^{27}$, $COR^{27}$, $COOH$, $COOR^{27}$, and $CONR^{27}R^{28}$;

each $R^{27}$ and $R^{28}$ is independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{10}$heteroalkyl, optionally substituted $C_3$-$C_{12}$cycloalkyl, optionally substituted $C_3$-$C_{12}$cycloalkenyl, optionally substituted $C_2$-$C_{12}$ heterocycloalkyl, optionally substituted $C_2$-$C_{12}$ heterocycloalkenyl, optionally substituted $C_6$-$C_{18}$aryl, and optionally substituted $C_1$-$C_{18}$heteroaryl.

In some embodiments $R^2$ is selected from the group consisting of methyl, ethyl, isopropyl, propyl, 3,3-dimethyl-propyl, cyclopropyl, cyclopentyl, 3-methycyclopentyl, cyclohexyl, 4-methylcyclohexyl, butyl, sec-butyl, isobutyl, 3,3-dimethyl-butyl, 2-ethyl-butyl, pentyl, pent-4-enyl, hexyl, heptyl, octyl, cyano, methoxymethyl, butoxymethyl, t-butoxymethy and tetrahydrofuran-3-yl, Many if not all of the variables discussed above may be optionally substituted. If the variable is optionally substituted then in some embodiments each optional substituent is independently selected from the group consisting of halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)R$^a$, —C(=O)OR$^a$, C(=O)NR$^a$R$^b$, C(=NOH)R$^a$, C(=NR$^a$)NR$^b$R$^c$, NR$^a$R$^b$, NR$^a$C(=O)R$^b$, NR$^a$C(=O)OR$^b$, NR$^a$C(=O)NR$^b$R$^c$, NR$^a$C(=NR$^b$)NR$^c$R$^d$, NR$^a$SO$_2$R$^b$, —SR$^a$, SO$_2$NR$^a$R$^b$, —OR$^a$, OC(=O)NR$^a$R$^b$, OC(=O)R$^a$ and acyl, wherein R$^a$, R$^b$, R$^c$ and R$^d$ are each independently selected from the group consisting of H, C$_1$-C$_{12}$alkyl, C$_1$-C$_{12}$haloalkyl, C$_2$-C$_{12}$alkenyl, C$_2$-C$_{12}$alkynyl, heteroalkyl, C$_3$-C$_{12}$cycloalkyl, C$_3$-C$_{12}$cycloalkenyl, C$_1$-C$_{12}$heterocycloalkyl, C$_1$-C$_{12}$ heterocycloalkenyl, C$_6$-C$_{18}$aryl, C$_1$-C$_{18}$heteroaryl, and acyl, or any two or more of R$^a$, R$^b$, R$^c$ and R$^d$, when taken together with the atoms to which they are attached form a heterocyclic ring system with 3 to 12 ring atoms.

Alternatively, two adjacent optional; substituents may, when taken together with the atoms to which they are attached, form a cyclic moiety such as an optionally substituted C$_3$-C$_{12}$ cycloalkyl moiety or an optionally substituted C$_2$-C$_{12}$ heterocycloalkyl moiety.

In some embodiments each optional substituent is independently selected from the group consisting of: F, Cl, Br, =O, =S, —CN, —NO$_2$, alkyl, alkenyl, heteroalkyl, haloalkyl, alkynyl, aryl, cycloalkyl, heterocycloalkyl, heteroaryl, hydroxy, hydroxyalkyl, alkoxy, alkylamino, aminoalkyl, acylamino, phenoxy, alkoxyalkyl, benzyloxy, alkylsulfonyl, arylsulfonyl, aminosulfonyl, —C(O)OR$^a$, COOH, SH, and acyl.

In some embodiments each optional substituent is independently selected from the group consisting of: F, Br, Cl, =O, =S, —CN methyl, trifluoro-methyl, ethyl, 2,2,2-trifluoroethyl, isopropyl, propyl, 2-ethyl-propyl, 3,3-dimethyl-propyl, butyl, isobutyl, 3,3-dimethyl-butyl, 2-ethyl-butyl, pentyl, 2-methyl-pentyl, pent-4-enyl, hexyl, heptyl, octyl, phenyl, NH$_2$, —NO$_2$, phenoxy, hydroxy, methoxy, trifluoro-methoxy, ethoxy, and methylenedioxy.

In addition to compounds of Formula I, the embodiments disclosed are also directed to pharmaceutically acceptable salts, pharmaceutically acceptable N-oxides, pharmaceutically acceptable prodrugs, and pharmaceutically active metabolites of such compounds, and pharmaceutically acceptable salts of such metabolites.

The invention also relates to pharmaceutical compositions including a compound of the invention with a pharmaceutically acceptable carrier, diluent or excipient.

In a further aspect the invention provides a method of inhibiting a protein kinase selected from the group consisting of a serine/threonine protein kinase or a fragment or a complex thereof or a functional equivalent thereof and a PI3 kinase or a fragment or a complex thereof or a functional equivalent thereof, the method including exposing the protein kinase or a fragment or complex thereof or a functional equivalent thereof and/or co-factor(s) thereof to an effective amount of a compound of the invention.

The compounds disclosed herein may act directly and solely on the kinase molecule or a complex or fragment thereof to inhibit biological activity. However, it is understood that the compounds may also act at least partially on co-factors that are involved in the phosphorylation process. Known kinase co-factors include ionic species (such as zinc and calcium), lipids (such as phosphatidylserine), and diacylglycerols.

In some embodiments the protein kinase is a serine/threonine protein kinase or a fragment or a complex thereof or a functional equivalent thereof. In some embodiments the serine/threonine protein kinase or a fragment or complex thereof is an mTOR protein kinase or a fragment thereof, or a complex thereof or a functional equivalent thereof. In some embodiments the serine/threonine protein kinase is mTORC1 or a fragment or complex thereof or a functional equivalent thereof.

In some embodiments the protein kinase is a PI3 kinase or a fragment thereof or a complex thereof or a functional equivalent thereof. In some embodiments the PI3 kinase or a fragment thereof or a complex thereof or a functional equivalent thereof, is a class I PI3K or a fragment thereof or a complex thereof or a functional equivalent thereof.

In one embodiment of the method exposing the one or more protein kinase(s) to the compound includes administering the compound to a mammal containing the one or more protein kinase(s).

In an even further aspect the invention provides the use of a compound of the invention to inhibit one or more protein kinase(s) selected from the group consisting of a serine/threonine protein kinase or a fragment or a complex thereof or a functional equivalent thereof and a PI3 kinase or a fragment or a complex thereof or a functional equivalent thereof.

In some embodiments the protein kinase is a serine/threonine protein kinase or a fragment or a complex thereof or a functional equivalent thereof. In some embodiments the serine/threonine protein kinase or a fragment or complex thereof is an mTOR protein kinase or a fragment thereof, or a complex thereof or a functional equivalent thereof. In some embodiments the serine/threonine protein kinase is mTORC1 or a fragment or complex thereof or a functional equivalent thereof.

In some embodiments the protein kinase is a PI3 kinase or a fragment thereof or a complex thereof or a functional equivalent thereof. In some embodiments the PI3 kinase or a fragment thereof or a complex thereof or a functional equivalent thereof, is a class I PI3K or a fragment thereof or a complex thereof or a functional equivalent thereof.

In an even further aspect the invention provides a method of treating or preventing a condition in a mammal in which inhibition of one or more protein kinase(s) selected from the group consisting of a serine/threonine protein kinase or a fragment or a complex thereof or a functional equivalent thereof and a PI3 kinase or a fragment or a complex thereof or a functional equivalent thereof, prevents, inhibits or ameliorates a pathology or a symptomology of the condition, the method including administration of a therapeutically effective amount of a compound of the invention.

In some embodiments the protein kinase is a serine/threonine protein kinase or a fragment or a complex thereof or a functional equivalent thereof. In some embodiments the serine/threonine protein kinase or a fragment or complex thereof is an mTOR protein kinase or a fragment thereof, or a complex thereof or a functional equivalent thereof. In some embodiments the serine/threonine protein kinase is mTORC1 or a fragment or complex thereof or a functional equivalent thereof.

In some embodiments the protein kinase is a PI3 kinase or a fragment thereof or a complex thereof or a functional equivalent thereof. In some embodiments the PI3 kinase or a fragment thereof or a complex thereof or a functional equivalent thereof, is a class I PI3K or a fragment thereof or a complex thereof or a functional equivalent thereof.

In some embodiments the condition is cancer. In some embodiments the cancer is selected from the group consisting of Hematologic cancer such as myeloproliferative disorders (idiopathic myelofibrosis, polycythemia vera, essential thrombocythemia, chronic myeloid leukemia), myeloid metaplasia, chronic myelomonocytic leukemia, acute lymphocytic leukemia, acute erythroblastic leukemia, Hodgkin's and Non Hodgkin's disease, B-cell lymphoma, acute T-cell leukemia, myelodysplastic syndromes, plasma cell disorder, hairy cell leukemia, kaposi's sarcoma, lymphoma and hyperproliferative conditions such as psoriasis and restenosis; gynaecologic cancer such as breast carcinoma, ovarian cancer, cervical cancer, vaginal and vulva cancer, endometrial hyperplasia; gastrointestinal tract cancer such as colorectal carcinoma, polyps, liver cancer, gastric cancer, pancreatic cancer, gall bladder cancer; urinary tract cancer such as prostate cancer, kidney and renal cancer; urinary bladder cancer, urethral cancer, penile cancer; skin cancer such as melanoma; brain tumour such as glioblastoma, neuroblastoma, astrocytoma, ependynoma, brain-stem gliomas, medulloblastoma, menigiomas, astrocytoma, oligodendroglioma; head and neck cancer such as nasopharyngeal carcinoma, laryngeal carcinoma; respiratory tract cancer such as lung carcinoma (NSCLC and SCLC), mesothelioma; eye disease such as retinoblastoma; musculo-skeleton diseases such as osteosarcoma, musculoskeleletal neoplasm; Squamous cell carcinoma and fibroid tumour. In other embodiments, compounds of this invention can be used to treat pre-cancer conditions or hyperplasia including familial adenomatous polyposis, colonic adenomatous polyps, myeloid dysplasia, endometrial dysplasia, endometrial hyperplasia with atypia, cervical dysplasia, vaginal intraepithelial neoplasia, benign prostatic hyperplasia, papillomas of the larynx, actinic and solar keratosis, seborrheic keratosis and keratoacanthoma.

In some embodiments the condition is an autoimmune or inflammatory disease or a disease supported by excessive neovascularisation. Diseases that have been attributed with some degree of autoimmune etiology, or that involve pathological inflammatory and neovascularization responses, include the following: acute disseminated encephalomyelitis, Addison's disease, agammaglobulinemia, agranulocytosis, allergic asthma, allergic encephalomyelitis, allergic rhinitis, alopecia areata, alopecia senilis, anerythroplasia, ankylosing spondylitis, antiphospholipid antibody syndrome, aortitis syndrome, aplastic anemia, atopic dermatitis, autoimmune haemolytic anemia, autoimmune hepatitis, autoimmune oophoritis, Balo disease, Basedow's disease, Behcet's disease, bronchial asthma, Castleman's syndrome, celiac disease, Chagas disease, chronic inflammatory demyelinating polyneuropathy, Churg-Strauss syndrome, Cogans syndrome, comical cornea, comical leukoma, Coxsackie myocarditis, CREST disease, Crohn's disease, cutaneous eosinophilia, cutaneous T-cell lymphoma, dermatitis erythrema multiforme, dermatomyositis, diabetic retinopathy, Dressler's syndrome, dystrophia epithelialis corneae, eczematous dermatitis, eosinophilic fasciitis, eosinophilic gastroenteritis, epidermolysis bullosa, Evans syndrome, fibrosing alveolitis, gestational pemphigoid, glomerulonephritis, Goodpasture's syndrome, graft-versus-host disease, Graves' disease, Guillain-Barre Syndrome, Hashimoto's disease, haemolytic-uretic syndrome, herpetic keratitis, ichthyosis vulgaris, idiopathic intersititial pneumonia, idiopathic thrombocytopenic purpura, inflammatory bowel diseases, Kawasaki's disease, keratitis, keratoconjunctivitis, Lambert-Eaton syndrome, leukoderma vulgaris, lichen planus, lichen sclerosus, Lyme disease, linear IgA disease, macular degeneration, megaloblastic anemia, Meniere's disease, Mooren's ulcer, Mucha-Habermann disease, multiple myositis, multiple sclerosis, myasthenia gravis, necrotizing enterocolitis, neuromyelitis optica, ocular pemphigus, opsoclonus myoclonus syndrome, Ord's thyroiditis, paroxysmal nocturnal hemoglobinuria, Parsonnage-Turner syndrome, pemphigus, periodontitis, pernicious anemia, pollen allergies, polyglandular autoimmune syndrome, posterior uveitis, primary biliary cirrhosis, proctitis, pseudomembranous colitis, psoriasis, pulmonary emphysema, pyoderma, Reiter's syndrome, reversible obstructive airway disease, rheumatic fever, rheumatoid arthritis, sarcoidosis, scleritis, Sezary's syndrome, Sjogren's syndrome, subacute bacterial endocarditis, systemic lupus erythematosus, Takayasu's arteritis, temporal arteritis, Tolosa-Hunt syndrome, Type I diabetes mellitus, ulcerative colitis, urticaria, vernal conjunctivitis, vitiligo, Vogy-Koyanagi-Harada syndrome and Wegener's granulomatosis.

In an even further aspect the invention provides use of a compound of the invention in the preparation of a medicament for treating a condition in an animal in which inhibition of one or more protein kinase(s) selected from the group consisting of a serine/threonine protein kinase or a fragment or a complex thereof or a functional equivalent thereof and a PI3 kinase or a fragment or a complex thereof or a functional equivalent thereof, prevents, inhibits or ameliorates a pathology or a symptomology of the condition.

In another aspect the present invention provides the use of a compound of the invention or a pharmaceutically acceptable salt, N-oxide or prodrug thereof in the treatment of a condition in which inhibition of one or more protein kinase(s) selected from the group consisting of a serine/threonine protein kinase or a fragment or a complex thereof or a functional equivalent thereof and a PI3 kinase or a fragment or a complex thereof or a functional equivalent thereof, prevents, inhibits or ameliorates a pathology or a symptomology of the condition In some embodiments the protein kinase is a serine/threonine protein kinase or a fragment or a complex thereof or a functional equivalent thereof. In some embodiments the serine/threonine protein kinase or a fragment or complex thereof is an mTOR protein kinase or a fragment thereof, or a complex thereof or a functional equivalent thereof. In some embodiments the serine/threonine protein kinase is mTORC1 or a fragment or complex thereof or a functional equivalent thereof.

In some embodiments the protein kinase is a PI3 kinase or a fragment thereof or a complex thereof or a functional equivalent thereof. In some embodiments the PI3 kinase or a fragment thereof or a complex thereof or a functional equivalent thereof, is a class I PI3K or a fragment thereof or a complex thereof or a functional equivalent thereof.

In another aspect the present invention provides a method of prevention or treatment of a proliferative condition in a subject, the method including administration of a therapeutically effective amount of a compound of the invention.

In another aspect the present invention provides the use of a compound of the invention in the preparation of a medicament for treating a proliferative condition in a subject.

In some embodiments the condition is cancer. In some embodiments the cancer is selected from the group consisting of Hematologic cancer such as myeloproliferative disorders (idiopathic myelofibrosis, polycythemia vera, essential thrombocythemia, chronic myeloid leukemia), myeloid metaplasia, chronic myelomonocytic leukemia, acute lymphocytic leukemia, acute erythroblastic leukemia, Hodgkin's and Non Hodgkin's disease, B-cell lymphoma, acute T-cell leukemia, myelodysplastic syndromes, plasma cell disorder, hairy cell leukemia, kaposi's sarcoma, lymphoma; gynaecologic cancer such as breast carcinoma, ovarian cancer, cervical cancer, vaginal and vulva cancer, endometrial hyperplasia; gastrointestinal tract cancer such as colorectal carcinoma, polyps, liver cancer, gastric cancer, pancreatic cancer, gall bladder cancer; urinary tract cancer such as prostate cancer, kidney and renal cancer; urinary bladder cancer, urethral cancer, penile cancer; skin cancer such as melanoma; brain tumour such as glioblastoma, neuroblastoma, astrocytoma, ependynoma, brain-stem gliomas, medulloblastoma, menigiomas, astrocytoma, oligodendroglioma; head and neck cancer such as nasopharyngeal carcinoma, laryngeal carcinoma; respiratory tract cancer such as lung carcinoma (NSCLC and SCLC), mesothelioma; eye disease such as retinoblastoma; musculo-skeleton diseases such as osteosarcoma, musculoloskeleletal neoplasm; Squamous cell carcinoma and fibroid tumour.

These and other features of the present teachings are set forth herein.

DETAILED DESCRIPTION

In this specification a number of terms are used which are well known to a skilled addressee. Nevertheless for the purposes of clarity a number of terms will be defined.

As used herein, the term "unsubstituted" means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)R$^a$, —C(=O)OR$^a$, C(=O)NR$^a$R$^b$, C(=NOH)R$^a$, C(=NR$^a$)NR$^b$R$^c$, NR$^a$R$^b$, NR$^a$C(=O)R$^b$, NR$^a$C(=O)OR$^b$, NR$^a$C(=O)NR$^b$R$^c$, NR$^a$C(=NR$^b$)NR$^c$R$^d$, NR$^a$SO$_2$R$^b$, —SR$^a$, SO$_2$NR$^a$R$^b$, —OR$^a$, OC(=O)NR$^a$R$^b$, OC(=O)R$^a$ and acyl, wherein R$^a$, R$^b$, R$^c$ and R$^d$ are each independently selected from the group consisting of H, C$_1$-C$_{12}$alkyl, C$_1$-C$_{12}$haloalkyl, C$_2$-C$_{12}$alkenyl, C$_2$-C$_{12}$alkynyl, C$_2$-C$_{10}$heteroalkyl, C$_3$-C$_{12}$cycloalkyl, C$_3$-C$_{12}$cycloalkenyl, C$_2$-C$_{12}$heterocycloalkyl, C$_2$-C$_{12}$heterocycloalkenyl, C$_6$-C$_{18}$aryl, C$_1$-C$_{18}$heteroaryl, and acyl, or any two or more of R$^a$, R$^b$, R$^c$ and R$^d$, when taken together with the atoms to which they are attached form a heterocyclic ring system with 3 to 12 ring atoms.

In some embodiments each optional substituent is independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, —COOH, —SH, and acyl.

Examples of particularly suitable optional substituents include F, Cl, Br, I, CH$_3$, CH$_2$CH$_3$, OH, OCH$_3$, CF$_3$, OCF$_3$, NO$_2$, NH$_2$, and CN.

In the definitions of a number of substituents below it is stated that "the group may be a terminal group or a bridging group". This is intended to signify that the use of the term is intended to encompass the situation where the group is a linker between two other portions of the molecule as well as where it is a terminal moiety. Using the term alkyl as an example, some publications would use the term "alkylene" for a bridging group and hence in these other publications there is a distinction between the terms "alkyl" (terminal group) and "alkylene" (bridging group). In the present application no such distinction is made and most groups may be either a bridging group or a terminal group.

"Acyl" means an R—C(=O)— group in which the R group may be an alkyl, cycloalkyl, heterocycloalkyl, aryl or heteroaryl group as defined herein. Examples of acyl include acetyl and benzoyl. The group may be a terminal group or a bridging group. If the group is a terminal group it is bonded to the remainder of the molecule through the carbonyl carbon.

"Acylamino" means an R—C(=O)—NH— group in which the R group may be an alkyl, cycloalkyl, heterocycloalkyl, aryl or heteroaryl group as defined herein. The group may be a terminal group or a bridging group. If the group is a terminal group it is bonded to the remainder of the molecule through the nitrogen atom.

"Alkenyl" as a group or part of a group denotes an aliphatic hydrocarbon group containing at least one carbon-carbon double bond and which may be straight or branched preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkenyloxy" refers to an alkenyl-O— group in which alkenyl is as defined herein. Preferred alkenyloxy groups are $C_1$-$C_6$ alkenyloxy groups. The group may be a terminal group or a bridging group. If the group is a terminal group it is bonded to the remainder of the molecule through the oxygen atom.

"Alkyl" as a group or part of a group refers to a straight or branched aliphatic hydrocarbon group, preferably a $C_1$-$C_{12}$ alkyl, more preferably a $C_1$-$C_{10}$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Alkylamino" includes both mono-alkylamino and dialkylamino, unless specified. "Mono-alkylamino" means a Alkyl-NH— group, in which alkyl is as defined herein. "Dialkylamino" means a (alkyl)$_2$N— group, in which each alkyl may be the same or different and are each as defined herein for alkyl. The alkyl group is preferably a $C_1$-$C_6$ alkyl group. The group may be a terminal group or a bridging group. If the group is a terminal group it is bonded to the remainder of the molecule through the nitrogen atom.

"Alkylaminocarbonyl" refers to a group of the formula (Alkyl)$_x$(H)$_y$NC(=O)— in which alkyl is as defined herein, x is 1 or 2, and the sum of X+Y=2. The group may be a terminal group or a bridging group. If the group is a terminal group it is bonded to the remainder of the molecule through the carbonyl carbon.

"Alkyloxy" refers to an alkyl-O— group in which alkyl is as defined herein. Preferably the alkyloxy is a $C_1$-$C_6$alkyloxy. Examples include, but are not limited to, methoxy and ethoxy. The group may be a terminal group or a bridging group.

"Alkyloxyalkyl" refers to an alkyloxy-alkyl-group in which the alkyloxy and alkyl moieties are as defined herein. The group may be a terminal group or a bridging group. If the group is a terminal group it is bonded to the remainder of the molecule through the alkyl group.

"Alkyloxyaryl" refers to an alkyloxy-aryl-group in which the alkyloxy and aryl moieties are as defined herein. The group may be a terminal group or a bridging group. If the group is a terminal group it is bonded to the remainder of the molecule through the aryl group.

"Alkyloxycarbonyl" refers to an alkyl-O—C(=O)— group in which alkyl is as defined herein. The alkyl group is preferably a $C_1$-$C_6$ alkyl group. Examples include, but are not limited to, methoxycarbonyl and ethoxycarbonyl. The group may be a terminal group or a bridging group. If the group is a terminal group it is bonded to the remainder of the molecule through the carbonyl carbon.

"Alkyloxycycloalkyl" refers to an alkyloxy-cycloalkyl-group in which the alkyloxy and cycloalkyl moieties are as defined herein. The group may be a terminal group or a bridging group. If the group is a terminal group it is bonded to the remainder of the molecule through the cycloalkyl group.

"Alkyloxyheteroaryl" refers to an alkyloxy-heteroaryl-group in which the alkyloxy and heteroaryl moieties are as defined herein. The group may be a terminal group or a bridging group. If the group is a terminal group it is bonded to the remainder of the molecule through the heteroaryl group.

"Alkyloxyheterocycloalkyl" refers to an alkyloxy-heterocycloalkyl-group in which the alkyloxy and heterocycloalkyl moieties are as defined herein. The group may be a terminal group or a bridging group. If the group is a terminal group it is bonded to the remainder of the molecule through the heterocycloalkyl group.

"Alkylsulfinyl" means an alkyl-S—(=O)— group in which alkyl is as defined herein. The alkyl group is preferably a $C_1$-$C_6$ alkyl group. Exemplary alkylsulfinyl groups include, but not limited to, methylsulfinyl and ethylsulfinyl. The group may be a terminal group or a bridging group. If the group is a terminal group it is bonded to the remainder of the molecule through the sulfur atom.

"Alkylsulfonyl" refers to an alkyl-S(=O)$_2$— group in which alkyl is as defined above. The alkyl group is preferably a $C_1$-$C_6$alkyl group. Examples include, but not limited to methylsulfonyl and ethylsulfonyl. The group may be a terminal group or a bridging group. If the group is a terminal group it is bonded to the remainder of the molecule through the sulfur atom.

"Alkynyl" as a group or part of a group means an aliphatic hydrocarbon group containing a carbon-carbon triple bond and which may be straight or branched preferably having from 2-12 carbon atoms, more preferably 2-10 carbon atoms, more preferably 2-6 carbon atoms in the normal chain. Exemplary structures include, but are not limited to, ethynyl and propynyl. The group may be a terminal group or a bridging group.

"Alkynyloxy" refers to an alkynyl-O— group in which alkynyl is as defined herein. Preferred alkynyloxy groups are $C_1$-$C_6$alkynyloxy groups. The group may be a terminal group or a bridging group. If the group is a terminal group it is bonded to the remainder of the molecule through the oxygen atom.

"Aminoalkyl" means an NH$_2$-alkyl-group in which the alkyl group is as defined herein. The group may be a terminal group or a bridging group. If the group is a terminal group it is bonded to the remainder of the molecule through the alkyl group.

"Aminosulfonyl" means an NH$_2$—S(=O)$_2$— group. The group may be a terminal group or a bridging group. If the group is a terminal group it is bonded to the remainder of the molecule through the sulfur atom.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group.

"Arylalkenyl" means an aryl-alkenyl-group in which the aryl and alkenyl are as defined herein. Exemplary arylalkenyl groups include phenylallyl. The group may be a terminal group or a bridging group. If the group is a terminal group it is bonded to the remainder of the molecule through the alkenyl group.

"Arylalkyl" means an aryl-alkyl-group in which the aryl and alkyl moieties are as defined herein. Preferred arylalkyl groups contain a $C_{1-5}$alkyl moiety. Exemplary arylalkyl groups include benzyl, phenethyl, 1-naphthalenemethyl and 2-naphthalenemethyl. The group may be a terminal group or a bridging group. If the group is a terminal group it is bonded to the remainder of the molecule through the alkyl group.

"Arylalkyloxy" refers to an aryl-alkyl-O— group in which the alkyl and aryl are as defined herein. The group may be a terminal group or a bridging group. If the group is a terminal group it is bonded to the remainder of the molecule through the oxygen atom.

"Arylamino" includes both mono-arylamino and di-arylamino unless specified. Mono-arylamino means a group of formula arylNH—, in which aryl is as defined herein. di-arylamino means a group of formula (aryl)$_2$N— where each aryl may be the same or different and are each as defined herein for aryl. The group may be a terminal group or a bridging group. If the group is a terminal group it is bonded to the remainder of the molecule through the nitrogen atom.

"Arylheteroalkyl" means an aryl-heteroalkyl-group in which the aryl and heteroalkyl moieties are as defined herein. The group may be a terminal group or a bridging group. If the group is a terminal group it is bonded to the remainder of the molecule through the heteroalkyl group.

"Aryloxy" refers to an aryl-O— group in which the aryl is as defined herein. Preferably the aryloxy is a $C_6$-$C_{18}$aryloxy, more preferably a $C_6$-$C_{10}$aryloxy. The group may be a terminal group or a bridging group. If the group is a terminal group it is bonded to the remainder of the molecule through the oxygen atom.

"Arylsulfonyl" means an aryl-S(=O)$_2$— group in which the aryl group is as defined herein. The group may be a terminal group or a bridging group. If the group is a terminal group it is bonded to the remainder of the molecule through the sulfur atom.

A "bond" is a linkage between atoms in a compound or molecule. The bond may be a single bond, a double bond, or a triple bond.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. A cycloalkenyl group typically is a $C_3$-$C_{12}$ alkenyl group. The group may be a terminal group or a bridging group.

"Cycloalkyl" refers to a saturated monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_{12}$ alkyl group. The group may be a terminal group or a bridging group.

"Cycloalkylalkyl" means a cycloalkyl-alkyl-group in which the cycloalkyl and alkyl moieties are as defined herein. Exemplary monocycloalkylalkyl groups include cyclopropylmethyl, cyclopentylmethyl, cyclohexylmethyl and cycloheptylmethyl. The group may be a terminal group or a bridging group. If the group is a terminal group it is bonded to the remainder of the molecule through the alkyl group.

"Cycloalkylalkenyl" means a cycloalkyl-alkenyl-group in which the cycloalkyl and alkenyl moieties are as defined herein. The group may be a terminal group or a bridging group. If the group is a terminal group it is bonded to the remainder of the molecule through the alkenyl group.

"Cycloalkylheteroalkyl" means a cycloalkyl-heteroalkyl-group in which the cycloalkyl and heteroalkyl moieties are as defined herein. The group may be a terminal group or a bridging group. If the group is a terminal group it is bonded to the remainder of the molecule through the heteroalkyl group.

"Cycloalkyloxy" refers to a cycloalkyl-O— group in which cycloalkyl is as defined herein. Preferably the cycloalkyloxy is a $C_1$-$C_6$cycloalkyloxy. Examples include, but are not limited to, cyclopropanoxy and cyclobutanoxy. The group may be a terminal group or a bridging group. If the group is a terminal group it is bonded to the remainder of the molecule through the oxygen atom.

"Cycloalkenyloxy" refers to a cycloalkenyl-O— group in which the cycloalkenyl is as defined herein. Preferably the cycloalkenyloxy is a $C_1$-$C_6$cycloalkenyloxy. The group may be a terminal group or a bridging group. If the group is a terminal group it is bonded to the remainder of the molecule through the oxygen atom.

"Haloalkyl" refers to an alkyl group as defined herein in which one or more of the hydrogen atoms has been replaced with a halogen atom selected from the group consisting of fluorine, chlorine, bromine and iodine. A haloalkyl group typically has the formula $C_nH_{(2n+1-m)}X_m$ wherein each X is independently selected from the group consisting of F, Cl, Br and I. In groups of this type n is typically from 1 to 10, more preferably from 1 to 6, most preferably 1 to 3. m is typically 1 to 6, more preferably 1 to 3. Examples of haloalkyl include fluoromethyl, difluoromethyl and trifluoromethyl.

"Haloalkenyl" refers to an alkenyl group as defined herein in which one or more of the hydrogen atoms has been replaced with a halogen atom independently selected from the group consisting of F, Cl, Br and I.

"Haloalkynyl" refers to an alkynyl group as defined herein in which one or more of the hydrogen atoms has been replaced with a halogen atom independently selected from the group consisting of F, Cl, Br and I.

"Halogen" represents chlorine, fluorine, bromine or iodine.

"Heteroalkyl" refers to a straight- or branched-chain alkyl group preferably having from 2 to 12 carbons, more preferably 2 to 6 carbons in the chain, in which one or more of the carbon atoms (and any associated hydrogen atoms) are each independently replaced by a heteroatomic group selected from S, O, P and NR' where R' is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl. Exemplary heteroalkyls include alkyl ethers, secondary and tertiary alkyl amines, amides, alkyl sulfides, and the like. Examples of heteroalkyl also include hydroxy$C_1$-$C_6$alkyl, $C_1$-$C_6$alkyloxy$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl. The group may be a terminal group or a bridging group.

"Heteroalkyloxy" refers to an heteroalkyl-O— group in which heteroalkyl is as defined herein. Preferably the heteroalkyloxy is a $C_2$-$C_6$heteroalkyloxy. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. A heteroaryl group is typically a $C_1$-$C_{18}$ heteroaryl group. The group may be a terminal group or a bridging group.

"Heteroarylalkyl" means a heteroaryl-alkyl group in which the heteroaryl and alkyl moieties are as defined herein. Preferred heteroarylalkyl groups contain a lower alkyl moiety. Exemplary heteroarylalkyl groups include pyridylmethyl. The group may be a terminal group or a bridging group. If the group is a terminal group it is bonded to the remainder of the molecule through the alkyl group.

"Heteroarylalkenyl" means a heteroaryl-alkenyl-group in which the heteroaryl and alkenyl moieties are as defined herein. The group may be a terminal group or a bridging group. If the group is a terminal group it is bonded to the remainder of the molecule through the alkenyl group.

"Heteroarylheteroalkyl" means a heteroaryl-heteroalkyl-group in which the heteroaryl and heteroalkyl moieties are as defined herein. The group may be a terminal group or a bridging group. If the group is a terminal group it is bonded to the remainder of the molecule through the heteroalkyl group.

"Heteroaryloxy" refers to a heteroaryl-O— group in which the heteroaryl is as defined herein. Preferably the heteroaryloxy is a $C_1$-$C_{18}$heteroaryloxy. The group may be a terminal group or a bridging group. If the group is a terminal group it is bonded to the remainder of the molecule through the oxygen atom.

"Heterocyclic" refers to saturated, partially unsaturated or fully unsaturated monocyclic, bicyclic or polycyclic ring system containing at least one heteroatom selected from the group consisting of nitrogen, sulfur and oxygen as a ring atom. Examples of heterocyclic moieties include heterocycloalkyl, heterocycloalkenyl and heteroaryl.

"Heterocycloalkenyl" refers to a heterocycloalkyl group as defined herein but containing at least one double bond. A heterocycloalkenyl group typically is a $C_2$-$C_{12}$ heterocycloalkenyl group. The group may be a terminal group or a bridging group.

"Heterocycloalkyl" refers to a saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane. A heterocycloalkyl group typically is a $C_2$-$C_{12}$ heterocycloalkyl group. The group may be a terminal group or a bridging group.

"Heterocycloalkylalkyl" refers to a heterocycloalkyl-alkyl-group in which the heterocycloalkyl and alkyl moieties are as defined herein. Exemplary heterocycloalkylalkyl groups include (2-tetrahydrofuryl)methyl, (2-tetrahydrothiofuranyl)methyl. The group may be a terminal group or a bridging group. If the group is a terminal group it is bonded to the remainder of the molecule through the alkyl group.

"Heterocycloalkylalkenyl" refers to a heterocycloalkyl-alkenyl-group in which the heterocycloalkyl and alkenyl moieties are as defined herein. The group may be a terminal group or a bridging group. If the group is a terminal group it is bonded to the remainder of the molecule through the alkenyl group.

"Heterocycloalkylheteroalkyl" means a heterocycloalkyl-heteroalkyl-group in which the heterocycloalkyl and heteroalkyl moieties are as defined herein. The group may be a terminal group or a bridging group. If the group is a terminal group it is bonded to the remainder of the molecule through the heteroalkyl group.

"Heterocycloalkyloxy" refers to a heterocycloalkyl-O— group in which the heterocycloalkyl is as defined herein. Preferably the heterocycloalkyloxy is a $C_1$-$C_6$heterocycloalkyloxy. The group may be a terminal group or a bridging group. If the group is a terminal group it is bonded to the remainder of the molecule through the oxygen atom.

"Heterocycloalkenyloxy" refers to a heterocycloalkenyl-O— group in which heterocycloalkenyl is as defined herein. Preferably the Heterocycloalkenyloxy is a $C_1$-$C_6$ Heterocycloalkenyloxy. The group may be a terminal group or a bridging group. If the group is a terminal group it is bonded to the remainder of the molecule through the oxygen atom.

"Hydroxyalkyl" refers to an alkyl group as defined herein in which one or more of the hydrogen atoms has been replaced with an OH group. A hydroxyalkyl group typically has the formula $C_nH_{(2n+1-x)}(OH)_x$. In groups of this type n is typically from 1 to 10, more preferably from 1 to 6, most preferably 1 to 3. x is typically 1 to 6, more preferably 1 to 3.

"Lower alkyl" as a group means unless otherwise specified, an aliphatic hydrocarbon group which may be straight or branched having 1 to 6 carbon atoms in the chain, more preferably 1 to 4 carbons such as methyl, ethyl, propyl (n-propyl or isopropyl) or butyl (n-butyl, isobutyl or tertiary-butyl). The group may be a terminal group or a bridging group.

"Sulfinyl" means an R—S(=O)— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfinylamino" means an R—S(=O)—NH— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the nitrogen atom.

"Sulfonyl" means an R—S(=O)$_2$— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfonylamino" means an R—S(=O)$_2$—NH— group. The group may be a terminal group or a bridging group. If the group is a terminal group it is bonded to the remainder of the molecule through the nitrogen atom.

It is understood that included in the family of compounds of Formula (I) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Additionally, Formula (I) is intended to cover, where applicable, solvated as well as unsolvated forms of the compounds. Thus, each formula includes compounds having the indicated structure, including the hydrated as well as the non-hydrated forms.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

"Prodrug" means a compound that undergoes conversion to a compound of formula (I) within a biological system, usually by metabolic means (e.g. by hydrolysis, reduction or oxidation). For example an ester prodrug of a compound of formula (I) containing a hydroxyl group may be convertible by hydrolysis in vivo to the parent molecule. Suitable esters of compounds of formula (I) containing a hydroxyl group, are for example acetates, citrates, lactates, tartrates, malonates, oxalates, salicylates, propionates, succinates, fumarates, maleates, methylene-bis-β-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound of formula (I) containing a carboxy group may be convertible by hydrolysis in vivo to the parent molecule. (Examples of ester prodrugs are those described by F. J. Leinweber, Drug Metab. Res., 18:379, 1987). Similarly, an acyl prodrug of a compound of formula (I) containing an amino group may be convertible by hydrolysis in vivo to the parent molecule (Many examples of prodrugs for these and other functional groups, including amines, are described in Prodrugs: Challenges and Rewards (Parts 1 and 2); Ed V. Stella, R. Borchardt, M. Hageman, R. Oliyai, H. Maag and J Tilley; Springer, 2007)

The term "oxygen protecting group" means a group that can prevent the oxygen moiety reacting during further derivatisation of the protected compound and which can be readily removed when desired. In one embodiment the protecting group is removable in the physiological state by natural metabolic processes. Examples of oxygen protecting groups include acyl groups (such as acetyl), ethers (such as methoxy methyl ether (MOM), B-methoxy ethoxy methyl ether (MEM), p-methoxy benzyl ether (PMB), methylthio methyl ether, Pivaloyl (Piv), Tetrahydropyran (THP)), andsilyl ethers (such as Trimethylsilyl (TMS) tert-butyl dimethyl silyl (TBDMS) and triisopropylsilyl (TIPS).

The term "nitrogen protecting group" means a group that can prevent the nitrogen moiety reacting during further derivatisation of the protected compound and which can be readily removed when desired. In one embodiment the protecting group is removable in the physiological state by natural metabolic processes. Examples of suitable nitrogen protecting groups that may be used include formyl, trityl, phthalimido, acetyl, trichloroacetyl, chloroacetyl, bromoacetyl, iodoacetyl; urethane-type blocking groups such as benzyloxycarbonyl ('CBz'), 4-phenyl benzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl ('tBoc'), 2-(4-xenyl)-isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxy-carbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfono)-ethoxycarbonyl, 2-(methylsulfono) ethoxycarbonyl, 2-(triphenylphosphino)-ethoxycarbonyl, fluorenylmethoxycarbonyl ("FMOC"), 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decycloxy)benzyloxycarbonyl, isobornyloxycarbonyl, 1-piperidyloxycarbonlyl and the like; benzoylmethylsulfono group, 2-nitrophenylsulfenyl, diphenylphosphine oxide, and the like. The actual nitrogen protecting group employed is not critical so long as the derivatised nitrogen group is stable to the condition of subsequent reaction(s) and can be selectively removed as required without substantially disrupting the remainder of the molecule including any other nitrogen protecting group(s). Further examples of these groups are found in: Greene, T. W. and Wuts, P. G. M., Protective Groups in Organic Synthesis, Second edition; Wiley-Interscience: 1991; Chapter 7; McOmie, J. F. W. (ed.), Protective Groups in Organic Chemistry, Plenum Press, 1973; and Kocienski, P. J., Protecting Groups, Second Edition, Theime Medical Pub., 2000.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The term "functional equivalent" is intended to include variants of the specific protein kinase species described herein. It will be understood that kinases may have isoforms, such that while the primary, secondary, tertiary or quaternary structure of a given kinase isoform is different to the protoypical kinase, the molecule maintains biological activity as a protein kinase. Isoforms may arise from normal allelic variation within a population and include mutations such as amino acid substitution, deletion, addition, truncation, or duplication. Also included within the term "functional equivalent" are variants generated at the level of transcription. Many kinases (including JAK2 and CDK2) have isoforms that arise from transcript variation. It is also known that FLT3 has an isoform that is the result of exon-skipping. Other functional equivalents include kinases having altered post-translational modification such as glycosylation.

Specific compounds of the invention include the following:

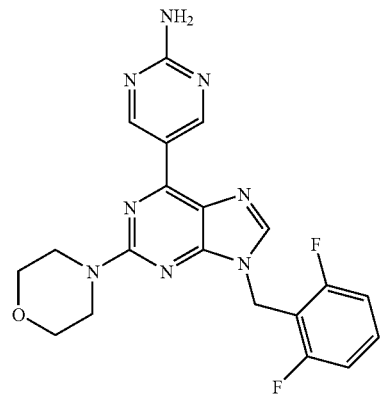

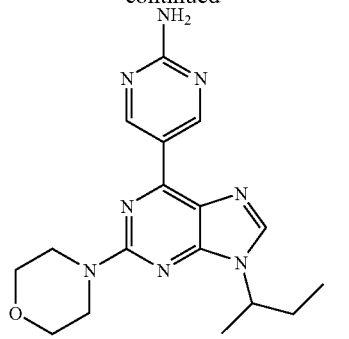
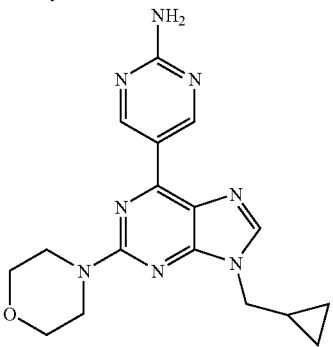
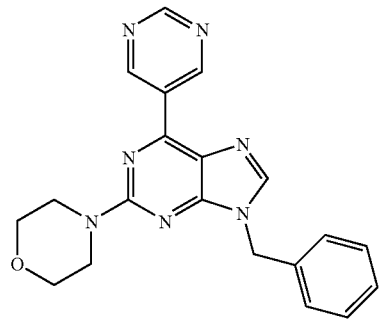
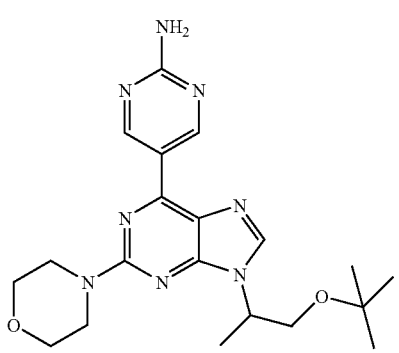
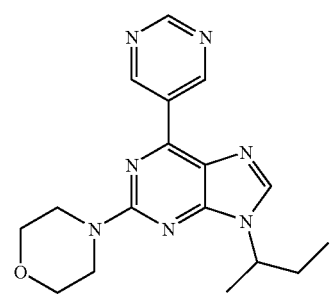
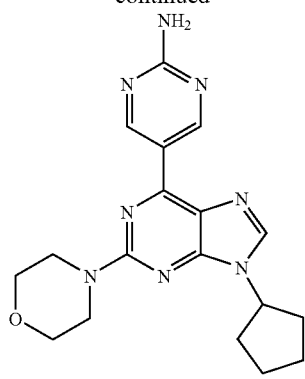
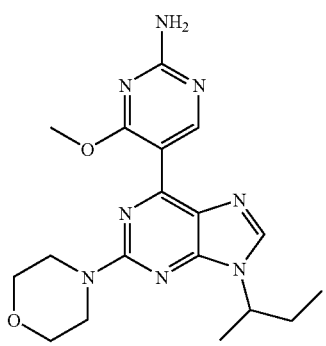
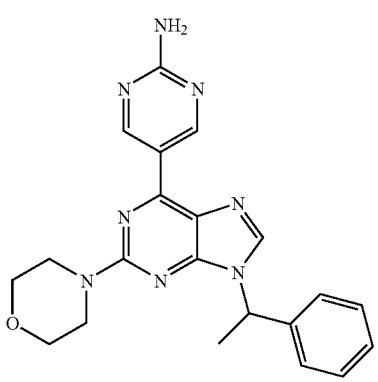
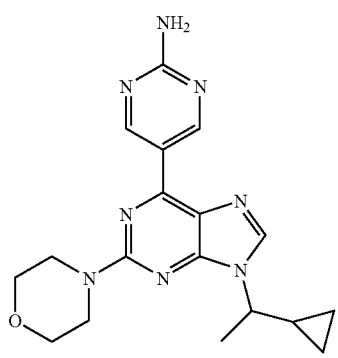

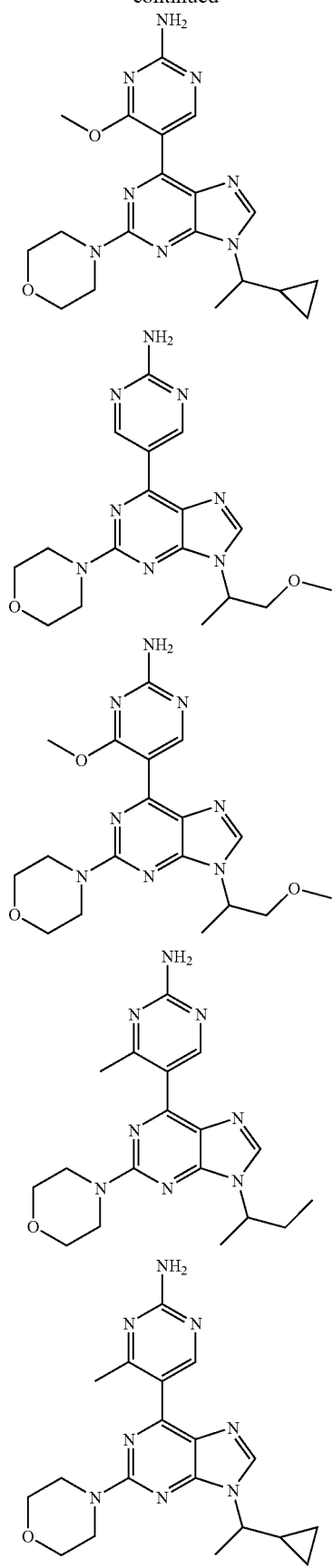
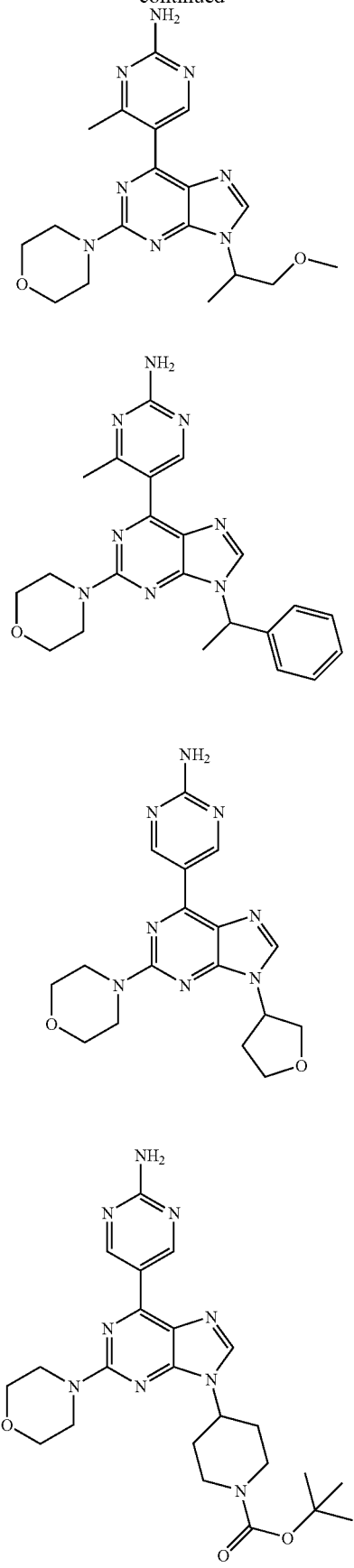

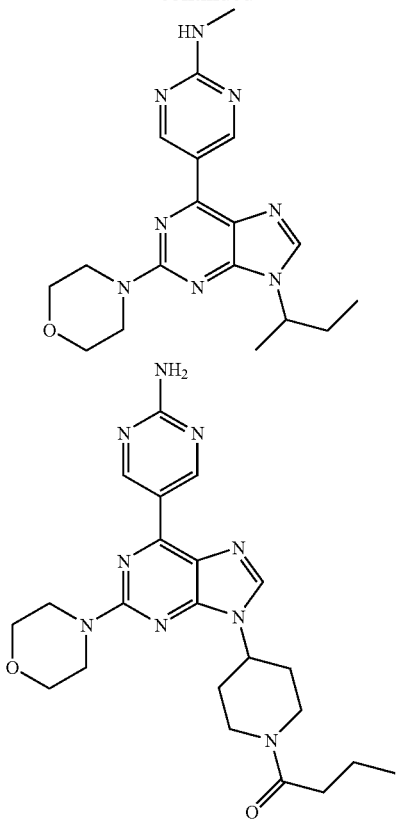
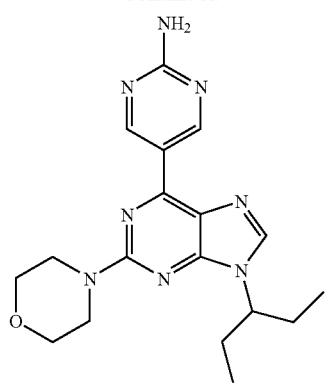
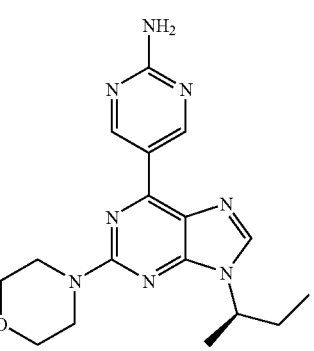
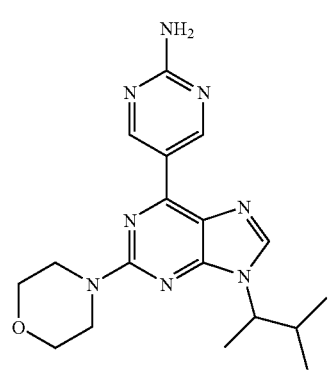
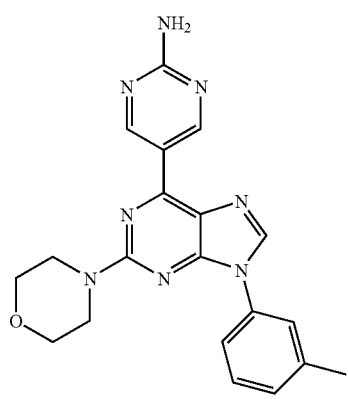

37
-continued
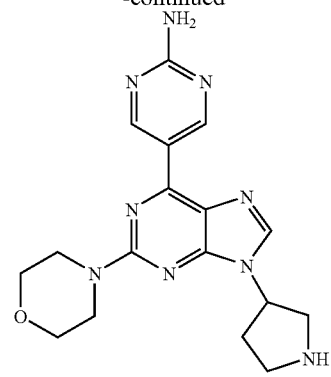
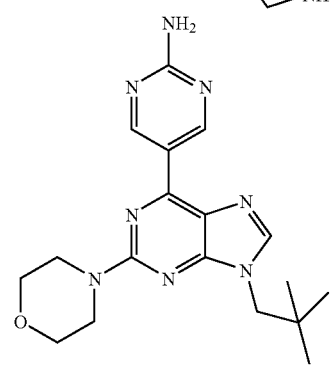
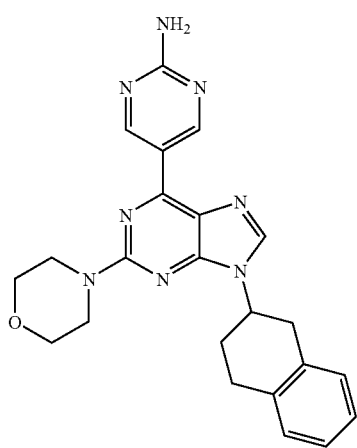
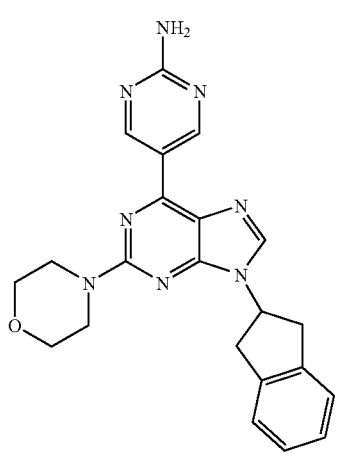
38
-continued
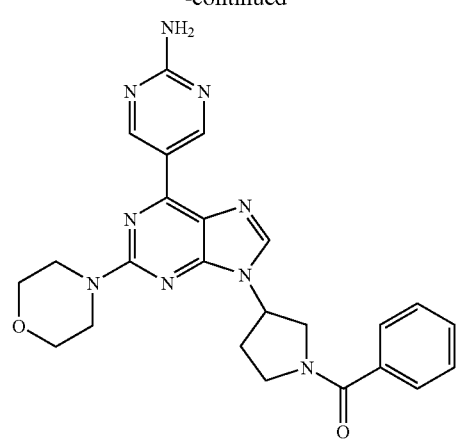
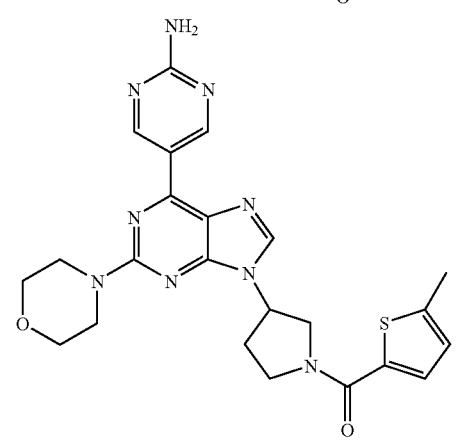
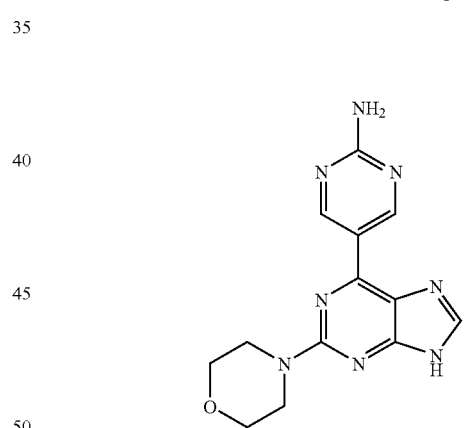
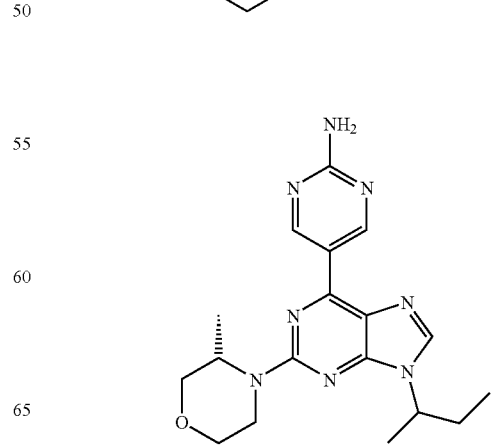

-continued

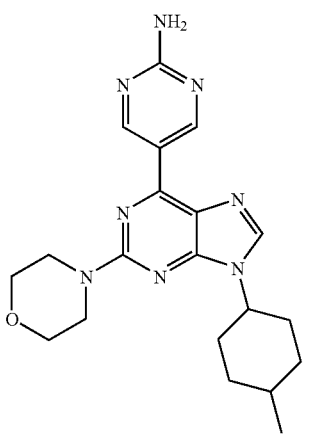

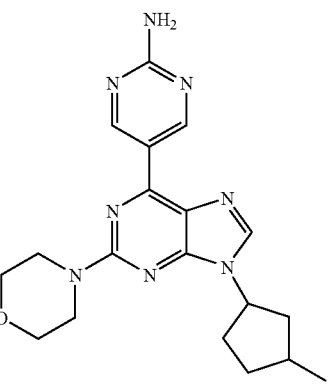

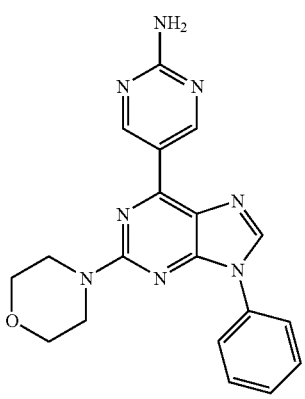

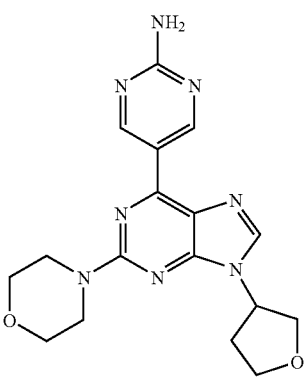

-continued

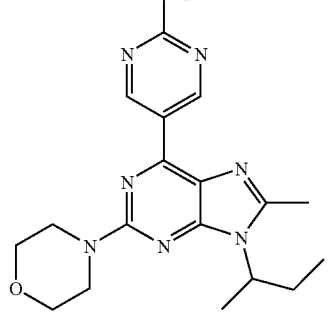

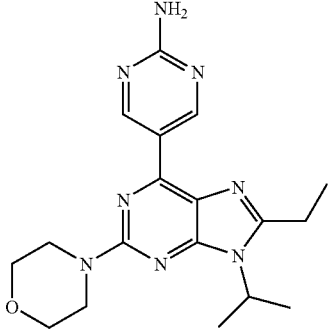

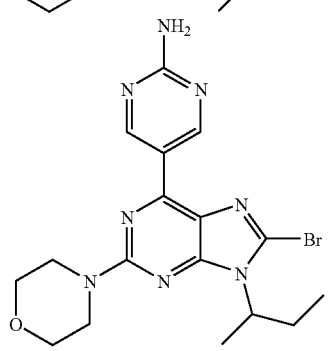

or a pharmaceutically acceptable salt or prodrug thereof.

The compounds of the invention have the ability to inhibit the activity of certain protein kinases. The ability to inhibit kinase activity may be a result of the compounds of the invention acting directly and solely on the kinase molecule to inhibit biological activity. However, it is understood that the compounds may also act at least partially on co-factors of the kinase in question that are involved in the phosphorylation process.

The compounds may have activity against PI3 protein kinases or a fragment or a complex or a functional equivalent thereof.

The compounds may have activity against certain serine/threonine kinases such as mTOR or a fragment or complex or functional equivalent thereof.

The inhibition of the protein kinase may be carried out in any of a number of well known ways in the art. For example if inhibition of the protein kinase in vitro is desired an appropriate amount of the compound of the invention may be added to a solution containing the kinase. In circumstances where it is desired to inhibit the activity of the kinase in a mammal the inhibition of the kinase typically involves administering the compound to a mammal containing the kinase.

Accordingly the compounds of the invention may find a multiple number of applications in which their ability to inhibit protein kinases of the type mentioned above can be utilised. For example the compounds may be used to inhibit serine/threonine protein kinases. The compounds may also be used in treating or preventing a condition in a mammal in which inhibition of a protein kinase and/or co-factor thereof prevents, inhibits or ameliorates a pathology or a symptomology of the condition.

The compounds disclosed have the ability to be used in the treatment of proliferative disorders. An example of such a disorder is cancer. It is anticipated that the compounds will have the ability to treat both solid and liquid tumors. In some embodiments the cancers that may be treated by compounds of the present invention include solid tumors and hematological cancers.

As used herein, the term "cancer" is a general term intended to encompass the vast number of conditions that are characterized by uncontrolled abnormal growth of cells. It is anticipated that the compounds of the invention will be useful in treating various cancers including but not limited to bone cancers, brain and CNS tumours, breast cancers, colorectal cancers, endocrine cancers including adrenocortical carcinoma, pancreatic cancer, pituitary cancer, thyroid cancer, parathyroid cancer, thymus cancer, gastrointestinal cancers, Liver cancer, extra hepatic bile duct cancer, gastrointestinal carcinoid tumour, gall bladder cancer, genitourinary cancers, gynaecological cancers, head and neck cancers, leukemias, myelomas, hematological disorders, lung cancers, lymphomas, eye cancers, skin cancers, soft tissue sarcomas, adult soft tissue sarcoma, Kaposi's sarcoma, urinary system cancers.

Exemplary cancers that may be treated by compounds of this invention include Hematologic cancer such as myeloproliferative disorders (idiopathic myelofibrosis, polycythemia vera, essential thrombocythemia, chronic myeloid leukemia), myeloid metaplasia, chronic myelomonocytic leukemia, acute lymphocytic leukemia, acute erythroblastic leukemia, Hodgkin's and Non Hodgkin's disease, B-cell lymphoma, acute T-cell leukemia, myelodysplastic syndromes, plasma cell disorder, hairy cell leukemia, kaposi's sarcoma, lymphoma and hyperproliferative conditions such as psoriasis and restenosis; gynaecologic cancer such as breast carcinoma, ovarian cancer, cervical cancer, vaginal and vulva cancer, endometrial hyperplasia; gastrointestinal tract cancer such as colorectal carcinoma, polyps, liver cancer, gastric cancer, pancreatic cancer, gall bladder cancer; urinary tract cancer such as prostate cancer, kidney and renal cancer; urinary bladder cancer, urethral cancer, penile cancer; skin cancer such as melanoma; brain tumour such as glioblastoma, neuroblastoma, astrocytoma, ependynoma, brain-stem gliomas, medulloblastoma, menigiomas, astrocytoma, oligodendroglioma; head and neck cancer such as nasopharyngeal carcinoma, laryngeal carcinoma; respiratory tract cancer such as lung carcinoma (NSCLC and SCLC), mesothelioma; eye disease such as retinoblastoma; musculo-skeleton diseases such as osteosarcoma, musculoskeleletal neoplasm; Squamous cell carcinoma and fibroid tumour. Compounds of this invention may also be used to treat pre-cancer conditions or hyperplasia including familial adenomatous polyposis, colonic adenomatous polyps, myeloid dysplasia, endometrial dysplasia, endometrial hyperplasia with atypia, cervical dysplasia, vaginal intraepithelial neoplasia, benign prostatic hyperplasia, papillomas of the larynx, actinic and solar keratosis, seborrheic keratosis and keratoacanthoma.

It is also anticipated that the compounds of the invention will be useful in treating autoimmune or inflammatory diseases or diseases supported by excessive neovascularisation. Diseases that have been attributed with some degree of autoimmune etiology, or that involve pathological inflammatory and neovascularization responses, include, but are not limited to, the following: acute disseminated encephalomyelitis, Addison's disease, agammaglobulinemia, agranulocytosis, allergic asthma, allergic encephalomyelitis, allergic rhinitis, alopecia areata, alopecia senilis, anerythroplasia, ankylosing spondylitis, antiphospholipid antibody syndrome, aortitis syndrome, aplastic anemia, atopic dermatitis, autoimmune haemolytic anemia, autoimmune hepatitis, autoimmune oophoritis, Balo disease, Basedow's disease, Behcet's disease, bronchial asthma, Castleman's syndrome, celiac disease, Chagas disease, chronic inflammatory demyelinating polyneuropathy, Churg-Strauss syndrome, Cogans syndrome, comical cornea, comical leukoma, Coxsackie myocarditis, CREST disease, Crohn's disease, cutaneous eosinophilia, cutaneous T-cell lymphoma, dermatitis erythrema multiforme, dermatomyositis, diabetic retinopathy, Dressler's syndrome, dystrophia epithelialis corneae, eczematous dermatitis, eosinophilic fasciitis, eosinophilic gastroenteritis, epidermolysis bullosa, Evans syndrome, fibrosing alveolitis, gestational pemphigoid, glomerulonephritis, Goodpasture's syndrome, graft-versus-host disease, Graves' disease, Guillain-Barre Syndrome, Hashimoto's disease, haemolytic-uretic syndrome, herpetic keratitis, ichthyosis vulgaris, idiopathic intersititial pneumonia, idiopathic thrombocytopenic purpura, inflammatory bowel diseases, Kawasaki's disease, keratitis, keratoconjunctivitis, Lambert-Eaton syndrome, leukoderma vulgaris, lichen planus, lichen sclerosus, Lyme disease, linear IgA disease, macular degeneration, megaloblastic anemia, Meniere's disease, Mooren's ulcer, Mucha-Habermann disease, multiple myositis, multiple sclerosis, myasthenia gravis, necrotizing enterocolitis, neuromyelitis optica, ocular pemphigus, opsoclonus myoclonus syndrome, Ord's thyroiditis, paroxysmal nocturnal hemoglobinuria, Parsonnage-Turner syndrome, pemphigus, periodontitis, pernicious anemia, pollen allergies, polyglandular autoimmune syndrome, posterior uveitis, primary biliary cirrhosis, proctitis, pseudomembranous colitis, psoriasis, pulmonary emphysema, pyoderma, Reiter's syndrome, reversible obstructive airway disease, rheumatic fever, rheumatoid arthritis, sarcoidosis, scleritis, Sezary's syndrome, Sjogren's syndrome, subacute bacterial endocarditis, systemic lupus erythematosus, Takayasu's arteritis, temporal arteritis, Tolosa-Hunt syndrome, Type I diabetes mellitus, ulcerative colitis, urticaria, vernal conjunctivitis, vitiligo, Vogy-Koyanagi-Harada syndrome and Wegener's granulomatosis.

The compounds of the invention may also be used the preparation of a medicament for treating a condition in an animal in which inhibition of a protein kinase can prevent, inhibit or ameliorate the pathology or symptomology of the condition. The compounds of the invention may also be used in the preparation of a medicament for the treatment or prevention of a kinase-related disorder.

Administration of compounds within Formula (I) to humans can be by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose. In various embodiments the inhibitor compound may be selectively toxic or more toxic to rapidly proliferating cells, e.g. cancerous tumours, than to normal cells.

In using the compounds of the invention they can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. We refer the reader to Remingtons Pharmaceutical Sciences, 19$^{th}$ edition, Mack Publishing Co. (1995) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. As such in some embodiments the present invention provides a pharmaceutical composition including a compound of Formula (I) and a pharmaceutically acceptable carrier, diluent or excipient. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found a container having a unit dosage of the agent (s). The kits can include a composition comprising an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The compounds of the invention may be used or administered in combination with one or more additional drug(s) for the treatment of the disorder/diseases mentioned. The components can be administered in the same formulation or in separate formulations. If administered in separate formulations the compounds of the invention may be administered sequentially or simultaneously with the other drug(s).

In addition to being able to be administered in combination with one or more additional drugs, the compounds of the invention may be used in a combination therapy. When this is done the compounds are typically administered in combination with each other. Thus one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, patches, sprays, ointments and inhalants. The active compound is mixed under sterile conditions with a pharmaceutically acceptable carrier and any needed preservatives, buffers, or propellants which may be required.

The amount of compound administered will preferably treat and reduce or alleviate the condition. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular compound administered, the mode of administration, the bioavailability of the preparation administered, the dose regime selected, the use of other medications and other relevant circumstances.

A preferred dosage will be a range from about 0.01 to 300 mg per kilogram of body weight per day. A more preferred dosage will be in the range from 0.1 to 100 mg per kilogram of body weight per day, more preferably from 0.2 to 80 mg per kilogram of body weight per day, even more preferably 0.2 to 50 mg per kilogram of body weight per day. A suitable dose can be administered in multiple sub-doses per day.

Synthesis of Compounds of the Invention

The agents of the various embodiments may be prepared using the reaction routes and synthesis schemes as described below, employing the techniques available in the art using starting materials that are readily available. The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, 3$^{rd}$ Edition, John Wiley & Sons, 1991. Alternatively, other reactions disclosed herein or known in the art will be recognized as having applicability for preparing other compounds of the various embodiments.

Reagents useful for synthesizing compounds may be obtained or prepared according to techniques known in the art.

General Synthetic Scheme

A wide range of trisubstituted purines can be prepared in a straightforward three step procedure starting from 2,6-dichloropurine which is commercially available from a number of sources or may be prepared from purine itself using, for example, phosphorylchloride. The general representative procedure is shown in scheme 1.

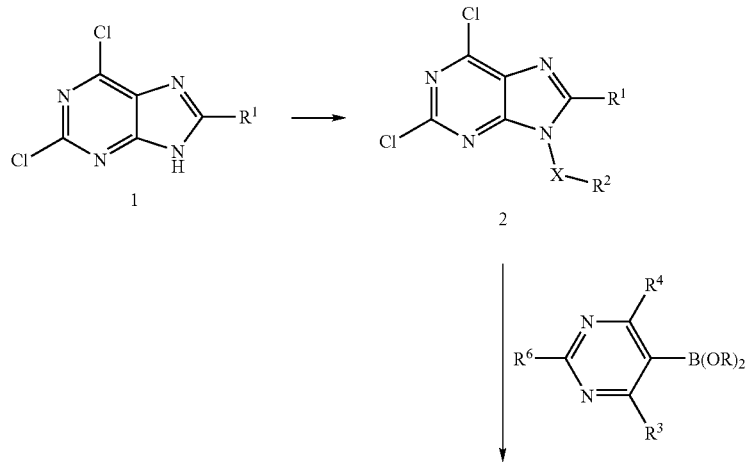

Scheme 1

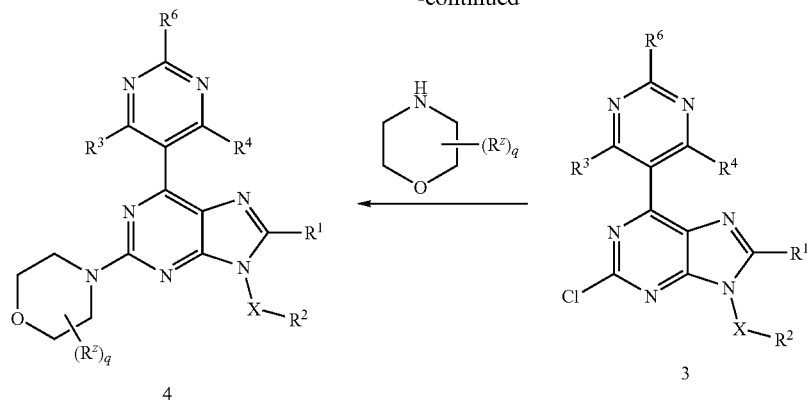

As shown initial reaction of 2,6-dichloropurine or its 8 derivative with an alkyl halide results in alkylation predominately at the 9 position (*Tetrahedron Letters* 1995, 36, 11, 1945). A typical procedure uses an alkyl bromide in the presence of a suitable base such as potassium carbonate. Alternatively, an alcohol may be reacted with the 2,6-dichloropurine in the presence of a phosphine and an activating agent, such as diethylazodicarboxylate, so as to effect a similar alkylation. N-arylation may also be carried out at the 9 position of the dichloropurine. Copper catalysed couplings of this type have been described by Gundersen et al. in *Tetrahedron Letters* 2003, 44, 3359-3362. Subsequent palladium catalysed coupling of 2 with a suitable aryl boronic acid or ester then delivers intermediate 3 (*Collect. Czech. Chem. Commun.* 2002, 67, 325). Addition of morpholine can then be carried out at elevated temperature, in a suitable solvent such as DMA, DMF or THF, to give the desired trisubstituted purine. In cases where a substituted morpholine group is being added the reaction has been shown to be facilitated by the use of microwave irradiation. The $R^1$ substituent may be varied either by using an 8-substituted dichloropurine as starting material (Scheme 1) or can be introduced later in the synthetic sequence (Scheme 2). For example chemistry may be carried out on the 8-position after completion of the sequence illustrated in scheme 1 above. For example, the 8-position of 4 may be brominated to give 5. The bromide may then be displaced by, for example, an organometallic agent, such as an organozinc, to install $R^1$ as in 6.

Scheme 2

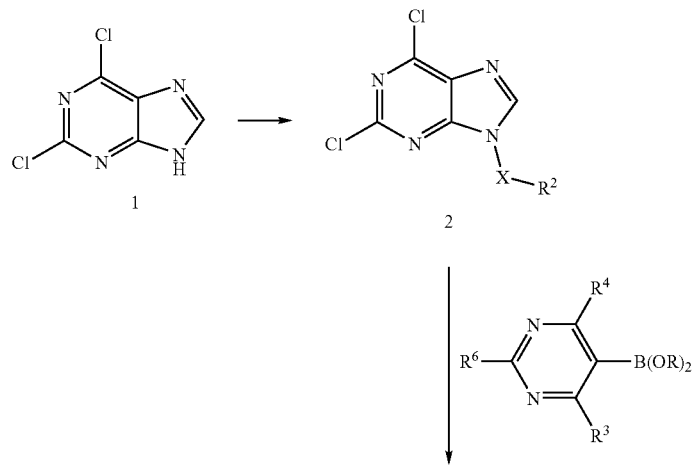

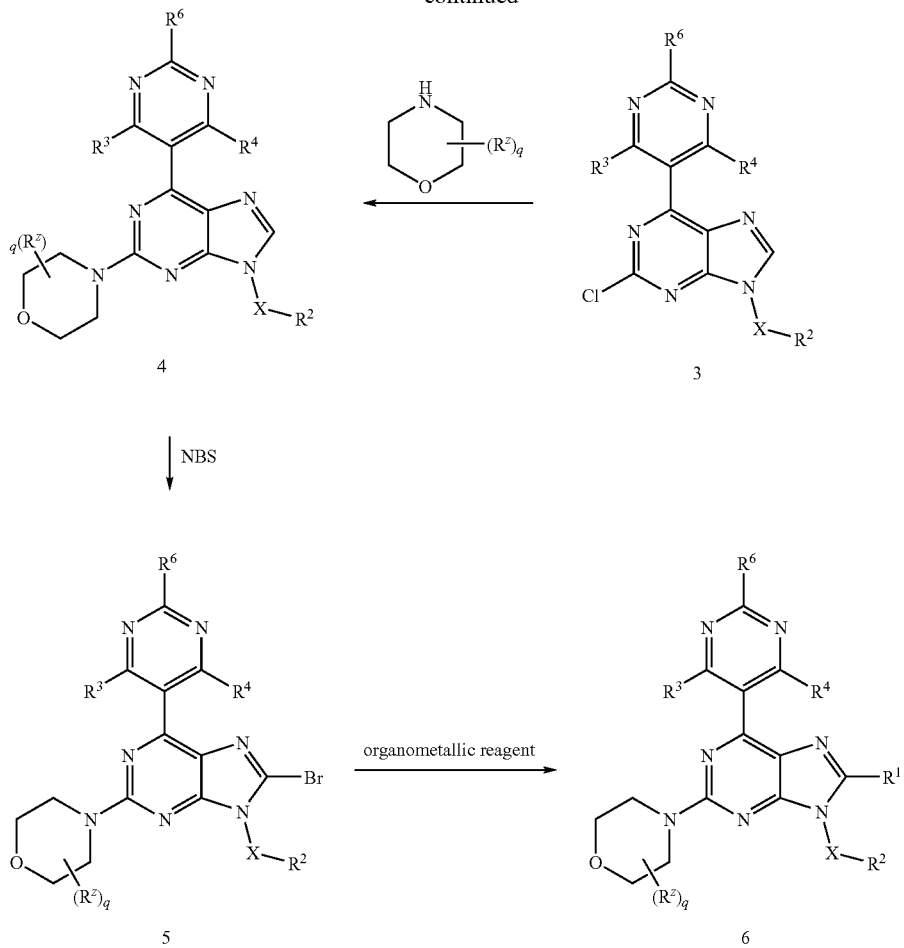

EXAMPLES

In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. Tetrahydrofuran (THF) and N,N-dimethylformamide (DMF) were purchased from Aldrich in SureSeal bottles and used as received. All solvents were purified by using standard methods in the art, unless otherwise indicated.

The reactions set forth below were performed under a positive pressure of nitrogen, argon or with a drying tube, at ambient temperature (unless otherwise stated), in anhydrous solvents, and the reaction flasks are fitted with rubber septa for the introduction of substrates and reagents via syringe. Glassware was oven-dried and/or heat-dried. Analytical thin-layer chromatography was performed on glass-backed silica gel 60 F 254 plates (E Merck (0.25 mm)) and eluted with the appropriate solvent ratios (v/v). The reactions were assayed by TLC and terminated as judged by the consumption of starting material.

The TLC plates were visualized by UV absorption or with a p-anisaldehyde spray reagent or a phosphomolybdic acid reagent (Aldrich Chemical, 20 wt % in ethanol) which was activated with heat, or by staining in an iodine chamber.

Work-ups were typically done by doubling the reaction volume with the reaction solvent or extraction solvent and then washing with the indicated aqueous solutions using 25% by volume of the extraction volume (unless otherwise indicated). Product solutions were dried over anhydrous sodium sulfate prior to filtration, and evaporation of the solvents was under reduced pressure on a rotary evaporator and noted as solvents removed in vacuo.

Flash column chromatography [Still et al, J. Org. Chem., 43, 2923 (1978)] was conducted using E Merck-grade flash silica gel (47-61 mm) and a silica gel:crude material ratio of about 20:1 to 50:1, unless otherwise stated. Hydrogenolysis was done at the pressure indicated or at ambient pressure.

$^1$H NMR spectra were recorded on a Bruker instrument operating at 400 MHz, and $^{13}$C-NMR spectra was recorded operating at 100 MHz. NMR spectra were obtained as CDCl$_3$ solutions (reported in ppm), using chloroform as the reference standard (7.27 ppm and 77.00 ppm) or CD$_3$OD (3.4 and 4.8 ppm and 49.3 ppm), or an internal tetramethylsilane standard (0.00 ppm) when appropriate. Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz. Mass spectra were obtained using LC/MS either in ESI or APCI. All melting points are uncorrected. All final products had greater than 90% purity (by HPLC at wavelengths of 220 nm and 254 nm).

The following examples are intended to illustrate the embodiments disclosed and are not to be construed as being limitations thereto. Additional compounds, other than those described below, may be prepared using the following described reaction scheme or appropriate variations or modifications thereof.

Scheme 3 depicts three variations on the three step procedure in which different conditions are used in the first step so as to introduce diverse substituents at the 9-position of the purine scaffold. In principle, however, a skilled addressee could modify the general reaction scheme shown in scheme one where the nitrogen moiety at the 9 position of the purine may be reacted with a moiety containing a suitable leaving group (such as a halide) in a reaction whereby the nitrogen displaces the leaving group to form the compound in which the nitrogen at the 9 position is then functionalised with the moiety. Suitable leaving groups for use in reactions of this type which can be displaced by nitrogen in such reactions are known in the art and in general the synthesis of moieties containing leaving groups of this type for use in these types of reactions are also well known to a skilled worker in the field.

As shown in Scheme 3 the three simplest routes to the compounds of the invention involve reaction of the dichloropurine with either an arylalkyl halide (such as benzyl halide) or a heteroarylalkyl halide to introduce an aryl or heteroaryl substituted methyl group at the 9 position, an alcohol (to introduce a di-substituted methyl group at the 9 position) or an aryl or heteroaryl boronic acid (to introduce an aryl or heteroaryl group directly.

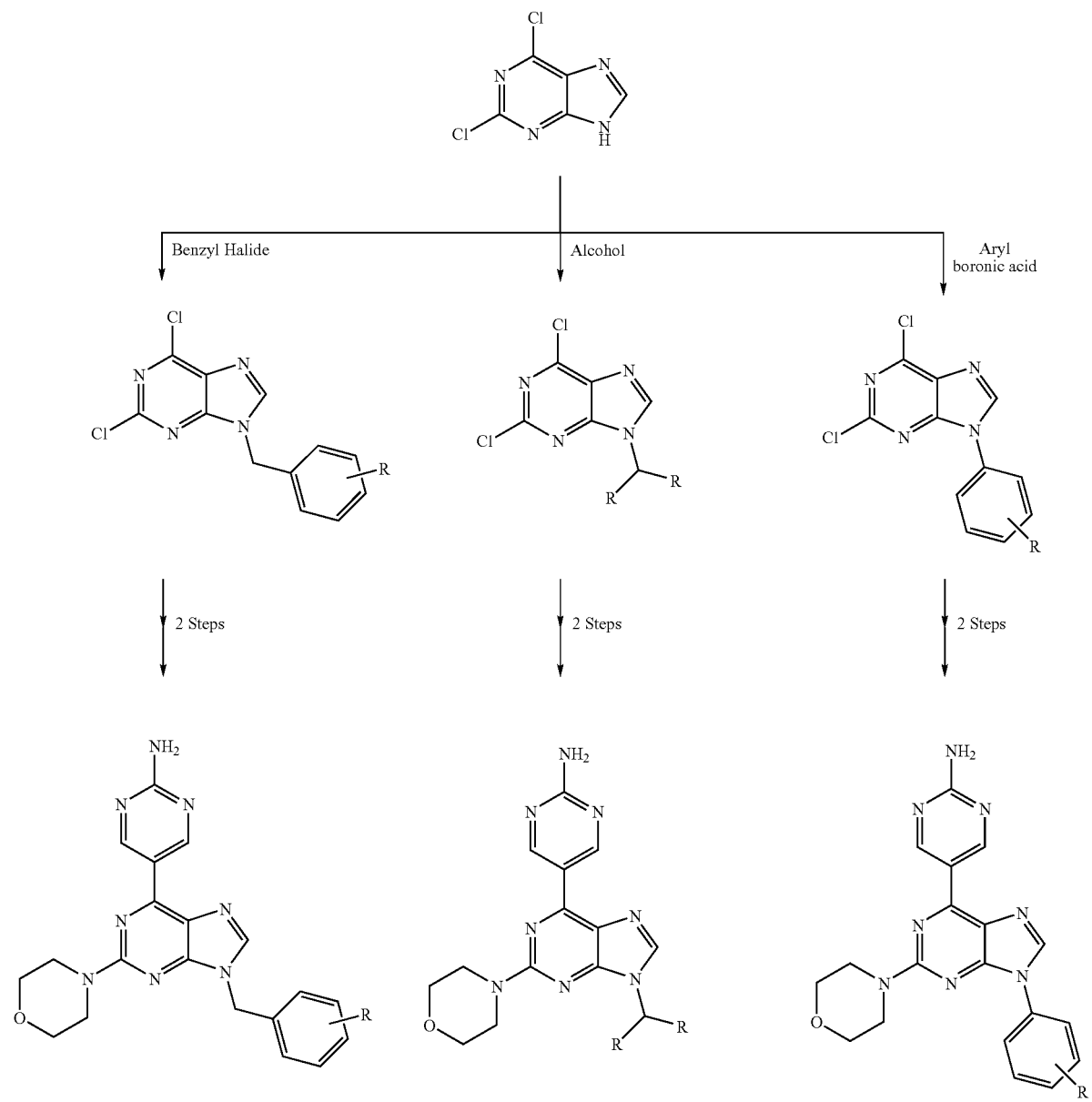

Example 1

Compound 1

Synthesis of 2,6-Dichloro-9-(2,6-difluoro-benzyl)-9H-purine

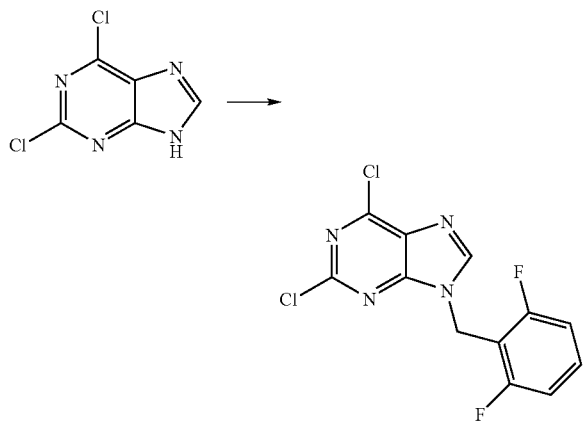

To a stirred solution of 2,6-dichloropurine (5.3 mmol) in 10 ml anhydrous DMSO at room temperature was added anhydrous potassium carbonate (6.34 mmol) and 2,6-difluorobenzylbromide (6.34 mmol). The reaction mixture was maintained at this temperature for 20 hrs. The reaction can be monitored using either TLC or LC/MS. The reaction mixture was poured in to a beaker containing ice-cold water. The aqueous layer was acidified to pH 5-6. Extraction of the aqueous layer, using 3×75 ml portions of ethyl acetate, afforded the crude product. This was purified on the silica gel column (10-70% ethyl acetate in petroleum ether, step-gradient), to give the desired compound in a yield of 61%.

Synthesis of 5-[2-chloro-(2,6-difluoro-benzyl)-9H-purin-6-yl]-pyrimidin-2-ylamine

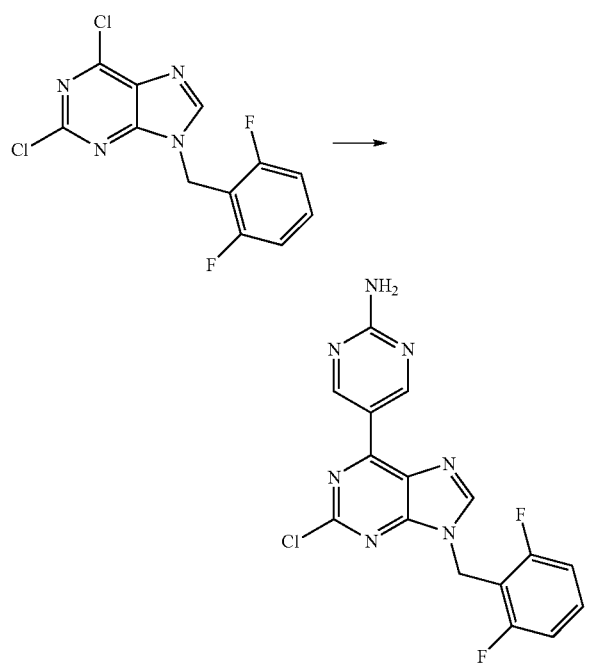

A solution of 2,6-dichloro-9-(2,6-difluoro-benzyl)-9H-purine (1.59 mmol), 5-(4,4,5,5-tetremethyl-[1,3,2]dioxaborolan-2-ylamine (1.59 mmol) and 1,1'-bis(diphenylphosphino)ferrocene palladium (II) chloride, complexed with dichloromethane (0.15 mmol), was taken up in a mixture of peroxide free dioxane (40 ml) and added 2M aqueous solution of sodium carbonate (6.4 mmol). The reaction mix was degassed and purged with nitrogen. This reaction mix was then stirred on an oil bath maintained at 65° C. for 3 h. The reaction was monitored by LC/MS for the disappearance of the starting purine.

The reaction mixture was cooled to room temperature and the solvents removed under reduced pressure. The residue was taken up in ethyl acetate and water. The organic phase was separated and the aqueous layer further extracted with 3×100 ml portions of ethyl acetate. The combined ethyl acetate layers were washed once with brine solution (25 ml). The organics were dried over sodium sulfate and the solvents removed under vacuum to give 5-[2-chloro-(2,6-difluoro-benzyl)-9H-purin-6-yl]-pyrimidin-2-ylamine in 60% yield.

Synthesis of 5-[2-chloro-(2,6-difluoro-benzyl)-2-morpholin-4-yl-9H-purin-6-yl]-pyrimidin-2-ylamine

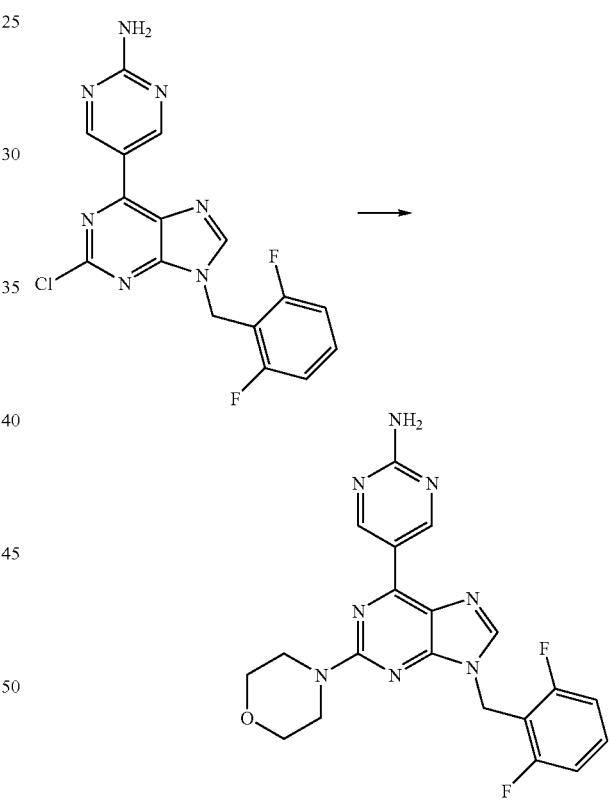

To a solution of 5-[2-chloro-(2,6-difluoro-benzyl)-9H-purin-6-yl]-pyrimidin-2-ylamine (1.12 mmol) in dimethyl acetamide (18 ml) was added morpholine (3.5 mmol). The reaction mix was heated on an oil bath maintained at 94° C. for 12 h. The reaction was monitored for the absence of the 5-[2-chloro-(2,6-difluoro-benzyl)-9H-purin-6-yl]-pyrimidin-2-ylamine, by LC-MS. The crude material was directly loaded onto a preparative HPLC column and purified by chromatography to get the title compound in a yield of 70%.

$^1$H NMR, DMSO: 9.48 (s, 2H); 8.29 (s, 1H); 7.45 (m, 2H); 7.31 (s, 2H); 7.14 (t, 1H); 5.42 (s, 2H); 3.75 (m, 4H); 3.67 (m, 4H). m/z: 425.27 [MH]$^+$.

Example 2

Compound 2

Synthesis of 9-sec-butyl-2,6-dichloro-9H-purine

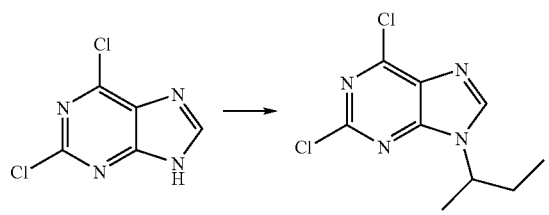

2,6-dichloropurine (5.3 mmol), 2-Butanol (9.01 mmol), triphenylphosphine (7.95 mmol) in 40 ml anhydrous tetrahydrofuran, to which was added drop-wise diisoproplyazidodicarboxylate (7.95 mmol) at room temperature over a period of 30 minutes. The reaction mixture was stirred at room temperature for 24 hrs. The reaction is monitored by TLC or LC/MS. The reaction mixture was poured in to a beaker containing ice-cold water. Extraction of the aqueous layer, using 3×100 ml portions of ethyl acetate, afforded the crude product. This was purified on the silica gel column (10-80% ethyl acetate in petroleum ether, gradient elution), to give the desired compound in a yield of 50%.

Synthesis of 5-(9-sec-butyl-2-chloro-9H-purin-6-yl)-pyrimidin-2-ylamine

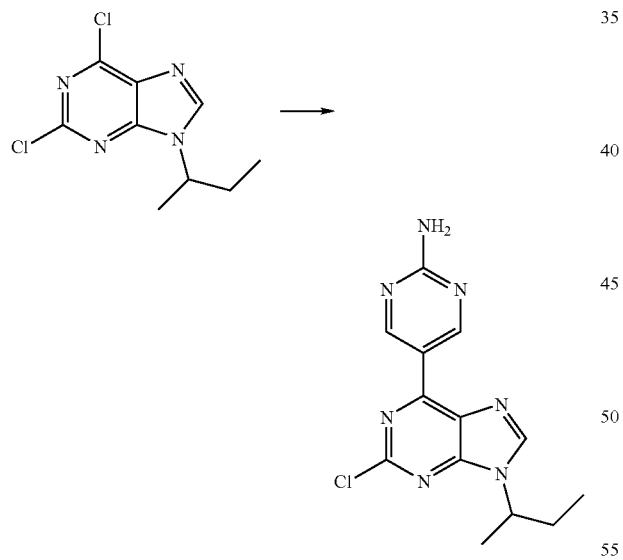

A solution of 9-sec-butyl-2,6-dichloro-9H-purine (1.59 mmol), 5-(4,4,5,5-tetremethyl-[1,3,2]dioxaborolan-2-ylamine (1.59 mmol) and 1,1'-bis(diphenylphosphino) ferrocene palladium (II) chloride, complexed with dichloromethane (0.15 mmol) were taken up in a mixture of peroxide free dioxane (40 ml) and added 2M aqueous solution of sodium carbonate (6.4 mmol). The reaction mix was degassed and purged with nitrogen. This reaction mix was then stirred on an oil bath maintained at 80° C. for 3 h. The reaction was monitored by LC/MS for the disappearance of the starting purine.

The reaction mixture was cooled to room temperature and the solvents removed under reduced pressure. The residue was taken up in ethyl acetate and water. The organic phase was separated and the aqueous layer further extracted with 3×100 ml portions of ethyl acetate. The organics were dried over sodium sulfate and the solvents removed under vacuum to give 5-(9-sec-butyl-2-chloro-9H-purin-6-yl)-pyrimidin-2-ylamine in 60% yield.

Synthesis of 5-(9-sec-butyl-2-morpholin-4-yl-9H-purin-6-yl)-pyrimidin-2-ylamine

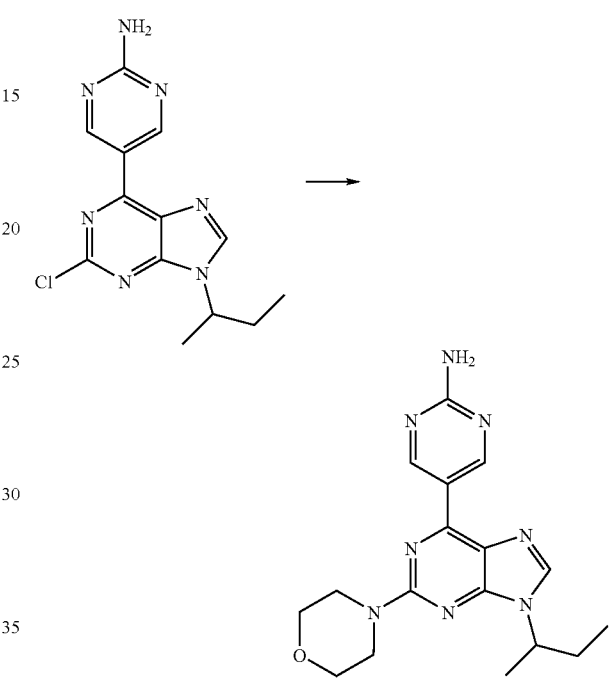

To a solution of 5-(9-sec-butyl-2-chloro-9H-purin-6-yl)-pyrimidin-2-ylamine (1.12 mmol) in dimethyl acetamide (18 ml) was added morpholine (3.5 mmol). The reaction mix was heated on an oil bath maintained at 94° C. for 12 h. The reaction was monitored for the absence of the give 5-(9-sec-butyl-2-chloro-9H-purin-6-yl)-pyrimidin-2-ylamine, by LC-MS. The crude material was directly loaded onto a preparative HPLC column and purified by chromatography to get the title compound in a yield of 70%. $^1$H NMR, DMSO-d6: 9.52 (s, 2H); 8.27 (s, 1H); 7.28 (s, 2H); 4.5 (m, 2H); 3.8 (m, 4H); 3.70 (m, 4H); 2.0 (m, 1H); 1.9 (m, 1H); 1.6 (d, 3H); 0.79 (t, 3H). m/z: 355.45 [MH]$^+$.

Example 3

Compound 27

Synthesis of 2,6-Dichloro-9-m-tolyl-9H-purine

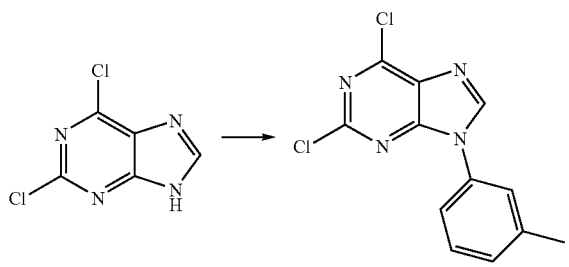

2,6-Dichloropurine (1.3 mmol), m-Tolyl boronic acid (4.0 mmol), anhydrous cupric acetate (1.32 mmol), 4 Å molecular sieves (1 g) [1,10]-Phenanthroline (2.64 mmol) in 25 ml of anhydrous dichloromethane were stirred at room temperature in a round bottomed flask. The reaction mixture was stirred at room temperature and monitored by TLC, LC-MS. Reaction was complete after 24 h. The molecular sieves and inorganic material were removed by filtration through a celite bed. The bed was thoroughly washed with methanol. The combined organics were purified by flash chromatography to yield 50% of the desired compound as a solid. m/z: 279.02 [MH]$^+$.

Synthesis of 5-(2-chloro-9-m-tolyl-9H-purin-6-yl)-pyrimidin-2-yl-amine

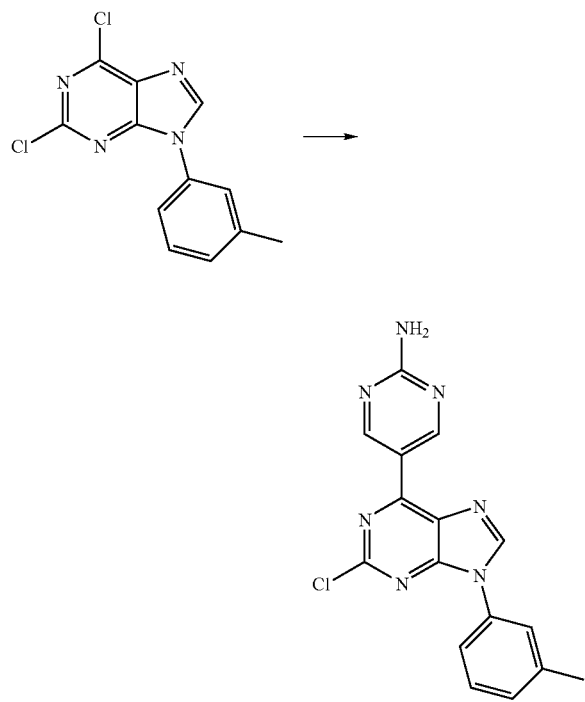

2,6-Dichloro-9-m-tolyl-9H-purine (0.182 mmol), 5-(4,4,5,5-tetremethyl-[1,3,2]dioxaborolan-2-ylamine (0.182 mmol) and 1,1'-bis(diphenylphosphino) ferrocene palladium (II) chloride, complexed with dichloromethane (0.018 mmol) were taken up in a mixture of peroxide free dioxane (40 ml) and added 2M aqueous solution of sodium carbonate (0.730 mmol). The reaction mix was degassed and purged with nitrogen. This reaction mix was then stirred on an oil bath maintained at 40° C. for 2 h. The reaction was monitored by LC/MS for the disappearance of the starting purine. The reaction mixture was cooled to room temperature and the solvents removed under reduced pressure. The residue was taken up in ethyl acetate and water. The organic phase was separated and the aqueous layer further extracted with 3×100 ml portions of ethyl acetate. The organics were dried over sodium sulfate and the solvents removed under vacuum to give 5-(2-chloro-9-m-tolyl-9H-purin-6-yl)-pyrimidin-2-yl-amine. This crude material was taken directly to the next step without further purification.

Synthesis of 5-(2-morpholin-4-yl-9-m-tolyl-9H-purin-6-yl)-pyrimidin-2-yl-amine

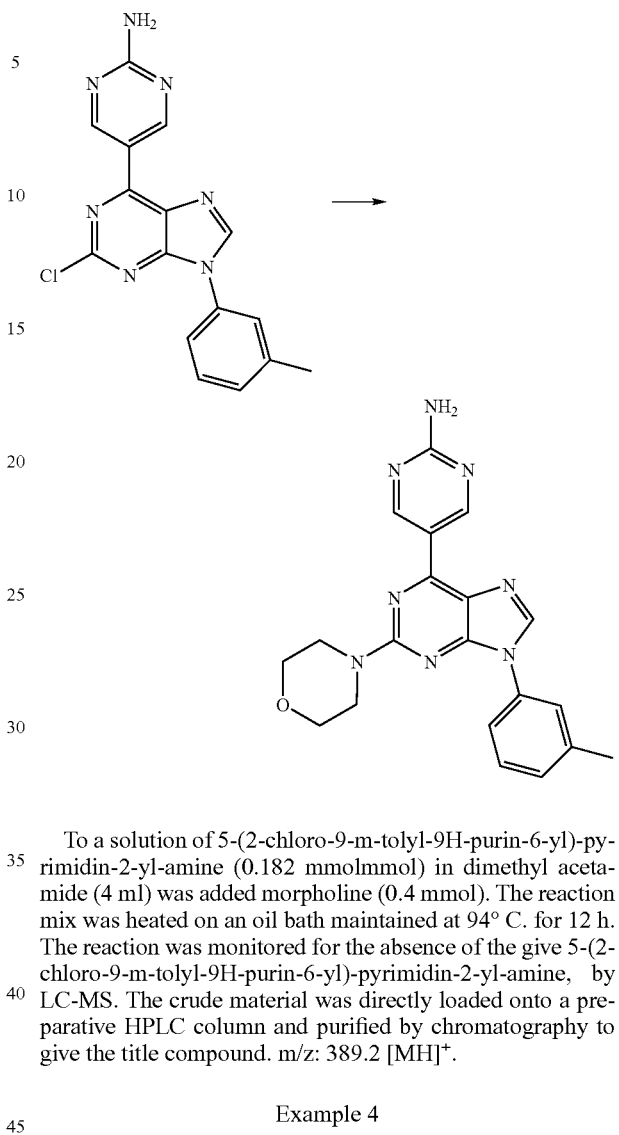

To a solution of 5-(2-chloro-9-m-tolyl-9H-purin-6-yl)-pyrimidin-2-yl-amine (0.182 mmolmmol) in dimethyl acetamide (4 ml) was added morpholine (0.4 mmol). The reaction mix was heated on an oil bath maintained at 94° C. for 12 h. The reaction was monitored for the absence of the give 5-(2-chloro-9-m-tolyl-9H-purin-6-yl)-pyrimidin-2-yl-amine, by LC-MS. The crude material was directly loaded onto a preparative HPLC column and purified by chromatography to give the title compound. m/z: 389.2 [MH]$^+$.

Example 4

Compound 33

Synthesis of {3-[6-(2-Amino-pyrimidin-5-yl)-2-morpholin-4-yl-purin-9-yl]-pyrrolidin-1-yl}-(5-methyl-thiophen-2-yl)-methanone

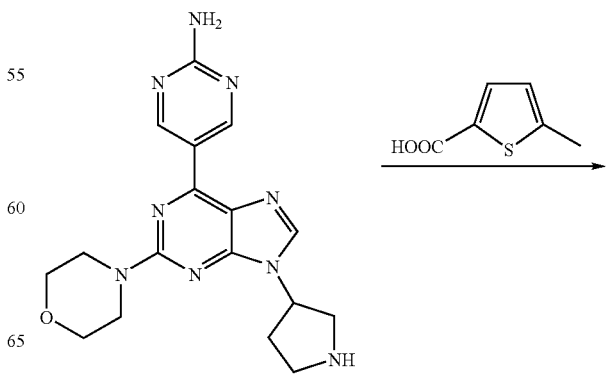

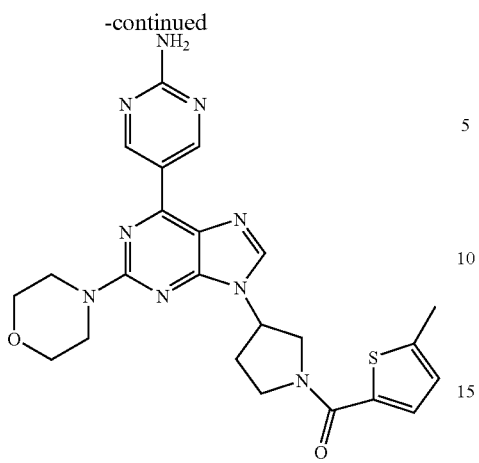

{3-[6-(2-Amino-pyrimidin-5-yl)-2-morpholin-4-yl-purin-9-yl]-pyrrolidin-1-yl}-(5-methyl-thiophen-2-yl)-methanone was prepared from the corresponding Boc protected compound (3-[6-(2-amino-pyrimidin-5-yl)-2-morpholin-4-yl-purin-9-yl]-pyrrolidine-1-carboxylic acid tert-butyl ester) using a standard deprotection protocol. This intermediate was in turn prepared using the same three step procedure employed in the synthesis of 5-(9-sec-butyl-2-morpholin-4-yl-9H-purin-6-yl)-pyrimidin-2-ylamine (compound 2) starting from the commercially available Boc protected aminoalcohol 3-hydroxy-pyrrolidine-1-carboxylic acid tert-butyl ester.

To a solution of 5-(2-morpholin-4-yl-9-pyrrolidin-3-yl-9H-purin-6-yl)-pyrimidin-2-ylamine (37 mg, 0.08 mmol) in DMF was added 5-methyl-thiophene-2-carboxylic acid (15 mg, 0.104 mmol, 1.3 eq), EDC (20 mg, 0.104 mmol, 1.3 eq), HOBt (14 mg, 0.104 mmol, 1.3 eq) and diisopropylethylamine (32 μL, 0.184 mmol, 2.3 eq). The mixture was stirred at 50° C. for 16 hrs. Then NaHCO₃ was added and the mixture extracted twice with ethyl acetate. The combined organic layers were further washed with brine before drying over Na₂SO₄. The crude product was purified by chromatography to afford the title compound as yellow solid (14.4 mg).
¹H NMR, CDCl₃: 9.74 (2H, s), 7.80 (1H, s), 7.39 (3H, s), 6.77 (1H, d, J=3.3), 5.19-5.13 (1H, m), 4.33 (1H, b s), 4.24-4.19 (1H, m), 4.09-4.04 (1H, m), 4.00 (1H, b s), 3.87-3.79 (8H, m), 2.61-2.56 (2H, m), 2.52 (3H, s). m/z: 492 [MH]⁺.

Example 5

Compound 40

Synthesis of 5-(8-Bromo-9-sec-butyl-2-morpholin-4-yl-9H-purin-6-yl)-pyrimidin-2-ylamine

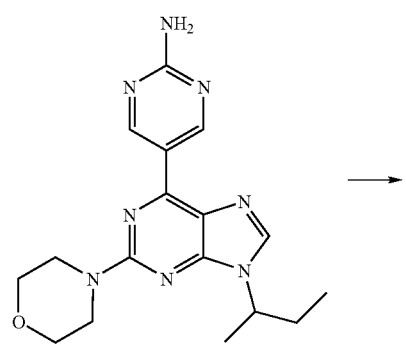

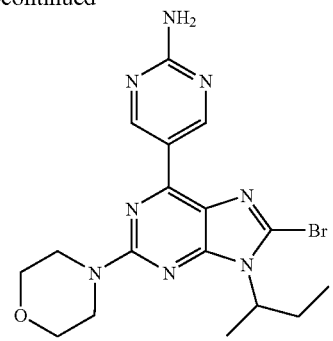

To a solution of 5-(9-sec-Butyl-2-morpholin-4-yl-9H-purin-6-yl)-pyrimidin-2-ylamine, (200 mg, 0.57 mmol) in 15 ml of chloroform, was added slowly NBS, (120 mg, 0.68 mmol) at a temperature of 5° C. The reaction was continued for 2 hours at this temperature. After simple work-up, the product 5-(8-Bromo-9-sec-butyl-2-morpholin-4-yl-9H-purin-6-yl)-pyrimidin-2-ylamine was purified by flash column (solvent system: 50% ethyl acetate in hexane) to deliver the desired compound in a yield of 49% (120 mg).

Synthesis of 5-(9-sec-Butyl-8-methyl-2-morpholin-4-yl-9H-purin-6-yl)-pyrimidin-2-ylamine

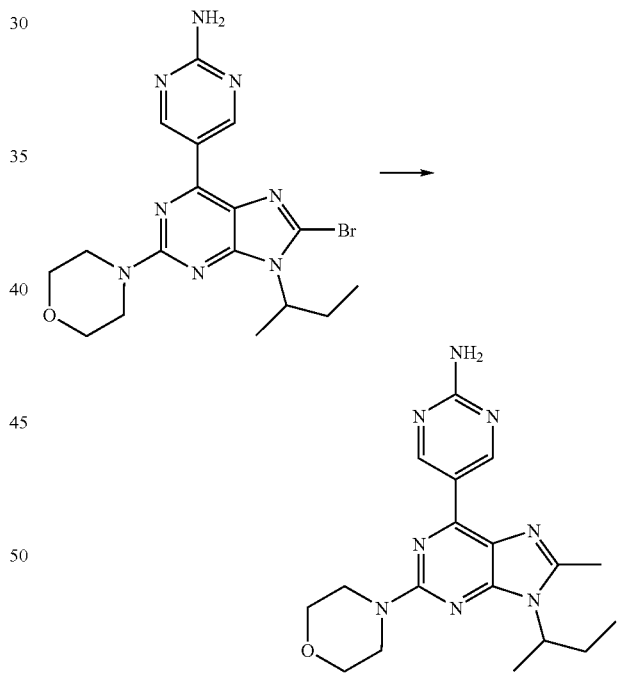

To a solution of 5-(8-Bromo-9-sec-butyl-2-morpholin-4-yl-9H-purin-6-yl)-pyrimidin-2-ylamine, (20 mg, 0.046 mmol), Pd(dppf)Cl₂, (3 mg, 8% mmol) in 3 ml of anhydrous dioxane, was added slowly dimethyl zinc (230 μl, 1.0M in heptane solution). The mixture was heated to about 65° C. until in the sealed tube. MeOH was added dropwise and solvents were removed in vacuo. EtOAc was added to the residue and the resulting solution washed with 1 M HCl, water, brine and then dried over Na₂SO₄. The solvent was removed and the crude mixture was subjected to flash chromatography to obtain 5-(9-sec-Butyl-8-methyl-2-morpholin-4-yl-9H-purin-6-yl)-pyrimidin-2-ylamine 8 mg in a yield of 47%. ¹H NMR, MeOD: 9.45 (s, 2H); 4.55 (m, 1H); 3.87 (m, 4H); 3.80 (s, 4H); 2.69 (s, 3H); 2.43 (m, 1H); 2.02 (m, 1H); 1.71 (d, 3H); 0.86 (t, 3H). m/z: 369.22 [MH]⁺.

The compounds outlined in Table 1 were synthesized following the procedures outlined above or variations thereof typically by variation of the starting materials used.

TABLE 1

Synthesised compounds

| Cmpd No | Structure | 1H-NMR | MS (M + 1) |
|---|---|---|---|
| 1 | 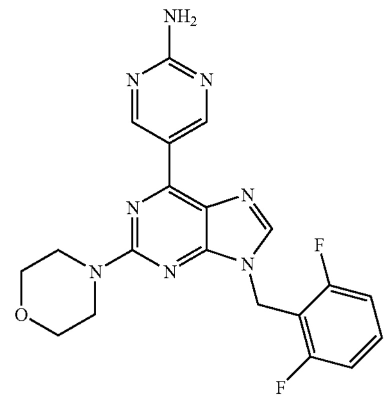 | (DMSO-d6) δ 9.48(s, 2H); 8.29(s, 1H); 7.45(m, 2H); 7.31(s, 2H); 7.14(t, 1H); 5.42(s, 2H); 3.75(m, 4H); 3.67(m, 4H). | 425.27 |
| 2 | 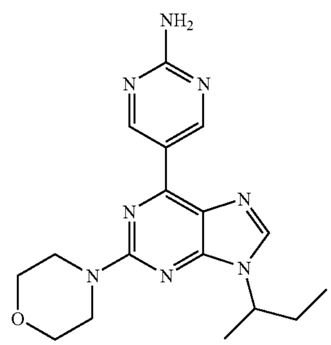 | (DMSO-d6) δ 9.52(s, 2H); 8.27(s, 1H); 7.28(s, 2H); 4.5(m, 2H); 3.8(m, 4H); 3.70(m, 4H); 2.0(m, 1H); 1.9(m, 1H); 1.6(d, 3H); 0.79(t, 3H). | 355.45 |
| 3 | 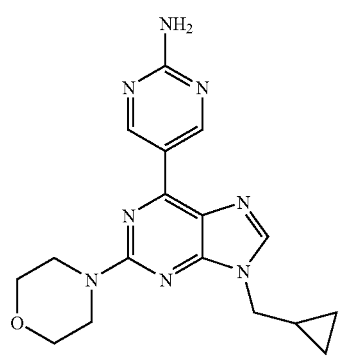 | (DMSO-d6) δ 9.52(s, 2H); 8.27(s, 1H); 7.28(s, 2H); 4.01(m, 2H); 3.8(m, 4H); 3.70(m, 4H); 1.3(m, 1H); 0.54(m, 2H); 0.52(m, 2H). | 353.40 |
| 4 | 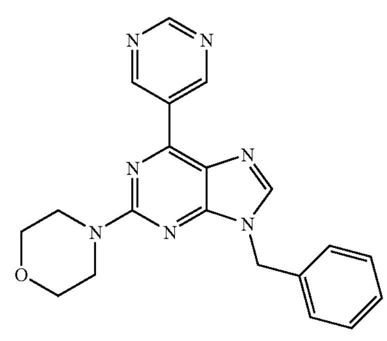 | (CDCl₃) δ 10.0(s, 2H); 9.4(s, 1H); 7.9(s, 1H); 7.45-7.35(m, 5H); 5.4(s, 2H); 3.9(m, 4H); 3.8(m, 4H). | 374.32 |

TABLE 1-continued

Synthesised compounds

| Cmpd No | Structure | 1H-NMR | MS (M + 1) |
|---|---|---|---|
| 5 | 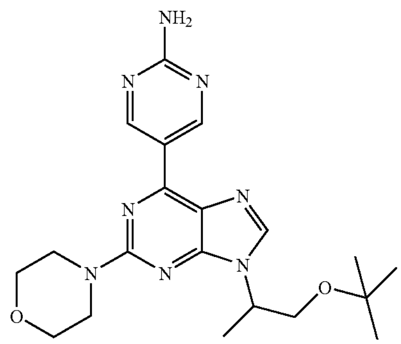 | (DMSO-d6) δ 9.54(s, 2H); 8.27(s, 1H); 7.28(s, 2H); 4.6(m, 2H); 3.8(m, 4H); 3.70(m, 4H); 3.65(m, 2H); 1.55(d, 3H); 0.9 (s, 9 H). | 413.41 |
| 6 | 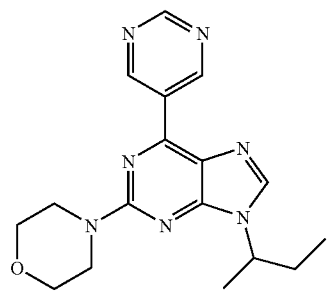 | (DMSO-d6) δ 9.97(s, 2H); 9.34(s, 1H); 8.50(s, 1H); 4.5(m, 1H); 3.9(m, 4H); 3.8(m, 4H); 2.0(m, 1H); 1.9(m, 1H); 1.6(d, 3H); 0.79(t, 3H). | 340.50 |
| 7 | 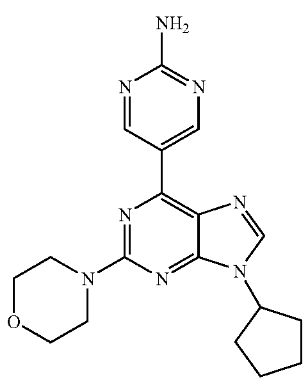 | (MeOD) δ 9.28(s, 2H), 8.08(s, 1H), 5.03(m, 1H), 4.34(m, 4H), 3.85(m, 4H), 2.30(m, 2H), 2.03 (m, 4H), 1.85(m, 2H). | 367 |
| 8 | 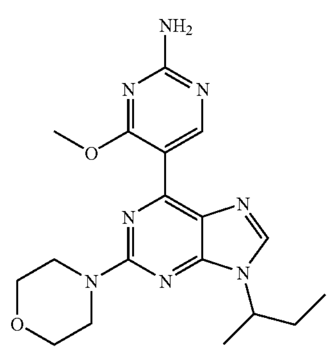 | (DMSO-d6) δ 8.74(s, 1H); 8.4(s, 1H); 7.6(bs, 2H); 4.5(m, 1H); 4.0(s, 3H); 3.8(m, 4H); 3.7(m, 4H); 2.0(m, 1H); 1.9(m, 1H); 1.6(d, 3H); 0.79(t, 3H). | 385.46 |

TABLE 1-continued
Synthesised compounds
| Cmpd No | Structure | 1H-NMR | MS (M + 1) |
|---|---|---|---|
| 9 | 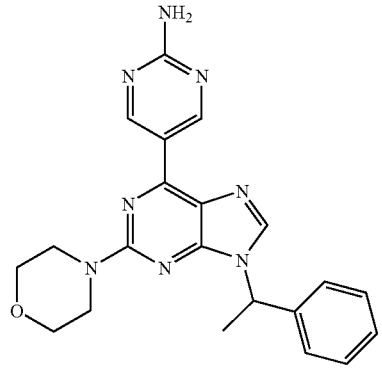 | (DMSO-d6) δ 9.54(s, 2H); 8.45(s, 1H); 7.42-7.22(m, 5H); 5.8(m, 1H); 3.8(m, 4H); 3.7(m, 4H); 2.0(d, 3H). | 403.39 |
| 10 | 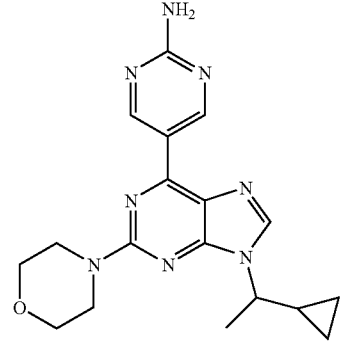 | (DMSO-d6) δ 9.53(s, 2H); 8.35(s, 1H); 7.28(s, 2H); 3.86(m, 1H); 3.78(m, 4H); 3.72(m, 4H); 1.62(d, 3H); 1.5(m, 1H); 0.7(m, 1H); 0.5(m, 2H); 0.4(m, 1H). | 367.46 |
| 11 | 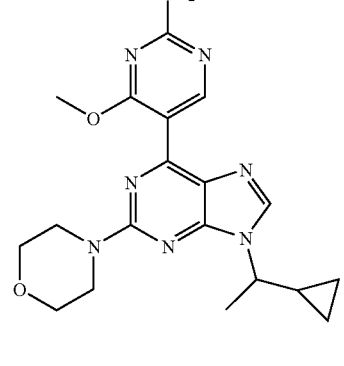 | (DMSO-d6) δ 8.73(s, 1H); 8.5(s, 1H); 7.28(s, 2H); 4.0(s, 3H); 3.86(m, 1H); 3.78(m, 4H); 3.72(m, 4H); 1.62(d, 3H); 1.5(m, 1H); 0.7(m, 1H); 0.5(m, 2H); 0.4(m, 1H). | 397.41 |
| 12 | 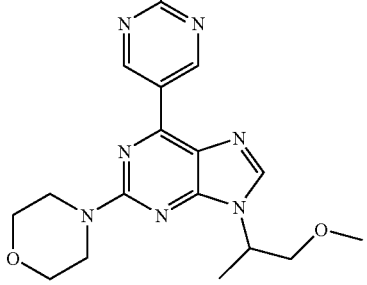 | (DMSO-$d_6$) δ 9.53(s, 2H), 8.26(s, 1H), 4.81(m, 1H), 3.84(m, 4H), 3.71(m, 4H), 3.62(m, 2H), 3.23(s, 3H), 1.50(d, 3H). | 371 |

TABLE 1-continued

Synthesised compounds

| Cmpd No | Structure | 1H-NMR | MS (M + 1) |
|---|---|---|---|
| 13 | 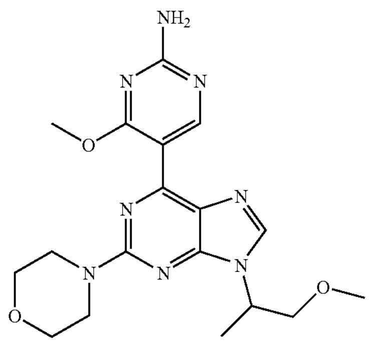 | (DMSO-d6) δ 8.72(s, 1H); 8.34(s, 1H); 7.66(bs, 2H); 4.8(m, 1H); 4.0(s, 3H); 3.9(m, 1H); 3.8-3.7(m, 8 H); 3.6(m, 1H); 3.3(s, 3H); 1.5(d, 3H). | 401.41 |
| 14 | 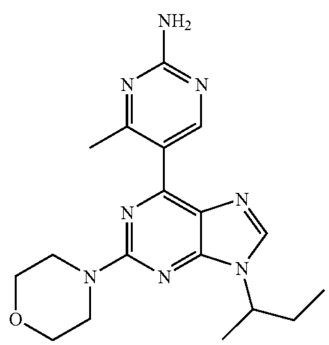 | (CDCl$_3$) δ 9.16(s, 1H); 7.84(s, 1H); 4.6(m, 1H); 3.86(m, 8 H); 2.88(s, 3H); 2.0(m, 2H); 1.65(d, 3H); 0.94(t, 3H). | 369.31 |
| 15 | 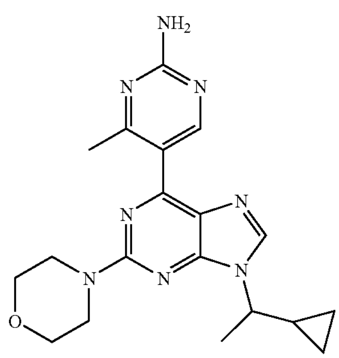 | (CDCl$_3$) δ 9.16(s, 1H); 7.84(s, 1H); 3.86(m, 8 H); 2.88(s, 3H); 1.65(d, 3H); 1.4(m, 2H); 0.81(m, 1H); 0.6(m, 1H); 0.46(m, 2H); | 381.29 |
| 16 | 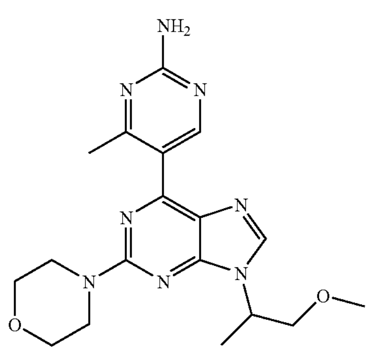 | (CDCl$_3$) δ 9.13(s, 1H); 7.99(s, 1H); 7.6(bs, 2H); 4.75(m, 1H); 3.9(m, 1H); 3.8-3.7(m, 8 H); 3.6(m, 1H); 3.4(s, 3H); 2.8(s, 3H); 1.6(d, 3H). | 385.3 |

TABLE 1-continued

Synthesised compounds

| Cmpd No | Structure | 1H-NMR | MS (M + 1) |
|---|---|---|---|
| 17 | 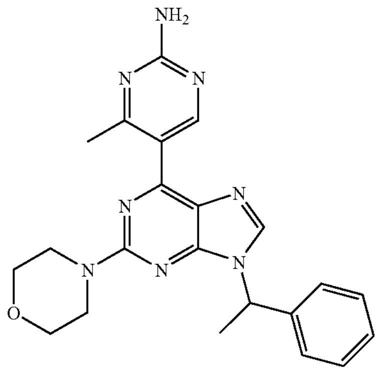 | (CDCl$_3$) δ 9.16(s, 1H); 7.84(s, 1H); 7.4(m, 5H); 5.9(m, 1H); 3.86(m, 8 H); 2.88(s, 3H); 2.0(d, 3H). | 417.31 |
| 18 | 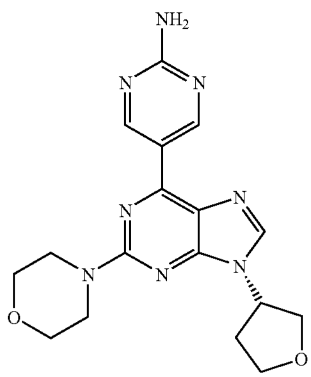 | (DMSO-d6) δ 9.52(s, 2H); 8.2(s, 1H); 7.3(s, 2H); 5.2(m, 1H); 4.2(m, 1H); 4.1(m, 2H); 3.9(m, 1H); 3.8(m, 4H); 3.7(m, 4H); 2.4(m, 2H). | 369.24 |
| 19 | 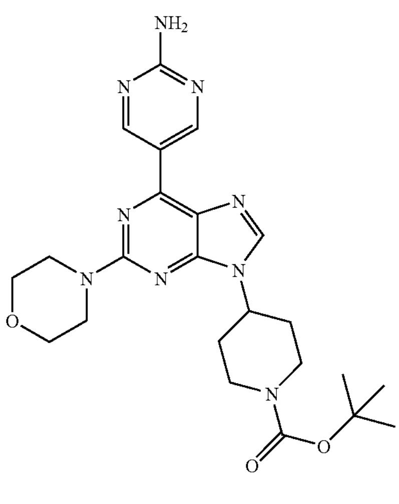 | (MeOD) δ 9.68(s, 2H), 8.27(s, 1H), 4.65(m, 1H), 4.28(m, 2H), 3.91(m, 4H), 3.80(m, 4H), 3.01 (m, 2H), 2.23(m, 2H), 2.10(m, 2H), 1.51(s, 9 H). | 482 |

TABLE 1-continued

Synthesised compounds

| Cmpd No | Structure | 1H-NMR | MS (M + 1) |
|---|---|---|---|
| 20 | 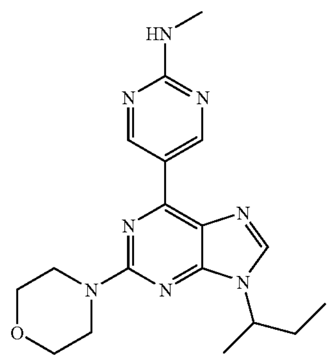 | (CDCl$_3$) δ 10.4(bs, 1H); 9.9(s, 1H); 9.6(s, 1H); 7.9(s, 1H); 4.6(m, 1H); 3.9(m, 4H); 3.8(m, 4H); 3.3(d, 3H); 2.0(m, 2H); 1.6(d, 3H); 1.0(t, 3H). | 369.30 |
| 21 | 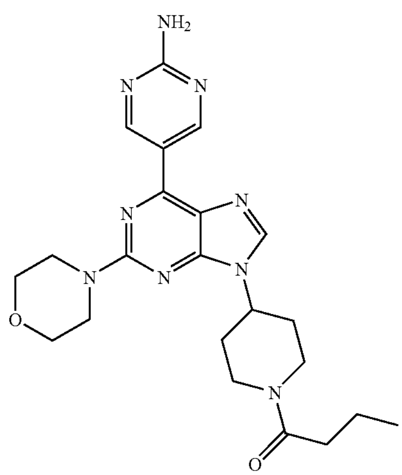 | (MeOD) δ 9.46(s, 2H), 8.07(s, 1H), 4.74(m, 2H), 4.01(m,1H), 3.77(m, 4H), 3.68(m, 4H), 2.75 (m, 1H), 2.34(m, 2H), 2.10(m, 5H), 1.57(m, 2H), 0.91(m, 3H). | 452 |
| 22 | 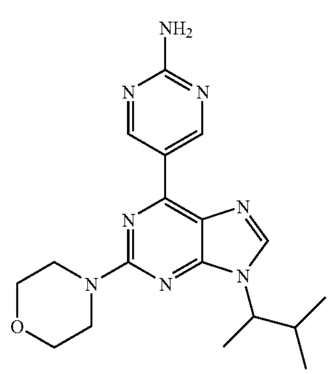 | (DMSO-d6) δ 9.53(s, 2H); 8.3(s, 1H); 7.33(bs, 2H); 4.31(m, 1H); 3.77(m, 4H); 3.72(m, 4H); 2.4(m, 1H); 1.5(d, 3H); 1.0(m, 3H); 0.7(m, 3H). | 369.28 |

TABLE 1-continued

Synthesised compounds

| Cmpd No | Structure | 1H-NMR | MS (M + 1) |
|---|---|---|---|
| 23 | 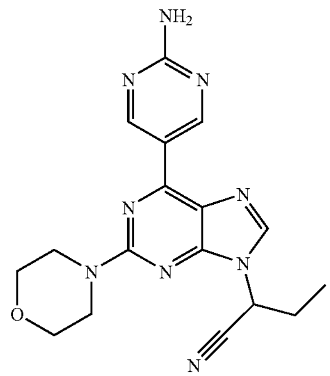 | (DMSO-d6) δ 9.56(s, 2H); 8.35(s, 1H); 7.40(bs, 2H); 5.81(t, 1H); 3.9(m, 4H); 3.8(m, 4H); 2.4(m, 2H); 0.9(t, 3H). | 366.18 |
| 24 | 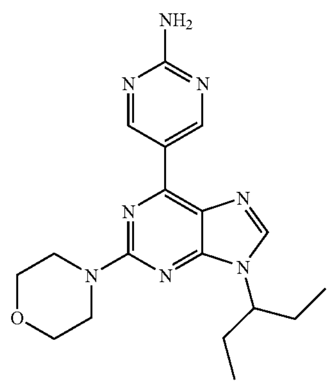 | (DMSO-d6) δ 9.54(s, 2H); 8.28(s, 1H); 7.37(bs, 2H); 4.3(m, 1H); 3.8(m, 4H); 3.7(m, 4H); 2.0(m, 4H); 0.7(t, 6H). | 369.21 |
| 25 | 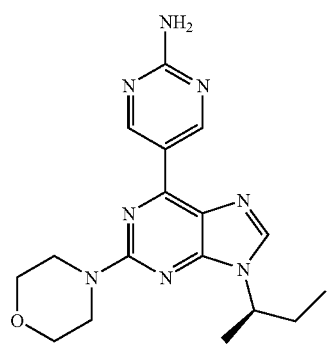 | (DMSO-d6) δ 9.52(s, 2H); 8.27(s, 1H); 7.28(s, 2H); 4.5(m, 2H); 3.8(m, 4H); 3.70(m, 4H); 2.0(m, 1H); 1.9(m, 1H); 1.6(d, 3H); 0.79(t, 3H). | 355.45 |
| 26 | 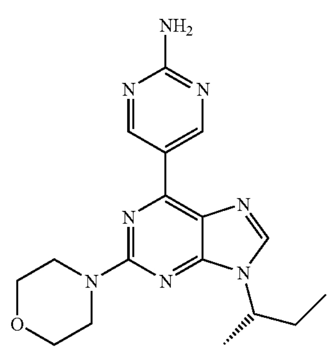 | (DMSO-d6) δ 9.52(s, 2H); 8.27(s, 1H); 7.28(s, 2H); 4.5(m, 2H); 3.8(m, 4H); 3.70(m, 4H); 2.0(m, 1H); 1.9(m, 1H); 1.6(d, 3H); 0.79(t, 3H). | 355.45 |

TABLE 1-continued
Synthesised compounds
| Cmpd No | Structure | 1H-NMR | MS (M + 1) |
|---|---|---|---|
| 27 | 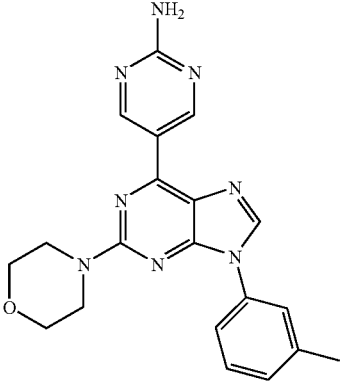 | (DMSO-d6) δ 9.56 (s, 2H); 8.64(s, 1H); 7.73(m, 2H); 7.50(t, 1H); 7.36(s, 2H); 7.28(m, 1H); 3.78(m, 4H); 3.73(m, 4H); 2.38(s, 3H). | 389.14 |
| 28 | 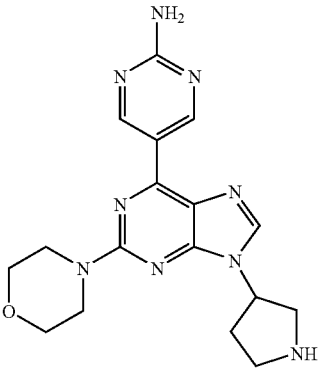 | (DMSO-d6) δ 9.46(2H, s); 8.25(1H, s); 7.35(2H, br s); 5.21-5.14(1H, m); 3.73-3.60(10H, m); 3.58-3.50(1H, m); 3.39-3.30(1H, m); 2.46(2H, overlapping). | 368.17 |
| 29 | 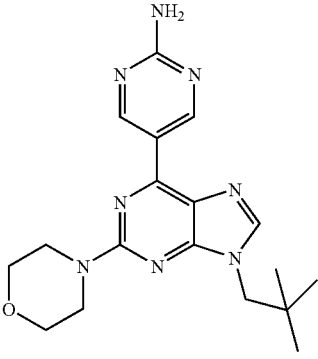 | (DMSO-d6) δ 9.54(s, 2H); 8.18(s, 1H); 3.66(s, 2H); 3.78(m, 4H); 3.73(m, 4H). | 369.15 |

TABLE 1-continued

Synthesised compounds

| Cmpd No | Structure | 1H-NMR | MS (M + 1) |
|---|---|---|---|
| 30 | 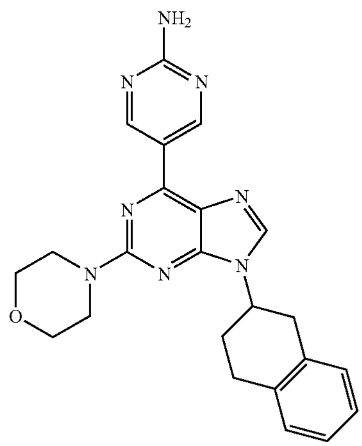 | (DMSO-d6) δ 9.54(s, 2H); 8.32(s, 1H); 7.34(bs, 2H); 7.16(m, 4H); 4.82(m, 1H); 3.78(m, 4H); 3.43(m, 4H); 3.21-3.0(m, 6H). | 429.19 |
| 31 | 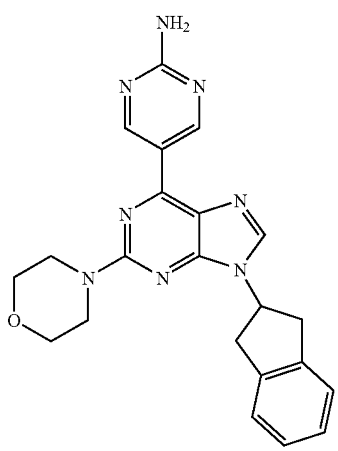 | (DMSO-d6) δ 9.52(s, 2H); 8.21(s, 1H); 7.33(bs, 2H); 7.24(m, 4H); 5.35(m, 1H); 3.78(m, 4H); 3.63(m, 4H); 3.58-3.40(m, 4H). | 415.15 |
| 32 | 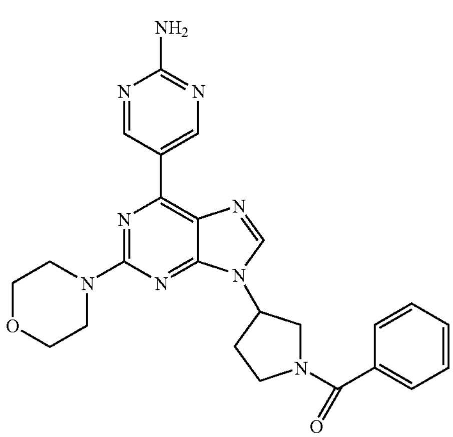 | na | 472.18 |

TABLE 1-continued
Synthesised compounds
| Cmpd No | Structure | 1H-NMR | MS (M + 1) |
|---|---|---|---|
| 33 | 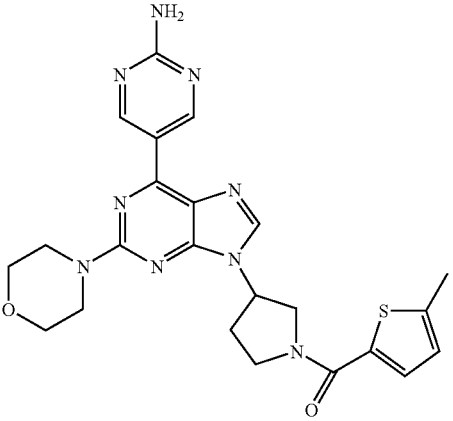 | (CDCl3) δ 9.74(2H, s); 7.80(1H, s); 7.39(3H, s); 6.77(1H, d); 5.19-5.13 (1H, m); 4.33(1H, b s); 4.24-4.19(1H, m); 4.09-4.04(1H, m); 4.00(1H, b s); 3.87-3.79(8H, m); 2.61-2.56(2H, m); 2.52 (3H, s). | 492.19 |
| 34 | 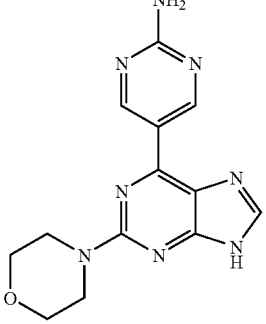 | (DMSO-d6) δ 12.83(1H, bs, D$_2$O exchangeable proton); 9.51(2H, s); 8.15 (1H, s); 7.25(2H, s, D$_2$O exchangeable protons); 3.73-3.74(4H, d); 3.69-3.70(4H, d). | 299.00 |
| 35 | 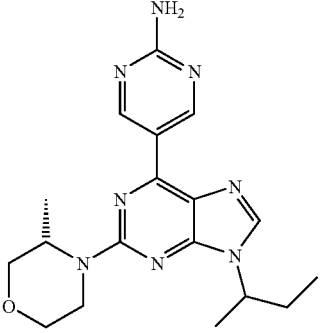 | (DMSO-d6) δ 9.51(2H, s); 8.27-8.25(1H, d); 7.25(2H, s, D$_2$O exchangeable proton); 4.72-4.70(1H, d); 4.51-4.46(1H, m); 4.37-4.35 (1H, d); 3.96-3.95(1H, d), 3.77-3.74(1H, d); 3.65-3.63(1H, d); 3.51-3.48(1H, t); 3.23-3.19 (1H, m); 2.05-1.85(2H, m); 1.54-1.52(3H, q); 1.22-1.20(3H, q); 0.78-0.74(3H, q). | 369.10 |
| 36 | 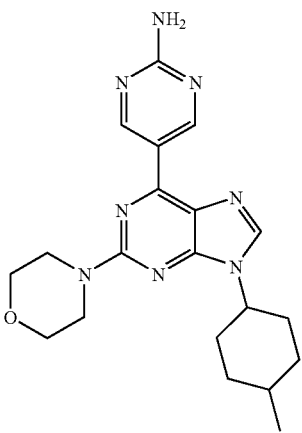 | (DMSO-d6) δ 9.53(2H, s); 8.35(1H, s); 7.37(2H, b s ); 4.37-4.31(1H, m); 3.77(4H, m); 3.72(4H, m); 2.31-2.21(2H, m); 1.99-1.91(1H, m); 1.78-1.65(4H, m); 1.57-1.52(2H, m); 1.07(3H, d, J = 7.1). | 295.21 |

TABLE 1-continued

Synthesised compounds

| Cmpd No | Structure | 1H-NMR | MS (M + 1) |
|---|---|---|---|
| 37 | 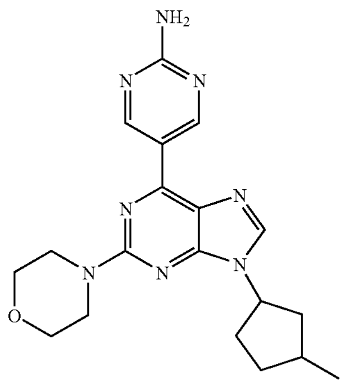 | Mixture of Diastereomers (2:1): (DMSO-d6): δ 9.50 (2H, s), 9.50(2H, s); 8.26 (1H, s), 8.28(1H, s); 7.26 (2H, s), 7.26(2H, s); 4.95-4.92(1H, m), 4.83-4.80 (1H, m); 3.77(4H, s), 3.77 (4H, s); 3.71-3.69(4H, t), 3.71-3.69(4H, t); 2.40-2.35(1H, m), 2.40-2.35 (1H, m); 2.30-2.13(2H, m), ,2.30-2.13(2H, m); 2.08-2.02(3H, m), 1.89-1.88(1H, m), 1.77-1.70 (2H, m); 1.55-1.53(1H, m), 1.32-1.21(1H, m); 1.10-1.08(3H, d), 1.04-1.02(3H, d). | 381.20 |
| 38 | 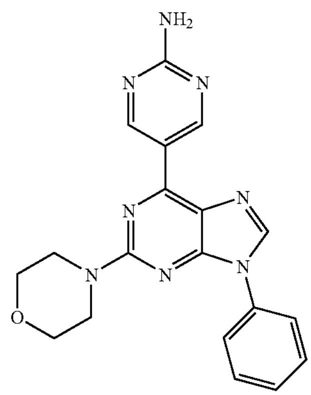 | (DMSO-d6) δ 9.53(s, 2H); 8.55(s, 1H); 8.20(s, 2H); 7.90(d, 2H); 7.56(t, 2H); 7.40(t, 1H); 3.77(m, 4H); 3.70(m, 4H). | 375.15 |
| 39 | 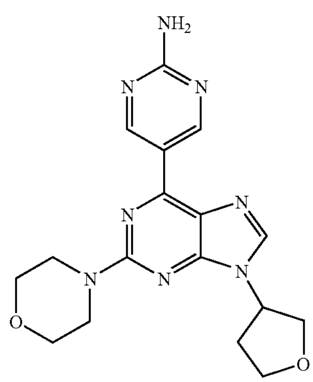 | (DMSO-d6) δ 9.52(s, 2H); 8.20(s, 1H); 7.29(s, 2H); 5.18(m, 1H); 4.16(m, 1H); 3.96(m, 2H); 3.86(m, 1H); 3.79(m, 4H); 3.68(m, 4H); 2.43(m, 2H). | 369.10 |
| 40 | 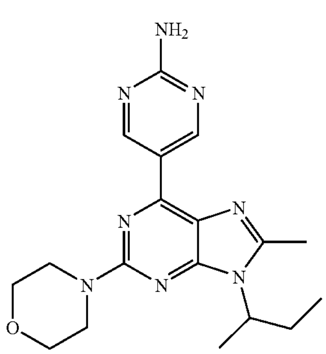 | (MeOD) δ 9.45(s, 2H), 4.55(m, 1H), 3.87(m, 4H), 3.80(m, 4H), 2.69(s, 3H), 2.43(m, 1H), 2.02 (m, 1H), 1.71(d, 3H), 0.86 (t, 3H). | 369.22 |

TABLE 1-continued

Synthesised compounds

| Cmpd No | Structure | 1H-NMR | MS (M + 1) |
|---|---|---|---|
| 41 | 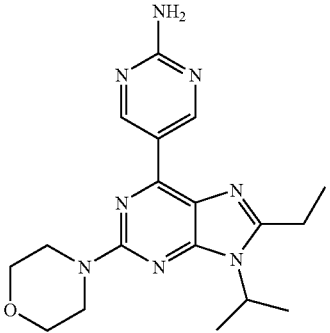 | (MeOD) δ 9.44(s, 2H), 4.64(m, 1H), 3.77(m, 4H), 3.69(m, 4H), 2.89 (m, 2H), 1.61(d, 6H), 1.21 (t, 3H). | 369.21 |
| 42 | 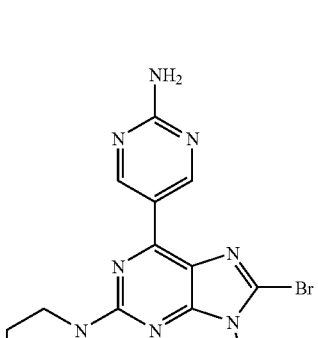 | (MeOD) δ 9.58(s, 2H), 4.64(m, 1H), 3.87(m, 4H), 3.80(m, 4H), 2.46 (m, 1H), 2.00(m, 1H), 1.71(d, 3H), 0.82(t, 3H). | 434 |

Biological Testing mTOR Assay

Truncated mTOR kinase and His-tagged 4eBP1 were produced in-house. [γ$^{33}$P]-ATP was purchased from Amersham (GE Healthcare). All chemicals, unless otherwise stated, were from Sigma-Aldrich.

Phosphorylation assays were initially performed in a final volume of 20 μL in 384-well polypropylene plate (Greiner). Compounds were typically tested over the range from 100 μM to 0.006 μM, in 8 step dilutions, in duplicate. 10 μL/well of 2× Enzyme-Substrate solution (1.5 μg/mL mTOR, 40 μg/mL 4eBP1 in 1× assay buffer: 10 mM Hepes pH 7.5, 50 mM NaCl and 10 mM MnCl$_2$) were first added to the sample plate containing 1 μL/well of test compound in neat DMSO. The reaction was initiated by adding 10 μL/well of 20 μM ATP solution (final assay concentration 10 μM ATP and 0.4 μCi/well of [γ$^{33}$P]-ATP). After 1 hour incubation at room temperature, the reaction was terminated with 40 μL/well of 20 mM EDTA/1 mM ATP solution.

50 μL/well of the stopped reaction mix was then transferred to 384-well MultiScreenHTS-PH filter plate (Millipore) pre-added with 50 μL/well of 1% phosphoric acid. The plate was washed 4 times with 120 μL/well of 0.5% phosphoric acid via vacuum filtration. Finally, 10 μL/well of Optiphase™ SuperMix liquid scintillation cocktail (Perkin Elmer) was added. After minimum 1 hour of incubation, counting was performed in a Wallac MicroBeta TriLux scintillation counter using coincidence counting mode with crosstalk correction.

IC$_{50}$ is defined as the concentration of compound required for 50% inhibition of kinase enzyme activity. IC$_{50}$ data are shown in Table 2 below.

PI3K Assay

Recombinant PI3K p110α/p85 was prepared in-house. Phosphatidylinositol (PtdIns), phosphotidylserine (PtdSer) and all other unspecified chemicals were purchased from Sigma-Aldrich. [γ$^{33}$P]ATP and Optiphase scintillant were obtained from Perkin Elmer.

Assays were performed in a final assay volume of 25 μL in 384-well Maxisorp plates (Nunc). Compounds were tested at 8 concentrations in 3-fold serial dilution, generally starting from 10 μM. Maxisorp plates were coated with 20 μL/well of a 1:1 mixture of PtdIns and PtdSer [0.1 mg/mL each dissolved in chloroform:ethanol (3:7)] and left overnight in a fume hood at room temperature (RT) to dry.

The enzyme reaction was created by pipetting 5 μL/well of compound (in 2.5% DMSO), 10 μL/well of enzyme (0.5 μg/mL p110α+1 μg/mL p85), and 10 μL/well of 5 μM ATP with 5 μCi/mL [γ$^{33}$]ATP in assay buffer (final concentrations: 0.2 μg/mL p110α, 2 μM ATP, 0.05 μCi/well [γ$^{33}$P]ATP in 1× assay buffer: 100 mM Tris-HCl pH 7.0, 200 mM NaCl, 8 mM MgCl$_2$). The reaction was incubated for 1 hour at RT and terminated with 30 μL/well of 50 mM EDTA solution. The plate was then washed twice with TBS, dried, and added with 30 μL/well of scintillant before it was counted in a MicroBeta Trilux. IC$_{50}$ is defined as the concentration of compound required for 50% inhibition of kinase enzyme activity. IC$_{50}$ data are shown in Table 2 below.

TABLE 2

In vitro mTOR and PI3K inhibition activity assay $IC_{50}$ data

| Compound Number | $IC_{50}$ (mTOR)* | $IC_{50}$ (PI3Kα)* |
|---|---|---|
| 1 | ++ | +++ |
| 2 | +++ | +++ |
| 3 | +++ | +++ |
| 4 | + | +++ |
| 5 | ++ | +++ |
| 6 | ++ | +++ |
| 7 | +++ | +++ |
| 8 | +++ | +++ |
| 9 | ++ | +++ |
| 10 | +++ | +++ |
| 11 | ++ | +++ |
| 12 | +++ | +++ |
| 13 | ++ | +++ |
| 14 | + | +++ |
| 15 | + | +++ |
| 16 | + | +++ |
| 17 | + | +++ |
| 18 | +++ | +++ |
| 19 | +++ | +++ |
| 20 | +++ | +++ |
| 21 | +++ | +++ |
| 22 | +++ | +++ |
| 23 | +++ | +++ |
| 24 | +++ | +++ |
| 25 | +++ | +++ |
| 26 | +++ | +++ |
| 27 | +++ | +++ |
| 28 | ++ | na |
| 29 | +++ | +++ |
| 31 | +++ | +++ |
| 32 | +++ | +++ |
| 33 | +++ | +++ |
| 34 | ++ | +++ |
| 35 | +++ | +++ |
| 36 | +++ | +++ |
| 37 | +++ | +++ |
| 38 | +++ | +++ |

*+++ <1 μm
++ 1 μM-5 μM
+ >5 μM
na not available

Cell-Based Proliferation Assay

The biological efficacy of the invention was demonstrated by the following assay. Human cancer cell lines PC3 and DU145 (human prostate cancer cell lines), were obtained from ATCC. They were cultured in the media according to the ATCC work instructions. PC3 and DU145 cells were seeded at 1,000 cells per well in 96-well plates, respectively. The plates were incubated at 37° C., 5% $CO_2$, for 24 h. Cells were treated with compounds at various concentrations for 96 h. Cell proliferation was then quantified using Celltiter96 Aqueous One Solution Cell Proliferation Assay from Promega (Madison Wis.). Dose response curves were plotted to determine $IC_{50}$ values for the compounds using XL-fit (ID Business Solution, Emeryville, Calif.). $IC_{50}$ is defined as the concentration of compound required for 50% inhibition of cell proliferation. The compounds of this invention inhibited cell proliferation as shown in Table 3 below. The data indicated that the compounds of this invention are active in the inhibition of tumour cell growth. $IC_{50}$ data are shown in Table 3 below.

TABLE 3

Cell-based proliferation assay $IC_{50}$ data

| Compound No. | PC3 | DU145 |
|---|---|---|
| 2 | +++ | NT |
| 3 | NT | ++ |
| 10 | +++ | NT |
| 18 | +++ | NT |
| 19 | +++ | NT |
| 21 | +++ | NT |
| 22 | +++ | NT |
| 23 | +++ | NT |
| 25 | +++ | NT |
| 26 | +++ | NT |
| 29 | +++ | NT |
| 35 | +++ | NT |
| 37 | +++ | NT |
| 42 | +++ | NT |

NT = not tested $IC_{50} \leq 1$ μM +++

$1$ μM $< IC_{50} \leq 5$ μM ++

$IC_{50} > 5$ μM +

In Vivo Antineoplastic (or Anti-Tumour) Effect:

The efficacy of the compounds of the invention can then be determined using in vivo animal xenograft studies. The animal xenograft model is one of the most commonly used in vivo cancer models.

In these studies, female athymic nude mice, 12-14 weeks of age would be implanted subcutaneously in the flank with $5 \times 10^6$ cells of PC-3 human prostate cancer cell line in 50% Matrigel (BD Biosciences). When the tumour reaches the size 100 $mm^3$, the xenograft nude mice would be paired-match into various treatment groups. The selected kinase inhibitors would be dissolved in appropriate vehicles and administered to the xenograft nude mice intraperitoneally or orally daily for 28 days. The dosing volume will be 0.01 ml/g body weight. Tumour volume will be calculated twice weekly post-injection using the formula: Volume $(mm^3)=(w^2 \times l)/2$, where w=width and l=length in mm of a MV4-11tumour. Compounds of this invention that have been tested show significant reduction in tumour volume relative to controls treated with vehicle only. The result will therefore indicate that compounds of this invention are efficacious in treating a proliferative disease such as cancer.

The details of specific embodiments described in this invention are not to be construed as limitations. Various equivalents and modifications may be made without departing from the essence and scope of this invention, and it is understood that such equivalent embodiments are part of this invention.

What is claimed is:

1. A compound of formula (I):

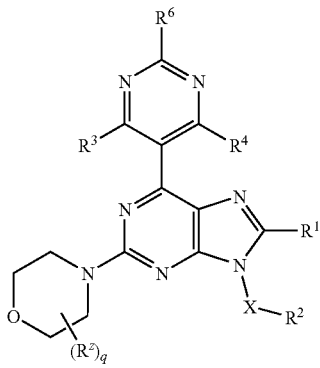

Formula (I)

wherein:
R$^1$ is selected from the group consisting of: H, halogen and optionally substituted C$_1$-C$_6$ alkyl;
R$^2$ is selected from the group consisting of H, halogen, OH, NO$_2$, CN, NH$_2$, optionally substituted C$_1$-C$_{12}$alkyl, optionally substituted C$_2$-C$_{12}$alkenyl, optionally substituted C$_2$-C$_{12}$alkynyl, optionally substituted C$_2$-C$_{12}$heteroalkyl, optionally substituted C$_3$-C$_{12}$cycloalkyl, optionally substituted C$_3$-C$_{12}$cycloalkenyl, optionally substituted C$_2$-C$_{12}$heterocycloalkyl, optionally substituted C$_2$-C$_{12}$heterocycloalkenyl, optionally substituted C$_6$-C$_{18}$aryl, optionally substituted C$_1$-C$_{18}$ heteroaryl, optionally substituted C$_1$-C$_{12}$alkyloxy, optionally substituted C$_2$-C$_{12}$alkenyloxy, optionally substituted C$_2$-C$_{12}$alkynyloxy, optionally substituted C$_2$-C$_{10}$heteroalkyloxy, optionally substituted C$_3$-C$_{12}$cycloalkyloxy, optionally substituted C$_3$-C$_{12}$cycloalkenyloxy, optionally substituted C$_2$-C$_{12}$heterocycloalkyloxy, optionally substituted C$_2$-C$_{12}$ heterocycloalkenyloxy, optionally substituted C$_6$-C$_{18}$aryloxy, optionally substituted C$_1$-C$_1$ heteroaryloxy, optionally substituted C$_1$-C$_{12}$alkylamino, SR$^8$, SO$_3$H, SO$_2$NR$^8$R$^9$, SO$_2$R$^8$, SONR$^8$R$^9$, SOR$^8$, COR$^8$, COOH, COOR$^8$, CONR$^8$R$^9$, NR$^8$COR$^9$, NR$^8$COOR$^9$, NR$^8$SO$_2$R$^9$, NR$^8$CONR$^8$R$^9$, NR$^8$R$^9$, and acyl;
R$^3$, and R$^4$ are each independently selected from the group consisting of H, F, Cl, Br, OH, optionally substituted C$_1$-C$_6$alkyl, OR$^8$, OCOR$^8$, CH$_2$OH, NH$_2$, NR$^8$R$^9$, NR$^8$COR$^9$, and NR$^8$SO$_2$R$^9$;
R$^6$ is selected from the group consisting of H, OH, OR$^8$, OP$_g^O$, OCOR$^8$, CH$_2$OH, NH$_2$, NR$^8$R$^9$, NR$^8$P$_g^N$, N(P$_g^N$)$_2$, NR$^8$COR$^9$, and NR$^8$SO$_2$R$^9$; or
R$^8$ and R$^9$ when taken together with the atoms to which they are attached form an optionally substituted cyclic moiety;
each R$^8$ and R$^9$ is independently selected from the group consisting of H, optionally substituted C$_1$-C$_{12}$alkyl, optionally substituted C$_2$-C$_{12}$alkenyl, optionally substituted C$_2$-C$_{12}$alkynyl, optionally substituted C$_2$-C$_{10}$heteroalkyl, optionally substituted C$_3$-C$_{12}$cycloalkyl, optionally substituted C$_3$-C$_{12}$cycloalkenyl, optionally substituted C$_2$-C$_{12}$ heterocycloalkyl, optionally substituted C$_2$-C$_{12}$ heterocycloalkenyl, optionally substituted C$_6$-C$_{18}$aryl, and optionally substituted C$_1$-C$_{18}$heteroaryl;

P$_g^O$ is a protecting group for oxygen;
each P$_g^N$ is independently a protecting group for nitrogen;
each R$^z$ is independently selected from the group consisting of C$_1$-C$_6$alkyl, halo-C$_1$-C$_6$alkyl, hydroxyC$_1$-C$_6$alkyl, C$_1$-C$_6$alkyloxyC$_1$-C$_6$alkyl, cyanoC$_1$-C$_6$alkyl, aminoC$_1$-C$_6$alkyl, C$_1$-C$_6$alkylaminoC$_1$-C$_6$alkyl, and di(C$_1$-C$_6$alkyl)aminoC$_1$-C$_6$alkyl;
q is an integer selected from the group consisting of 0, 1, 2, 3, and 4;
X is a group of formula (CR$^{10}$$_2$)$_m$;
each R$^{10}$ is independently selected from the group consisting of: H and optionally substituted C$_1$-C$_6$ alkyl;
m is an integer selected from the group consisting of 0, 1, 2, 3 and 4;
or a pharmaceutically acceptable salt, N-oxide, or prodrug thereof.

2. A compound according to claim 1 wherein q is 0.

3. A compound according to claim 1 wherein R$^3$ is H.

4. A compound according to claim 1 wherein R$^4$ is H.

5. A compound according to claim 1 wherein m is selected from the group consisting of 0, 1, and 2.

6. A compound according to claim 1, wherein m is 1, wherein one R$^{10}$ is H and X is a group of the formula:

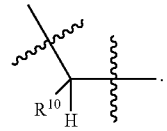

7. A compound according to claim 1 wherein the compound is a compound of the formula:

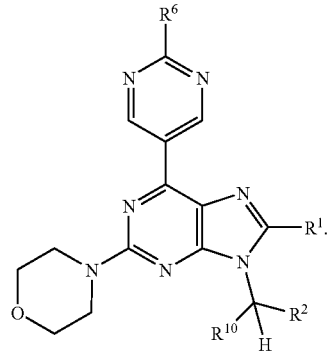

8. A compound according to claim 1 wherein R$^{10}$ is selected from the group consisting of H, methyl, ethyl, propyl, isopropyl, and butyl.

9. A compound according to claim 1 wherein R$^1$ is H.

10. A compound according to claim 1 wherein R$^6$ is selected from the group consisting of NH$_2$ and NR$^8$R$^9$ wherein R$^8$ and R$^9$ are as defined in claim 1.

11. A compound according to claim 1 wherein R$^6$ is NH$_2$.

12. A compound according to claim 1 wherein R$^2$ is selected from the group consisting of H, cyano, optionally substituted C$_1$-C$_{12}$alkyl, optionally substituted C$_2$-C$_{12}$alkenyl, optionally substituted C$_2$-C$_{12}$heteroalkyl, optionally substituted C$_3$-C$_{12}$cycloalkyl, optionally substituted C$_2$-C$_{12}$heterocycloalkyl, optionally substituted C$_6$-C$_{18}$aryl, and optionally substituted C$_1$-C$_{18}$heteroaryl.

13. A compound according to claim 12 wherein the optionally substituted $C_6$-$C_{18}$ aryl is a group of the formula:

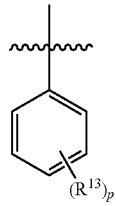

wherein p is an integer selected from the group consisting of 0, 1, 2, 3, 4, and 5;

each $R^{13}$ is independently selected from the group consisting of H, halogen, OH, $NO_2$, CN, $NH_2$, optionally substituted $C_1$-$C_{12}$alkyl, optionally substituted $C_2$-$C_{12}$ alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_1$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^8$, $SO_3H$, $SO_2NH_2$, $SO_2R^8$, $SONH_2$, $SOR^8$, $COR^8$, COOH, $COOR^8$, $CONR^8R^9$, $NR^8COR^9$, $NR^8COOR^9$, $NR^8SO_2R^9$, $NR^8CONR^8R^9$, $NR^8R^9$, and acyl;

where each $R^8$ and $R^9$ is independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{10}$heteroalkyl, optionally substituted $C_3$-$C_{12}$cycloalkyl, optionally substituted $C_3$-$C_{12}$cycloalkenyl, optionally substituted $C_2$-$C_{12}$ heterocycloalkyl, optionally substituted $C_2$-$C_{12}$ heterocycloalkenyl, optionally substituted $C_6$-$C_{18}$aryl, and optionally substituted $C_1$-$C_{12}$heteroaryl.

14. A compound according to claim 12 wherein the optionally substituted $C_6$-$C_{18}$ aryl is a group of the formula:

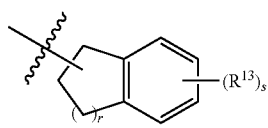

wherein $R^{13}$ is independently selected from the group consisting of H, halogen, OH, $NO_2$, CN, $NH_2$, optionally substituted $C_1$-$C_{12}$alkyl, optionally substituted $C_2$-$C_{12}$ alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_1$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^8$, $SO_3H$, $SO_2NH_2$, $SO_2R^8$, $SONH_2$, $SOR^8$, $COR^8$, COOH, $COOR^8$, $CONR^8R^9$, $NR^8COR^9$, $NR^8COOR^9$, $NR^8SO_2R^9$, $NR^8CONR^8R^9$, $NR^8R^9$, and acyl;

s is an integer selected from the group consisting of 0, 1, 2, 3 and 4;

r is an integer selected from the group consisting of 1, 2, and 3.

15. A compound according to claim 12 wherein $R^2$ is an optionally substituted $C_1$-$C_{12}$ alkyl group of the formula:

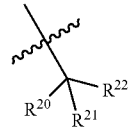

wherein $R^{20}$, $R^{21}$, and $R^{22}$ are each independently selected from the group consisting of H, Cl, Br, F, OH, $NO_2$, CN, $NH_2$, optionally substituted $C_1$-$C_{12}$alkyl, optionally substituted $C_2$-$C_{12}$heteroalkyl, optionally substituted $C_3$-$C_{12}$cycloalkyl, optionally substituted $C_2$-$C_{12}$heterocycloalkyl, optionally substituted $C_6$-$C_{18}$aryl, and optionally substituted $C_1$-$C_{18}$heteroaryl; or any two or more of $R^{20}$, $R^{21}$ and $R^{22}$ when taken together with the carbon atom to which they are attached form a cyclic moiety.

16. A compound according to claim 12 wherein $R^2$ is selected from the group consisting of methyl, ethyl, isopropyl, propyl, 3,3-dimethyl-propyl, cyclopropyl, cyclopentyl, 3-methycyclopentyl, cyclohexyl, 4-methylcyclohexyl, butyl, sec-butyl, isobutyl, 3,3-dimethyl-butyl, 2-ethyl-butyl, pentyl, pent-4-enyl, hexyl, heptyl, octyl, cyano, methoxymethyl, butoxymethyl, t-butoxymethyl, and tetrahydrofuran-3-yl.

17. A compound according to claim 1 selected from the group consisting of:

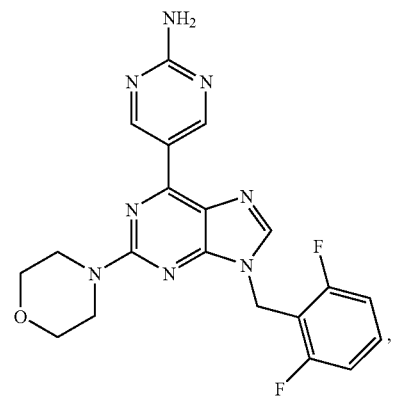

-continued
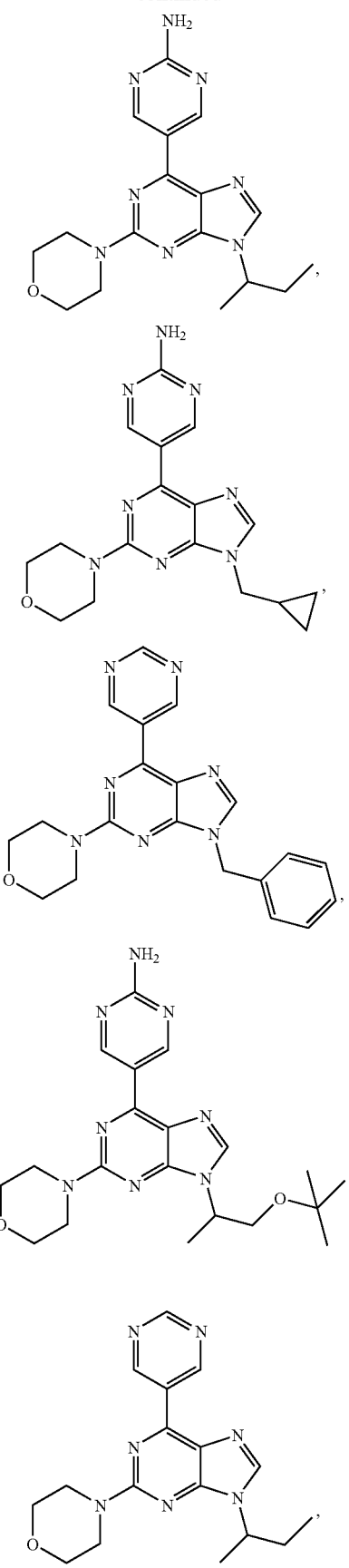
-continued
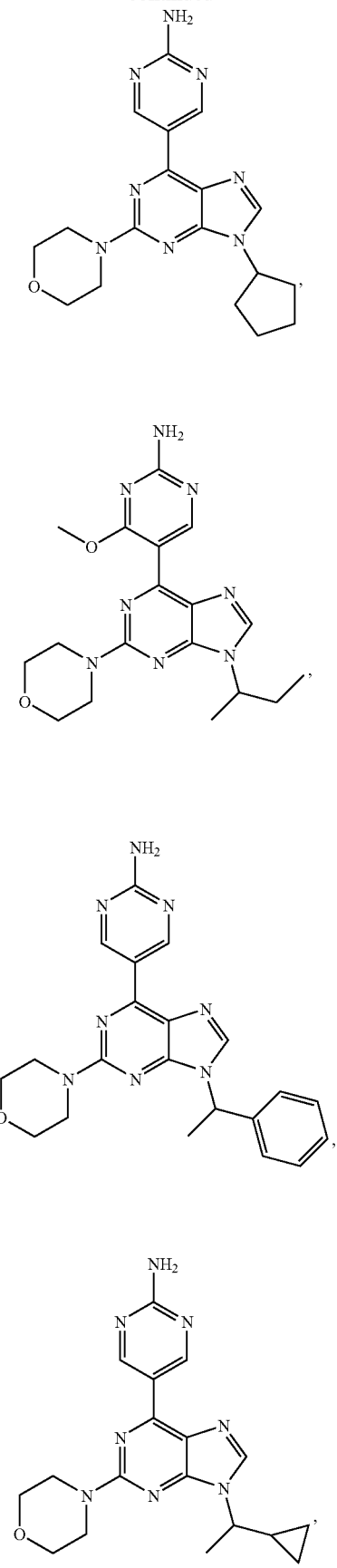

93
-continued
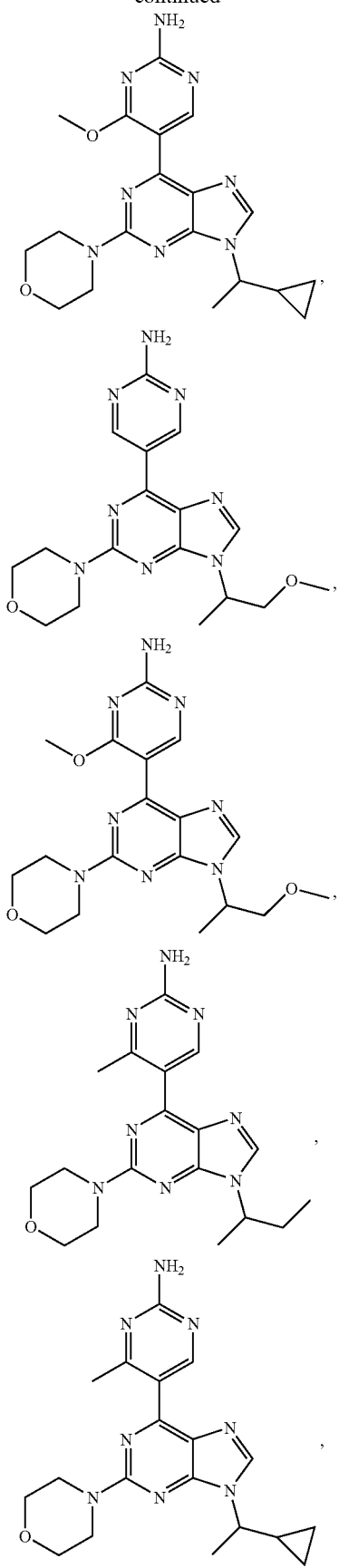
94
-continued
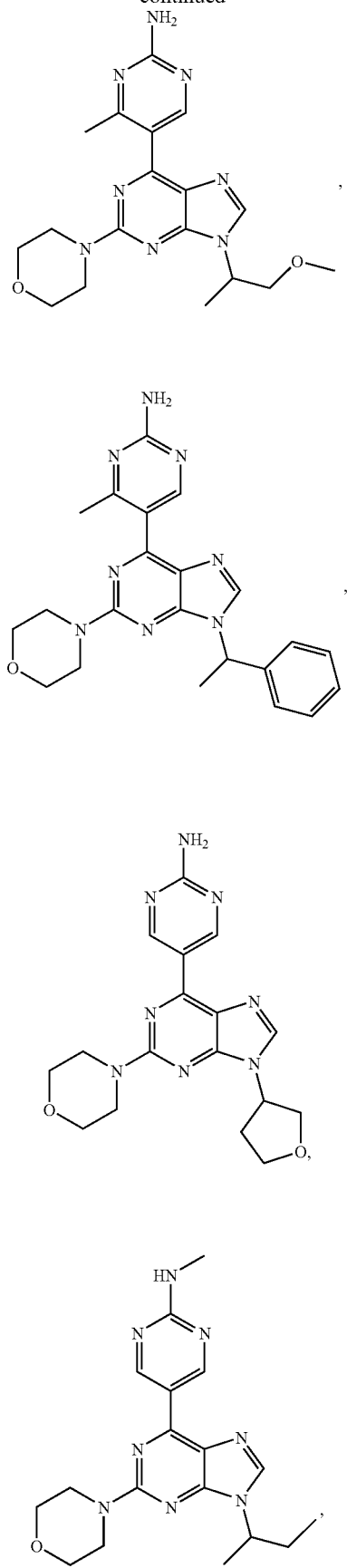

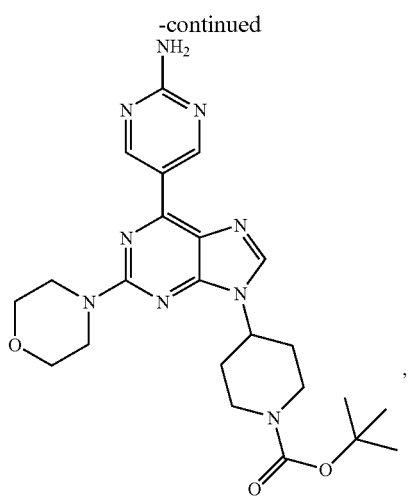
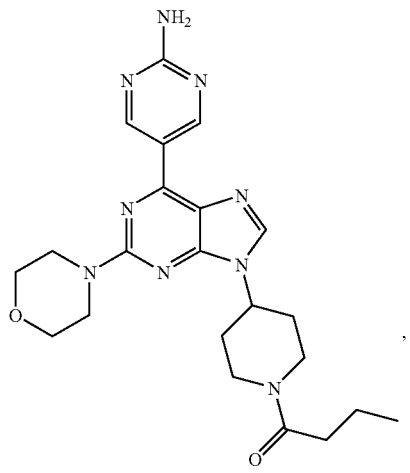
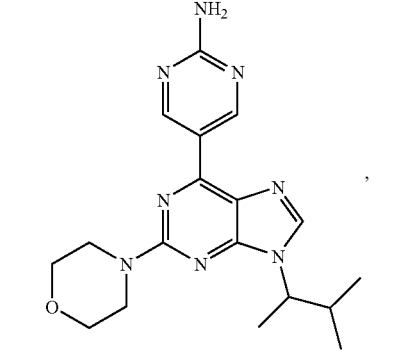
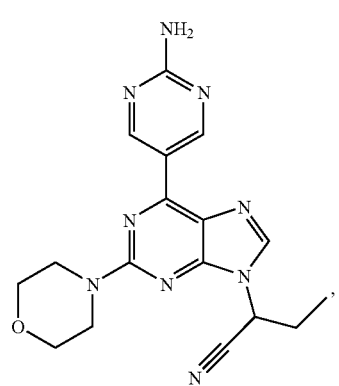
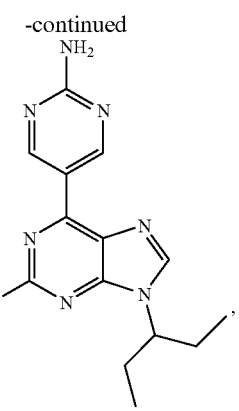
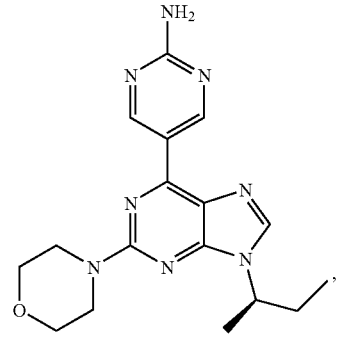
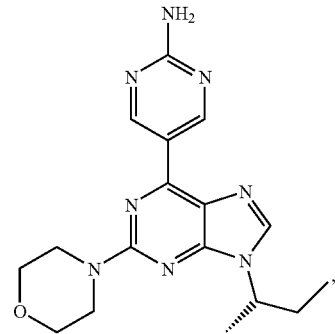
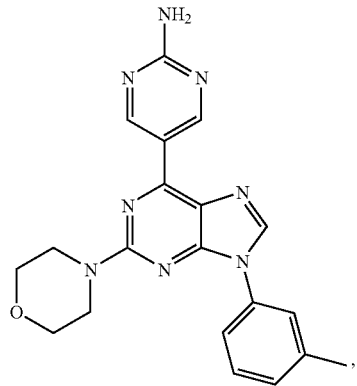

97
-continued
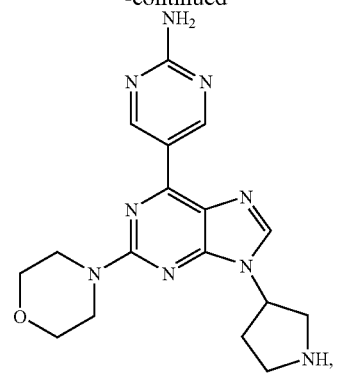
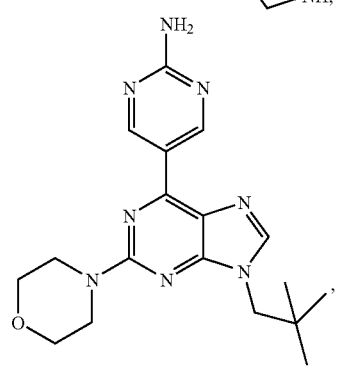
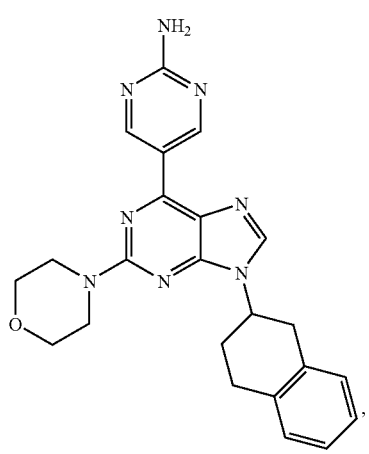
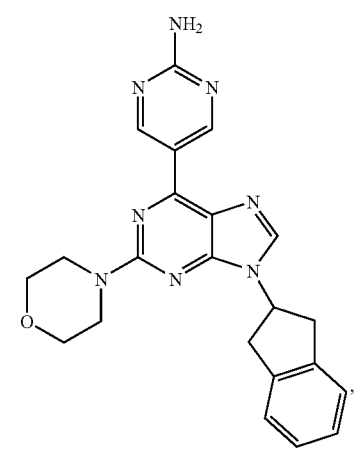
98
-continued
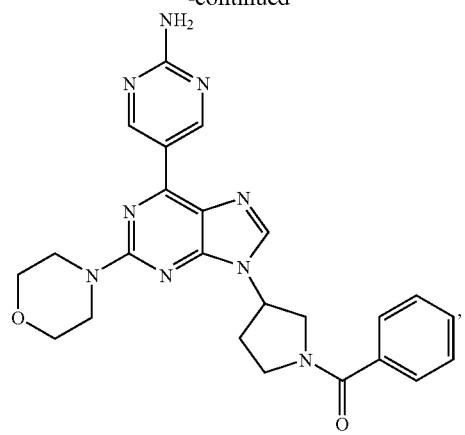
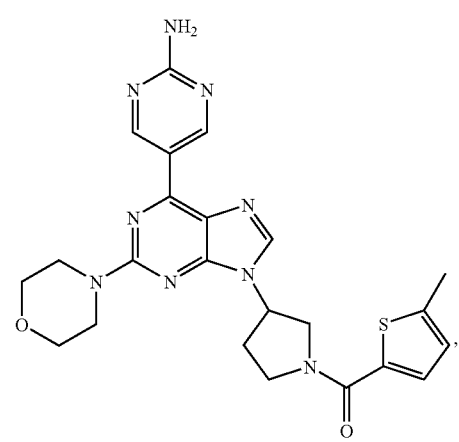
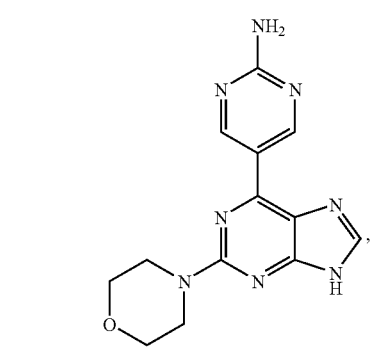
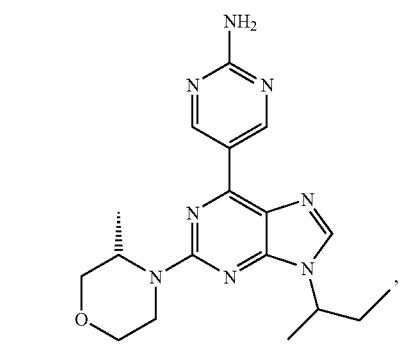

99
-continued
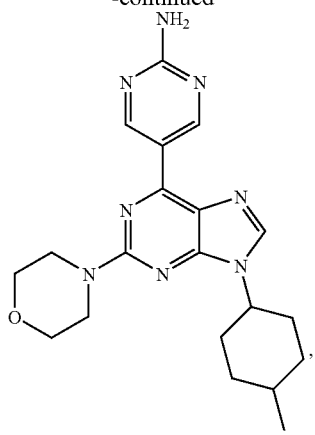
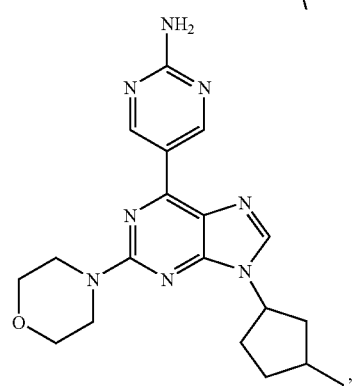
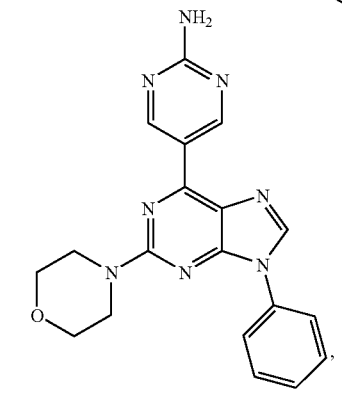
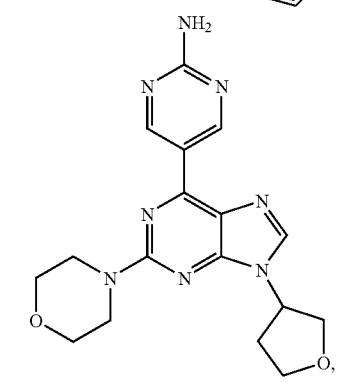
100
-continued
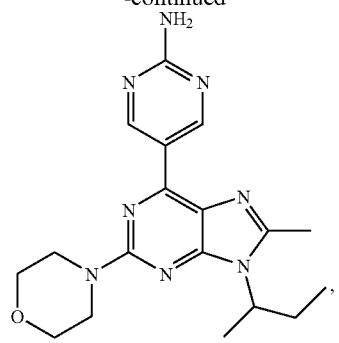
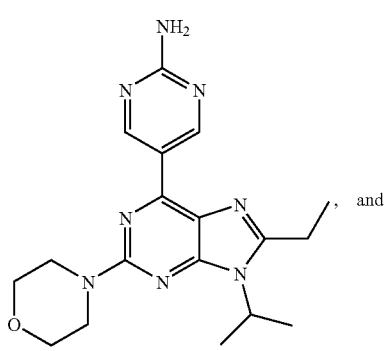, and
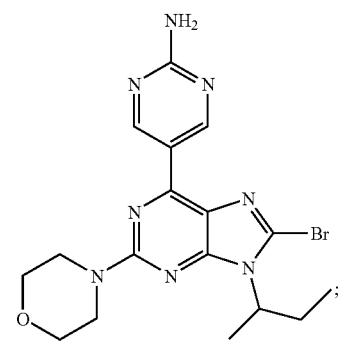;
or a pharmaceutically acceptable salt or prodrug thereof.
18. A pharmaceutical composition including a compound according to claim 1 and a pharmaceutically acceptable diluent, excipient or carrier.
* * * * *